(12) United States Patent
Kashima et al.

(10) Patent No.: US 6,172,228 B1
(45) Date of Patent: Jan. 9, 2001

(54) PROCESS FOR PRODUCING PIPERAZINESULFONAMIDE DERIVATIVES AND SALTS THEREOF

(75) Inventors: Kenichi Kashima, Fujiidera; Yasuhiko Sakamoto, Habikino; Yoichiro Ohta, Takatsuki; Kenji Kawanishi, Osaka; Shigetaka Takemura, Osaka; Yasuko Takemura, Osaka, all of (JP)

(73) Assignee: Azwell Inc., Osaka (JP)

( * ) Notice: Under 35 U.S.C. 154(b), the term of this patent shall be extended for 0 days.

(21) Appl. No.: 09/453,223

(22) Filed: Dec. 3, 1999

Related U.S. Application Data

(63) Continuation-in-part of application No. PCT/JP98/02399, filed on May 29, 1998.

(30) Foreign Application Priority Data

Jun. 4, 1997 (JP) .................................... 9-163437

(51) Int. Cl.⁷ ..................... C07D 401/06; C07D 241/04; C07D 295/023
(52) U.S. Cl. ............................. 544/360; 544/398
(58) Field of Search ..................... 544/360, 398

(56) References Cited

U.S. PATENT DOCUMENTS

| | | | |
|---|---|---|---|
| 5,478,941 | 12/1995 | Cossement et al. | 544/383 |
| 5,716,950 | 2/1998 | Kashima et al. | 514/218 |

FOREIGN PATENT DOCUMENTS

| | | |
|---|---|---|
| 0558245A1 | 9/1993 | (EP) . |
| 2225321 | 5/1990 | (GB) . |
| WO 9519345 * | 7/1995 | (WO) . |
| 95 19345 | 7/1995 | (WO) . |

OTHER PUBLICATIONS

Synthesis, "A novel synthesis of the enantimers of an antihistamine drug by piperazine formation from a primary amine," Opalka et al., 766–768, Jan. 1995.

Synthesis, "A Novel Synthesis of the Enantiomers of an Antihistamine Drug by Piperazine Formation from a Primary Amine," Opalka et al., Jan. 27, 1995, pp. 766–768.

Patent Abstracts of Japan, 62153280 A, Jul. 8, 1987.

* cited by examiner

*Primary Examiner*—Mukund J. Shah
*Assistant Examiner*—Hong Liu
(74) *Attorney, Agent, or Firm*—Birch, Stewart, Kolasch & Birch, LLP

(57) ABSTRACT

A process for advantageously preparing a piperazinesulfonamide derivative represented by the general formula (III):

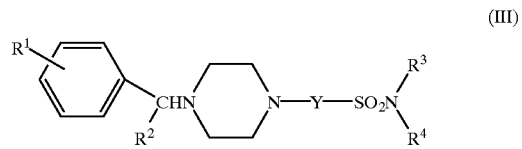

wherein $R^1$ is hydrogen atom, a straight or branched chain alkyl group having 1 to 6 carbon atoms, an alkoxy group having 1 to 4 carbon atoms, a halogen atom, hydroxyl group, trifluoromethyl group, nitro group or amino group; $R^2$ is a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group, 2-pyridyl group, 3-pyridyl group or 4-pyridyl group; each of $R^3$ and $R^4$ is independently hydrogen atom, a straight or branched chain alkyl group having 1 to 6 carbon atoms, a hydroxyalkyl group having 1 to 4 carbon atoms, a cycloalkyl group having 3 to 8 carbon atoms, or a phenyl group which may be substituted; and Y is an alkylene group having 1 to 12 carbon atoms, and a salt thereof.

17 Claims, No Drawings

PROCESS FOR PRODUCING PIPERAZINESULFONAMIDE DERIVATIVES AND SALTS THEREOF

This application is a continuation-in-part application of PCT/JP98/02399, filed May 29, 1998, the entire contents of which are incorporated herein by reference.

BACKGROUND OF THE INVENTION

1. Field of the Invention

The present invention relates to a process for preparing a piperazinesulfonamide derivative and a pharmaceutically acceptable salt thereof. More specifically, the present invention relates to a process for preparing a piperazinesulfonamide derivative and a pharmaceutically acceptable salt thereof which have excellent antiallergic activity and thereby are useful as a medicament for preventing and treating diseases such as bronchial asthma, allergic rhinitis, atopic dermatitis, urticaria and the like.

2. Discussion of the Related Art

Conventionally, as processes for preparing a piperazinesulfonamide derivative, there have been known, for instance, process A, process B and process C which are described in WO95/19345 Pamphlet.

However, since the reaction processes of process A and process C are long, and the yield of the piperazinesulfonamide derivative is low, it cannot be said that these processes are industrially advantageous. In addition, since process B requires a long period of time for completion of the reaction, and the yield is not a satisfactory level, it cannot be said that process B is industrially advantageous.

Therefore, recently, it has been required to develop a process capable of industrially advantageously preparing a piperazinesulfonamide derivative in a short period of time and at high yield.

In view of the above prior art, the present invention has been accomplished, and an object of the present invention is to provide a process for efficiently and industrially advantageously preparing a piperazinesulfonamide derivative and a pharmaceutically acceptable salt thereof.

These and other objects of the present invention will be apparent from the following description.

SUMMARY OF THE INVENTION

In sum, the present invention pertains to:

(1) a process for preparing a piperazinesulfonamide derivative represented by the general formula (III):

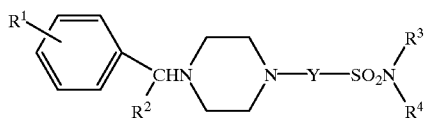

(III)

wherein $R^1$ is hydrogen atom, a straight or branched chain alkyl group having 1 to 6 carbon atoms, an alkoxy group having 1 to 4 carbon atoms, a halogen atom, hydroxyl group, trifluoromethyl group, nitro group or amino group; $R^2$ is a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group, 2-pyridyl group, 3-pyridyl group or 4-pyridyl group; each of $R^3$ and $R^4$ is independently hydrogen atom, a straight or branched chain alkyl group having 1 to 6 carbon atoms, a hydroxyalkyl group having 1 to 4 carbon atoms, a cycloalkyl group having 3 to 8 carbon atoms, or a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group; and Y is an alkylene group having 1 to 12 carbon atoms, characterized by reacting a piperazine derivative represented by the general formula (I):

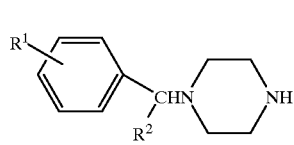

(I)

wherein $R^1$ and $R^2$ are as defined above, with a halogenoalkylsulfonamide derivative represented by the general formula (II):

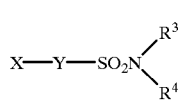

(II)

wherein $R^3$, $R^4$ and Y are as defined above; and X is chlorine atom, bromine atom or iodine atom, in the presence of an organic base and in the absence of a solvent; and (2) a process for preparing a pharmaceutically acceptable salt of a piperazinesulfonamide derivative represented by the general formula (III):

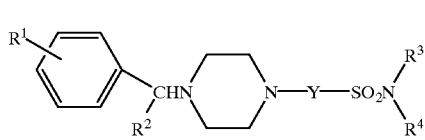

(III)

wherein $R^1$ is hydrogen atom, a straight or branched chain alkyl group having 1 to 6 carbon atoms, an alkoxy group having 1 to 4 carbon atoms, a halogen atom, hydroxyl group, trifluoromethyl group, nitro group or amino group; $R^2$ is a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group, 2-pyridyl group, 3-pyridyl group or 4-pyridyl group; each of $R^3$ and $R^4$ is independently hydrogen atom, a straight or branched chain alkyl group having 1 to 6 carbon atoms, a hydroxyalkyl group having 1 to 4 carbon atoms, a cycloalkyl group having 3 to 8 carbon atoms, or a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group; and Y is an alkylene group having 1 to 12 carbon atoms, comprising the step of preparing the piperadinesulfonamide derivative represented by the general formula (III) by the process according to item (1) above.

DETAILED DESCRIPTION OF THE INVENTION

As mentioned above, the process for preparing a piperazinesulfonamide derivative of the present invention is characterized by reacting a piperazine derivative represented by the general formula (I):

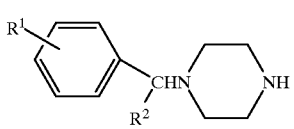

wherein $R^1$ is hydrogen atom, a straight or branched chain alkyl group having 1 to 6 carbon atoms, an alkoxy group having 1 to 4 carbon atoms, a halogen atom, hydroxyl group, trifluoromethyl group, nitro group or amino group; and $R^2$ is a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group, 2-pyridyl group, 3-pyridyl group or 4-pyridyl group, with a halogenoalkylsulfonamide derivative represented by the general formula (II):

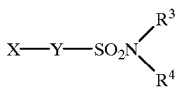

wherein each of $R^3$ and $R^4$ is independently hydrogen atom, a straight or branched chain alkyl group having 1 to 6 carbon atoms, a hydroxyalkyl group having 1 to 4 carbon atoms, a cycloalkyl group having 3 to 8 carbon atoms, or a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group; X is chlorine atom, bromine atom or iodine atom; and Y is an alkylene group having 1 to 12 carbon atoms, in the presence of an organic base and in the absence of a solvent.

In the piperazine derivative represented by the general formula (I), $R^1$ is hydrogen atom, a straight or branched chain alkyl group having 1 to 6 carbon atoms, an alkoxy group having 1 to 4 carbon atoms, a halogen atom, hydroxyl group, trifluoromethyl group, nitro group or amino group; and $R^2$ is a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group, 2-pyridyl group, 3-pyridyl group or 4-pyridyl group.

In $R^1$, the straight or branched chain alkyl group having 1 to 6 carbon atoms includes methyl group, ethyl group, n-propyl group, isopropyl group, n-butyl group, isobutyl group, sec-butyl group, tert-butyl group, n-pentyl group, isopentyl group, sec-pentyl group, neopentyl group, tert-pentyl group, n-hexyl group, isohexyl group, sec-hexyl group, neohexyl group and tert-hexyl group.

The alkoxy group having 1 to 4 carbon atoms includes methoxy group, ethoxy group, n-propoxy group, isopropoxy group, n-butoxy group, isobutoxy group, sec-butoxy group, tert-butoxy group, and the like.

The halogen atom includes fluorine atom, chlorine atom, bromine atom and iodine atom.

Among $R^1$, hydrogen atom, a straight or branched chain alkyl group having 1 to 4 carbon atoms, an alkoxy group having 1 to 4 carbon atoms, a halogen atom, hydroxyl group, trifluoromethyl group, nitro group or amino group is preferable, and hydrogen atom or a halogen atom is more preferable, and a halogen atom at meta-position or para-position is particularly preferable.

In $R^2$, as to the phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group, the alkyl group having 1 to 4 carbon atoms includes methyl group, ethyl group, n-propyl group, isopropyl group, n-butyl group, isobutyl group, sec-butyl group and tert-butyl group. The alkoxy group having 1 to 4 carbon atoms includes methoxy group, ethoxy group, propoxy group and butoxy group. The halogen atom includes fluorine atom, chlorine atom, bromine atom and iodine atom.

$R^2$ is preferably unsubstituted phenyl group, a phenyl group which may have as substituents on its phenyl ring 1 or 2 halogen atoms, 2-pyridyl group or 4-pyridyl group, more preferably unsubstituted phenyl group, a phenyl group which may have as a substituent on its phenyl ring one halogen atom, 2-pyridyl group or 4-pyridyl group, and particularly preferably unsubstituted phenyl group.

In addition, among the piperazine derivatives represented by the general formula (I), a compound in which $R^1$ is hydrogen atom, a straight or branched chain alkyl group having 1 to 4 carbon atoms, an alkoxy group having 1 to 4 carbon atoms, a halogen atom, hydroxyl group, trifluoromethyl group, nitro group or amino group; and $R^2$ is a phenyl group which may have as substituents on its phenyl ring 1 or 2 halogen atoms, 2-pyridyl group or 4-pyridyl group is preferable, from the viewpoint of obtaining a desired piperazinesulfonamide derivative represented by the general formula (III), and in particular a compound in which $R^1$ is hydrogen atom or a halogen atom and $R^2$ is unsubstituted phenyl or a phenyl group which may have as a substituent on its phenyl ring one halogen atom is more preferable.

Since the piperazine derivative represented by the general formula (I) has one asymmetric carbon in some cases, there exists an optical active form in the piperazine derivatives. In the piperazine derivative represented by the general formula (I) having optical activity, $R^1$ is hydrogen atom, a straight or branched chain alkyl group having 1 to 6 carbon atoms, an alkoxy group having 1 to 4 carbon atoms, a halogen atom, hydroxyl group, trifluoromethyl group, nitro group or amino group; and $R^2$ is a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group, 2-pyridyl group, 3-pyridyl group or 4-pyridyl group.

In $R^1$, the straight or branched chain alkyl group having 1 to 6 carbon atoms includes methyl group, ethyl group, n-propyl group, isopropyl group, n-butyl group, isobutyl group, sec-butyl group, tert-butyl group, Be n-pentyl group, isopentyl group, sec-pentyl group, neopentyl group, tert-pentyl group, n-hexyl group, isohexyl group, sec-hexyl group, neohexyl group and tert-hexyl group.

The alkoxy group having 1 to 4 carbon atoms includes methoxy group, ethoxy group, n-propoxy group, isopropoxy group, n-butoxy group, isobutoxy group, sec-butoxy group, tert-butoxy group, and the like.

The halogen atom includes fluorine atom, chlorine atom, bromine atom and iodine atom.

Among $R^1$, hydrogen atom, a straight or branched chain alkyl group having 1 to 4 carbon atoms, an alkoxy group having 1 to 4 carbon atoms, a halogen atom, hydroxyl group, trifluoromethyl group, nitro group or amino group is preferable, and hydrogen atom or a halogen atom is more preferable, and a halogen atom at meta-position or para-position is particularly preferable.

In $R^2$, as to the phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group, the alkyl group having 1 to 4 carbon atoms includes methyl group, ethyl group, n-propyl group, isopropyl group, n-butyl group, isobutyl group, sec-butyl group and tert-butyl group. The alkoxy group having 1 to 4 carbon atoms includes methoxy group, ethoxy group, propoxy group and butoxy group. The halogen atom includes fluorine atom, chlorine atom, bromine atom and iodine atom.

$R^2$ is preferably unsubstituted phenyl group, phenyl group which may have as substituents on its phenyl ring 1 or 2 halogen atoms, 2-pyridyl group or 4-pyridyl group, more preferably unsubstituted phenyl group, a phenyl group which may have as a substituent on its phenyl ring one halogen atom, 2-pyridyl group or 4-pyridyl group, and particularly preferably unsubstituted phenyl group.

In addition, among the piperazine derivatives represented by the general formula (I) having optical activity, a compound in which $R^1$ is hydrogen atom, a straight or branched chain alkyl group having 1 to 4 carbon atoms, an alkoxy group having 1 to 4 carbon atoms, a halogen atom, hydroxyl group, trifluoromethyl group, nitro group or amino group; and $R^2$ is a phenyl group which may have as substituents on its phenyl ring 1 or 2 halogen atoms, 2-pyridyl group or 4-pyridyl group is preferable, from the viewpoint of obtaining a desired piperazinesulfonamide derivative represented by the general formula (III) having pharmaceutically effective optical activity, and in particular a compound in which $R^1$ is hydrogen atom or a halogen atom and $R^2$ is unsubstituted phenyl or a phenyl group which may have as a substituent on its phenyl ring one halogen atom is more preferable.

Representative examples of the piperazine derivative represented by the general formula (I) include, for instance, 1-[(3-chlorophenyl)phenylmethyl]piperazine,
1-[(4-chlorophenyl)phenylmethyl]piperazine,
1-[bis(4-chlorophenyl)methyl]piperazine,
1-[bis(3-chlorophenyl)methyl]piperazine,
1-[bis(4-fluorophenyl)methyl]piperazine,
1-[4-chlorophenyl-(2-pyridyl)methyl]piperazine,
1-[4-fluorophenyl-(2-pyridyl)methyl]piperazine,
diphenylmethylpiperazine, 1-[4-fluorophenyl(3-pyridyl)methyl]piperazine,
1-[4-chlorophenyl(4-pyridyl)methyl]piperazine,
1-[phenyl(4-pyridyl)methyl]piperazine,
1-[(4-methoxyphenyl)phenylmethyl]piperazine,
1-[(2-fluorophenyl)phenylmethyl]piperazine,
1-[(4-methylphenyl)phenylmethyl]piperazine,
1-[(4-trifluoromethylphenyl)phenylmethyl]piperazine,
1-[(3-trifluoromethylphenyl)phenylmethyl]piperazine,
1-[(4-hydroxyphenyl)phenylmethyl]piperazine,
1-[(4-nitrophenyl)phenylmethyl]piperazine,
1-[(4-aminophenyl)phenylmethyl]piperazine,
1-[bis(2-chlorophenyl)methyl]piperazine,
1-[(3,4-dichlorophenyl)phenylmethyl]piperazine,
1-[(2-chorophenyl)phenylmethyl]piperazine,
(+)-1-[(3-chlorophenyl)phenylmethyl]piperazine,
(−)-1-[(3-chlorophenyl )phenylmethyl]piperazine,
(+)-1-[(4-chlorophenyl)phenylmethyl]piperazine,
(−)-1-[(4-chlorophenyl)phenylmethyl]piperazine,
(+)-1-[(4-chlorophenyl-(2-pyridyl)methyl]piperazine,
(−)-1-[(4-chlorophenyl-(2-pyridyl)methyl]piperazine,
(+) -1-[4-fluorophenyl-(2-pyridyl )methyl]piperazine,
1(−)-1-[4-fluorophenyl-(2-pyridyl)methyl]piperazine,
(+)-1-[4-fluorophenyl-(3-pyridyl)methyl]piperazine,
(−)-1-[4-fluorophenyl-(3-pyridyl )methyl]piperazine,
(+)-1-[4-chlorophenyl-(4-pyridyl)methyl]piperazine,
(−)-1-[4-chlorophenyl-(4-pyridyl)methyl]piperazine,
(+)-1-[phenyl-(4-pyridyl)methyl]piperazine,
(−)-1-[phenyl-(4-pyridyl)ethyl]piperazine,
(+)-1-[(4-methoxyphenyl)phenylmethyl]piperazine,
(−)-1-[(4-methoxyphenyl)phenylmethyl]piperazine,
(+)-1-[(2-fluorophenyl)phenylmethyl]piperazine,
(−)-1-[(2-fluorophenyl)phenylmethyl]piperazine,
(+)-1-[(4-methylphenyl)phenylmethyl]piperazine,
(−)-1-[(4-methylphenyl)phenylmethyl]piperazine,
(+)-1-[(4-trifluoromethylphenyl)phenylmethyl]piperazine,
(−)-1-[(4-trifluoromethylphenyl)phenylmethyl]piperazine,
(+)-1-[(3-trifluoromethylphenyl)phenylmethyl]piperazine,
(−) -1-[(3-trifluoromethylphenyl)phenylmethyl]piperazine,
(+)-1-[(4-hydroxyphenyl)phenylmethyl]piperazine,
(−)-1-[(4-hydroxyphenyl)phenylmethyl]piperazine,
(+)-1-[(4-nitrophenyl)phenylmethyl]piperazine,
(−)-1-[(4-nitrophenyl)phenylmethyl]piperazine,
(+)-1-[(4-aminophenyl)phenylmethyl]piperazine,
1(−)-1-[(4-aminophenyl)phenylmethyl]piperazine,
(+)--[(3,4-dichlorophenyl)phenylmethyl]piperazine,
(−)-1-[(3,4-dichlorophenyl)phenylmethyl]piperazine,
(+)-1-[(2-chlorophenyl)phenylmethyl]piperazine,
(−)-1-[(2-chorophenyl )phenylmethyl]piperazine,
(+)-1-[(4-fluorophenyl)phenylmethyl)piperazine,
(−)-1-[(4-fluorophenyl)phenylmethyl]piperazine,
(+)-1-[(3-fluorophenyl)phenylmethyl]piperazine,
(−)-1-[(3-fluorophenyl)phenylmethyl]piperazine,
1-[(3-fluorophenyl)phenylmethyl]piperazine,
1-[(4-fluorophenyl)phenylmethyl]piperazine, and the like,
without intending to limit the present invention thereto.

The piperazine derivative represented by the general formula (I) can be obtained by a method described, for instance, in *Journal of Pharmaceutical Science* 67, 900, 1978, Japanese Patent Laid-Open No. 2816/1995, or the like.

In the halogenoalkylsulfonamide derivative represented by the general formula (II), each of $R^3$ and $R^4$ is independently hydrogen atom, a straight or branched chain alkyl group having 1 to 6 carbon atoms, a hydroxyalkyl group having 1 to 4 carbon atoms, a cycloalkyl group having 3 to 8 carbon atoms, or a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group; X is chlorine atom, bromine atom or iodine atom; and Y is an alkylene group having 1 to 12 carbon atoms.

In each of $R^3$ and $R^4$, the straight or branched chain alkyl group having 1 to 6 carbon atoms includes methyl group, ethyl group, n-propyl group, isopropyl group, n-butyl group, isobutyl group, sec-butyl group, tert-butyl group, n-pentyl group, isopentyl group, sec-pentyl group, neopentyl group, tert-pentyl group, n-hexyl group, isohexyl group, sec-hexyl group, neohexyl group and tert-hexyl group. The hydroxyalkyl group having 1 to 4 carbon atoms includes hydroxymethyl group, hydroxyethyl group, hydroxypropyl group and hydroxybutyl group. The cycloalkyl group having 3 to 8 carbon atoms includes cyclopropyl group, cyclobutyl group, cyclopentyl group, cyclohexyl group, cycloheptyl group and cyclooctyl group. In the phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group, the alkyl group having 1 to 4 carbon atoms includes methyl group, ethyl group, n-propyl group, isopropyl group, n-butyl group, isobutyl group, sec-butyl group and tert-butyl group. The alkoxy group having 1 to 4 carbon atoms includes methoxy group, ethoxy group, propoxy group and butoxy group. The halogen atom includes fluorine atom, chlorine atom, bromine atom and iodine atom.

Each of R and $R^4$ is preferably hydrogen atom, a straight or branched chain alkyl group having 1 to 6 carbon atoms, a hydroxyalkyl group having 1 to 4 carbon atoms, and a cycloalkyl group having 3 to 8 carbon atoms, more preferably hydrogen atom, a straight or branched chain alkyl group having 1 to 6 carbon atoms, a hydroxyalkyl group having 1 to 4 carbon atoms, and a cycloalkyl group having 3 to 6 carbon atoms. In addition, it is particularly preferable that each of these $R^3$ and $R^4$ is a straight or branched chain alkyl group having 1 to 6 carbon atoms, or $R^4$ is hydrogen atom.

In the present invention, from the viewpoint of preparing a piperazinesulfonamide derivative having excellent pharmacological activity, a preferable combination of $R^3$ and $R^4$ is a combination of $R^3$ and $R^4$ where $R^3$ is a straight or branched chain alkyl group having 1 to 6 carbon atoms, a hydroxyalkyl group having 1 to 4 carbon atoms, a cycloalkyl group having 3 to 8 carbon atoms, or a phenyl group which may have as substituents on its phenyl ring 1 to 3 groups selected from the group consisting of hydroxyl group and an alkoxy group having 1 to 4 carbon atoms and $R^4$ is hydrogen atom; or a combination of $R^3$ and $R^4$ where each of $R^3$ and $R^4$ is a straight or branched chain alkyl group having 1 to 6 carbon atoms. More preferably, the number of carbon atoms of the cycloalkyl group is 3 to 6, and the substituents on its phenyl ring are three alkoxy groups having 1 to 4 carbon atoms. Among these combinations of $R^3$ and $R^4$, more preferable are a combination where $R^3$ is a hydroxyalkyl group having 1 to 4 carbon atoms, and $R^4$ is hydrogen atom; a combination where $R^3$ is a cycloalkyl group having 3 to 6 carbon atoms, and $R^4$ is hydrogen atom; a combination where each of $R^3$ and $R^4$ is methyl group; a combination where each of $R^3$ and $R^4$ is ethyl group; and a combination where $R^3$ is cyclopropyl group, cyclobutyl group or a hydroxyalkyl group having 1 to 4 carbon atoms, and $R^4$ is hydrogen atom.

As described above, X is chlorine atom, bromine atom or iodine atom.

As described above, Y is an alkylene group having 1 to 12 carbon atoms, preferably 5 to 12 carbon atoms, more preferably 5 to 8 carbon atoms. The alkylene group may be a straight or branched chain.

Among the halogenoalkylsulfonamide derivatives represented by the general formula (II), from the viewpoint of preparing a pharmacologically effective piperazinesulfonamide derivative, particularly preferable ones are a halogenoalkylsulfonamide derivative wherein each of $R^3$ and $R^4$ is independently hydrogen atom, a straight or branched chain alkyl group having 1 to 6 carbon atoms, a hydroxyalkyl group having 1 to 4 carbon atoms, a cycloalkyl group having 3 to 6 carbon atoms; X is chlorine atom, bromine atom or iodine atom; and Y is an alkylene group having 1 to 12 carbon atoms.

Representative examples of the halogenoalkylsulfonamide derivative represented by the general formula (II) include 6-chlorohexanesulfonamide,
N-cyclopropyl-6-chlorohexanesulfonamide,
N-cyclopropyl-6-bromohexanesulfonamide,
N-methyl-6-chlorohexanesulfonamide,
N,N-dimethyl-6-chlorohexanesulfonamide,
N-ethyl-6-chlorohexanesulfonamide,
N,N-diethyl-6-chlorohexanesulfonamide,
N-n-propyl-6-chlorohexanesulfonamide,
N-isopropyl-6-chlorohexanesulfonamide,
N-n-butyl-6-chlorohexanesulfonamide,
N-tert-butyl-6-chlorohexanesulfonamide,
N-n-pentyl-6-chlorohexanesul fonamide,
N-n-hexyl-6-chlorohexanesulfonamide,
N-cyclobutyl-6-chlorohexanesulfonamide,
N-cyclopentyl-6-chlorohexanesulfonamide,
N-cyclohexyl-6-chlorohexanesulfonamide,
N-cyclopropyl-5-bromopentanesul fonamide,
N-cyclopropyl-6-bromohexanesulfonamide,
N-cyclopropyl-7-bromoheptanesulfonamide,
N-cyclopropyl-8-bromooctanesulfonamide,
N-cyclopropyl-6-Iodohexanesulfonamide,
N-cyclopropyl-9-chlorononanesulfonamide,
N-cyclopropyl-10-bromodecanesulfonamide,
N-cyclopropyl-11-bromoundecanesulfonamide,
N-cyclopropyl-12-bromododecanesulfonamide,
N-(2-hydroxyethyl)bromomethanesulfonamide,
N-(2-hydroxyethyl)-2-chloroethanesulfonamide,
N-(2-hydroxyethyl)-3-chloropropanesulfonamide,
N-(2-hydroxyethyl)-4-chlorobutanesulfonamide,
N-(2-hydroxyethyl)-5-chloropentanesulfonamide,
N-(2-hydroxyethyl)-6-chlorohexanesulfonamide,
N-(2-hydroxyethyl)-7-chloroheptanesulfonamide,
N-(2-hydroxyethyl)-8-chlorooctanesulfonamide,
N-(2-hydroxyethyl)-9-chlorononanesulfonamide,
N-(2-hydroxyethyl)-10-bromodecanesulfonamide,
N-(2-hydroxyethyl)11brmoundecanesulfonamide, N-(2-hydroxyethyl)-12-bromododecanesulfonamide,
N-(3-hydroxypropyl)-5-chloropentanesulfonamide,
N-(4-hydroxybutyl)-5-chloropentanesulfonamide,
N-(3-hydroxypropyl)-6-chlorohexanesulfonamide,
N,N-(4-hydroxybutyl)-6-chlorohexanesulfonamide,
N,N-dimethylchloromethanesulfonamide,
N,N-dimethyl-2-chloroethanesulfonamide,
N,N-dimethyl-3-chloropropanesulfonamnide,
N,N-dimnethyl-4-chlorobutanesulfonamide,
N,N-dimethyl-5-chloropentanesulfonamide,
N,N-dimethyl-7-chloroheptanesulfonamiide,
N,N-dimethyl-8-chlorooctanesulfonamide,
N,N-dimethyl-9-chlorononanesulfonamide,
N,N-dimethyl-10-bromodecanesulfonamide,
N,N-dimethyl-11-bromoundecanesulfonamide,
N,N-dimethyl-12-bromododecanesulfonamide,
N,N-diethyl-5-chloropentanesulfonamide,
N,N-di-n-propyl-5-chloropentanesulfonamide,
N,N-di-n-butyl-5-chloropentanesulfonamide,
N,N-di-n-propyl-6-chlorohexanesulfonamide,
N,N-di-n-butyl-6-chlorohexanesulfonamide,
N-n-butyl-N-methyl-5-chloropentanesulfonamide,
N-n-butyl-N-methyl-6-chlorohexanesulfonamide,
and the like, but the present invention is by no means limited to these compounds.

In the process for preparing the halogenoalkylsulfonamide derivative represented by the general formula (II), a process for preparing a halogenoalkylsulfonamide derivative wherein each of $R^3$ and $R^4$ is hydrogen atom in the general formula (II) is different from that for preparing a halogenoalkylsulfonamide derivative wherein $R^3$ and $R^4$ are not simultaneously hydrogen atoms in the general formula (II).

The halogenoalkylsulfonamide derivative wherein each of $R^3$ and $R^4$ is hydrogen atom can be prepared, for instance, by a process disclosed in *The Journal of Organic Chemistry* 52, 2162, 1987, or the like.

In addition, in the processes for preparing a halogenoalkylsulfonamide derivative wherein $R^3$ and $R^4$ are not simultaneously hydrogen atoms, a process for preparing a halogenoalkylsulfonamide derivative represented by the general formula (IIa):

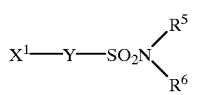
(IIa)

wherein $R^5$ is hydrogen atom, a straight or branched chain alkyl group having 1 to 6 carbon atoms, a hydroxyalkyl group having 1 to 4 carbon atoms, a cycloalkyl group having 3 to 8 carbon atoms, or a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group; $R^6$ is a straight or branched chain alkyl group having 1 to 6 carbon atoms, a hydroxyalkyl group having 1 to 4 carbon atoms, a cycloalkyl group having 3 to 8 carbon atoms, or a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group; $X^1$ is chlorine atom or bromine atom; and Y is the same as Y in the general formula (II), which is a compound wherein X is chlorine atom or bromine atom in the general formula (II), is different from that for preparing a halogenoalkylsulfonamide derivative represented by the general formula (IIb):

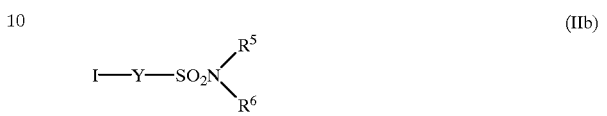
(IIb)

wherein $R^5$, $R^6$ and Y are as defined above, which is a compound wherein X is iodine atom in the general formula (II).

First, a process for preparing a halogenoalkylsulfonamide derivative represented by the general formula (IIa) will be described.

The halogenoalkylsulfonamide derivative represented by the general formula (IIa) can be obtained by reacting a halogenoalkylsulfonyl chloride represented by the general formula (IV):

(IV)

wherein $X^1$ and Y are as defined above, with an amine represented by the general formula (V):

(V)

wherein $R^5$ and $R^6$ are as defined above, in the presence or absence of a base in a solvent or without a solvent.

As the halogenoalkylsulfonyl chloride represented by the general formula (IV), there can be cited a halogenoalkylsulfonyl chloride represented by the general formula (IVa):

(IVa)

wherein Y is as defined above; and a halogenoalkylsulfonyl chloride represented by the general formula (IVb):

(IVb)

wherein Y is as defined above.

In the general formula (IVa), Y is preferably an alkylene group having 5 to 12 carbon atoms.

The halogenoalkylsulfonyl chloride represented by the general formula (IVa) is concretely a bromoalkylsulfonyl chloride.

Representative examples of the halogenoalkylsulfonyl chloride represented by the general formula (IVa) include 5-bromopentanesulfonyl chloride, 6-bromohexanesulfonyl chloride, 7-bromoheptanesulfonyl chloride, 8-bromooctanesulfonyl chloride, 2-bromohexanesulfonyl chloride, 3-bromohexanesulfonyl chloride, 5-bromohexanesulfonyl chloride, bromomethylenesulfonyl chloride, 2-bromoethanesulfonyl chloride, 3-bromopropanesulfonyl chloride, 4-bromobutanesulfonyl chloride, 9-bromononanesulfonyl chloride, 10-bromodecanesulfonyl chloride, 11-bromoundecanesulfonyl chloride and 12-bromododecanesulfonyl chloride.

The process for preparing the halogenoalkylsulfonyl chloride represented by the general formula (IVa) will be described in detail in a later section.

The halogenoalkylsulfonyl chloride represented by the general formula (IVb) is concretely a chloroalkylsulfonyl chloride.

Representative examples of the halogenoalkylsulfonyl chloride represented by the general formula (IVb) include 5-chloropentanesulfonyl chloride, 6-chlorohexanesulfonyl chloride, 7-chloroheptanesulfonyl chloride, 8-chlorooctanesulfonyl chloride, 2-chlorohexanesulfonyl chloride, 3-chlorohexanesulfonyl chloride, 5-chlorohexanesulfonyl chloride, chloromethanesulfonyl chloride, 2-chloroethanesulfonyl chloride, 3-chloropropanesulfonyl chloride, 4-chlorobutanesulfonyl chloride, 9-chlorononanesulfonyl chloride, 10-chlorodecanesulfonyl chloride, 11-chloroundecanesulfonyl chloride and 12-chlorododecanesulfonyl chloride.

In the amine represented by the general formula (V), $R^5$ is hydrogen atom, a straight or branched chain alkyl group having 1 to 6 carbon atoms, a hydroxyalkyl group having 1 to 4 carbon atoms, a cycloalkyl group having 3 to 8 carbon atoms, or a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group; and $R^6$ is a straight or branched chain alkyl group having 1 to 6 carbon atoms, a hydroxyalkyl group having 1 to 4 carbon atoms, a cycloalkyl group having 3 to 8 carbon atoms, or a phenyl group which may have as substituents on its phenyl ring 1 to 3 groups selected from the group consisting of an alkyl group having 1 to 6 carbon atoms, an alkoxy group having 1 to 4 carbon atoms, a halogen atom, hydroxyl group, trifluoromethyl group, nitro group and amino group.

Among the amines represented by the general formula (V), from the viewpoint of obtaining a desired halogenoalkylsulfonamide derivative represented by the general formula (II), preferable ones are an amine wherein $R^5$ is hydrogen atom, and $R^6$ is a straight or branched chain alkyl group having 1 to 6 carbon atoms, a hydroxyalkyl group having 1 to 4 carbon atoms, a cycloalkyl group having 3 to 8 carbon atoms, or a phenyl group which may have as substituents on its phenyl ring 1 to 3 groups selected from the group consisting of hydroxyl group and an alkoxy group having 1 to 4 carbon atoms; and an amine wherein each of $R^5$ and $R^6$ is an alkyl group having 1 to 4 carbon atoms. The number of carbon atoms of the cycloalkyl group is more preferably 3 to 6, and the substituents on the phenyl ring are more preferably three alkoxy groups having 1 to 4 carbon atoms.

As representative examples of the amine represented by the general formula (V), preferable ones are primary amines such as methylamine, ethylamine, n-propylamine, isopropylamine, n-butylamine, isobutylamine, sec-butylamine, tert-butylamine, n-pentylamine, isopentylamine, sec-pentylamine, neopentylamine, tert-pentylamine, n-hexylamine, isohexylamine, sec-hexylamine, neohexylamine, tert-hexylamine, cyclopropylamine, cyclobutylamine, cyclopentylamine, cyclohexylamine, hydroxymethylamine, hydroxyethylamine, hydroxypropylamine, hydroxybutylamine and aniline; and secondary amines such as dimethylamine, diethylamine, dipropylamine, dibutylamine and butylmethylamine. More preferable ones are cyclopropylamine, cyclobutylamine, cyclopentylamine, cyclohexylamine, hydroxyethylamine, hydroxypropylamine, hydroxybutylamine, dimethylamine and diethylamine. Still more preferable ones are cyclopropylamine, cyclobutylamine, hydroxyethylamine, hydroxypropylamine, dimethylamine and diethylamine. Particularly preferable ones are cyclopropylamine, hydroxyethylamine, hydroxypropylamine, dimethylamine and diethylamine.

As described above, the halogenoalkylsulfonamide derivative represented by the general formula (IIa) can be obtained by reacting a halogenoalkylsulfonyl chloride represented by the general formula (IV) with an amine represented by the general formula (V) in the presence or absence of a base in a solvent or without a solvent.

It is preferable that the amount of the amine represented by the general formula (V) is generally 2 to 4 mol per one mol of the halogenoalkylsulfonyl chloride when the reaction is carried out in the absence of an inorganic base, and that the amount of the amine is 1 to 3 mol per one mol of the halogenoalkylsulfonyl chloride when the reaction is carried out in the presence of an inorganic base.

More strictly, when the reaction is carried out in the absence of an inorganic base, the amount of the amine differs depending upon the kinds of the amines. When the amine has one hydroxyalkyl group, it is desired that the amount of the amine is 2 to 3.3 mol per one mol of the halogenoalkylsulfonyl chloride. When the amine has two hydroxyalkyl groups, it is desired that the amount of the amine is 2 to 4 mol per one mol of the halogenoalkylsulfonyl chloride. In addition, when the amine has no hydroxyalkyl group, it is desired that the amount of the amine is 2 to 2.2 mol per one mol of the halogenoalkylsulfonyl chloride.

When the reaction is carried out in the presence of an inorganic base, the inorganic base includes, for instance, alkali metal hydroxides such as lithium hydroxide, sodium hydroxide and potassium hydroxide, sodium hydrogencarbonate, potassium hydrogencarbonate, sodium carbonate, potassium carbonate, and the like. Among them, alkali metal hydroxides such as lithium hydroxide, sodium hydroxide and potassium hydroxide are preferable.

It is desired that the amount of the inorganic base is not less than one mol per one mol of the halogenoalkylsulfonyl chloride, from the viewpoint of sufficient reduction of the amount of the amine, and that the amount of the inorganic base is at most 1.5 mol, preferably at most 1.2 mol, from the viewpoint of avoidance of the influence of hydrolysis.

When the inorganic base is used in the above amount, the amount of the amine differs depending upon the kinds of the amines. When the amine has one hydroxyalkyl group, it is desired that the amount of the amine is 1 to 1.5 mol per one mol of the halogenoalkylsulfonyl chloride. When the amine has two hydroxyalkyl groups, it is desired that the amount of the amine is 1 to 3 mol per one mol of the halogenoalkylsulfonyl chloride. In addition, when the amine has no hydroxyalkyl group, it is desired that the amount of the amine is 1 to 1.2 mol per one mol of the halogenoalkylsulfonyl chloride.

In the present invention, in the course of reaction, when the reaction is carried out in the presence of the inorganic base as described above, there is an advantage that the amount of the relatively expensive amine represented by the general formula (V) can be reduced. Furthermore, since the inorganic base is used, the resulting product can be easily separated from the inorganic base after the conclusion of the reaction. Accordingly, there is an advantage that complicated procedures are not required as in the case where an organic base is used.

In the present invention, an organic base, such as pyridine, triethylamine, diisobutylethylamine, N-ethyldiisopropylamine, 4-N,N-dimethylaminopyridine, 1,8-diazabicyclo[5,4,0]-7-undecene or 1,4-diazabicyclo[2,2,2]octane, may be contained within the scope which would not hinder the object of the present invention.

In the course of reaction, a solvent can be used. The solvent may be any one as long as the reaction is not hindered. Representative examples of the solvent include, for instance, diethyl ether, diisopropyl ether, tetrahydrofuran, dioxane, dimethoxyethane, dichloromethane, chloroform, benzene, toluene, xylene, acetonitrile, acetone, methyl ethyl ketone, ethyl acetate, hydrous solvents thereof, water, and the like. Among them, from the viewpoint of industrial productivity, water can be favorably used.

When the reaction is carried out in the absence of the inorganic base, the halogenoalkylsulfonyl chloride can be reacted with the amine represented by the general formula (V), for instance, by adding the halogenoalkylsulfonyl chloride dropwise with stirring to the amine dissolved in a solvent or to the amine without a solvent, or by adding dropwise the amine with stirring under ice-cooling to the halogenoalkylsulfonyl chloride dissolved in a solvent or to the halogenoalkylsulfonyl chloride without a solvent. Alternatively, when the reaction is carried out in the presence of the inorganic base, the reaction may be carried out, for instance, by mixing the halogenoalkylsulfonyl chloride with a solvent, adding thereto an inorganic base under ice-cooling, and thereafter adding thereto the amine dropwise with stirring, or by mixing the amine with a solvent, adding thereto the base under ice-cooling, and thereafter adding thereto the halogenoalkylsulfonyl chloride dropwise with stirring.

The atmosphere in the course of reaction is not limited to specified ones, and it may be air or an inert gas atmosphere such as nitrogen gas. The temperature inside the reaction system may be usually a temperature ranging from 0° C. to the boiling point of the solvent.

The conclusion of reaction can be regarded as a point at which the starting materials disappeared when observed, for instance, by thin layer chromatography.

After the conclusion of reaction, the resulting reaction mixture is washed with, for instance, water, brine, or the like, and dried over, for instance, anhydrous magnesium sulfate, or the like, and the filtrate is concentrated in vacuo, to give a crude product. The halogenoalkylsulfonamide derivative represented by the general formula (IIa) can be obtained by purifying the crude product by means of, for instance, silica gel column chromatography, recrystallization, or the like.

When water is used as a solvent, the reaction mixture obtained after the conclusion of reaction is extracted with, for instance, diethyl ether, chloroform, ethyl acetate, or the like, and thereafter the same procedures as above can be carried out.

Next, the process for preparing the halogenoalkylsulfonamide derivative represented by the general formula (IIb) will be described.

The halogenoalkylsulfonamide derivative represented by the general formula (IIb) can be obtained by reacting the halogenoalkylsulfonamide derivative represented by the general formula (IIa) with sodium iodide.

In the course of reaction, a solvent can be used. As the solvent, any ones can be used as long as the reaction is not hindered. There can be cited, for instance, methyl ethyl ketone, acetone, and the like.

The halogenoalkylsulfonamide derivative represented by the general formula (IIa) is dissolved in a solvent, and thereafter sodium iodide is added.

It is desired that the amount of sodium iodide is usually 1 to 3 mol, preferably about 2 mol, per one mol of the halogenoalkylsulfonamide derivative represented by the general formula (IIa).

After sodium iodide is added and dissolved therein, the resulting solution is heated to a temperature of room temperature to the boiling point of the solvent.

The heating time is not limited to specified ones, and heating can be carried out until the conclusion of the reaction.

The conclusion of the reaction can be regarded as a point at which the starting materials disappeared when observed, for instance, by thin layer chromatography.

After the conclusion of the reaction, the resulting reaction mixture is washed with, for instance, water, brine, and the like, and dried over, for instance, anhydrous magnesium sulfate, or the like, and thereafter the filtrate is concentrated in vacuo, to give a crude product. The halogenoalkylsulfonamide derivative represented by the general formula (IIb) can be obtained by purifying the crude product by means of, for instance, silica gel column chromatography, recrystallization, or the like.

Next, the process for preparing the halogenoalkylsulfonyl chloride represented by the general formula (IVa) will be described.

The halogenoalkylsulfonyl chloride represented by the general formula (IVa) can be obtained by reacting a sodium bromoalkylsulfonate represented by the general formula (VI):

$$Br—Y—SO_3Na \qquad\qquad (VI)$$

wherein Y is as defined above, with a chlorinating agent.

Examples of the sodium bromoalkylsulfonate represented by the general formula (VI) include sodium 5-bromopentanesulfonate, sodium 6-bromohexanesulfonate, sodium 7-bromoheptanesulfonate, sodium 8-bromooctanesulfonate, sodium 2-bromohexanesulfonate, sodium 3-bromohexanesulfonate, sodium 5-bromohexanesulfonate, sodium bromomethanesulfonate, sodium 2-bromoethanesulfonate, sodium 3-bromopropanesulfonate, sodium 4-bromobutanesulfonate, sodium 9-bromononanesulfonate, sodium 10-bromodecanesulfonate, sodium 11-bromoundecanesulfonate and sodium 12-bromododecanesulfonate.

The sodium bromoalkylsulfonate represented by the general formula (VI) can be obtained by known methods (*Org. Synth.*, Coll. Vol. II, 558; WO95/19345 Pamphlet).

As the chlorinating agent used in the course of reaction, there can be cited, for instance, phosphorus pentachloride, phosphorus trichloride, phosphorus oxychloride, chlorosulfonic acid, sulfuryl chloride, thionyl chloride, phosgene, oxalyl chloride, and the like.

When the sodium bromoalkylsulfonate represented by the general formula (VI) is reacted with the chlorinating agent, a catalyst can be used.

As the catalyst, there can be cited, for instance N,N-dimethylformamide, or the like.

In the course of reaction, the solution may be heated to room temperature to 150° C. or so. The heating time is not limited to specified ones, and it may be a period until which the reaction is finished.

After the conclusion of reaction, the resulting reaction solution is washed with, for instance, water, brine and the like, dried over, for instance, calcium chloride or the like, and thereafter the filtrate is concentrated in vacuo, to give the halogenoalkylsulfonyl chloride represented by the general formula (IVa).

As described above, the piperazinesulfonamide derivative represented by the general formula (III) can be obtained by reacting the piperazine derivative represented by the general formula (I) with the halogenoalkylsulfonamide derivative represented by the general formula (II) in the presence of an organic base and in the absence of a solvent.

In the present invention, one of the features of the present invention resides in that the piperazine derivative represented by the general formula (I) is reacted with the halogenoalkylsulfonamide derivative represented by the general formula (II) when the organic base is used without a solvent. The desired piperazinesulfonamide derivative represented by the general formula (III) can be prepared within a surprisingly remarkably shortened reaction time and at high yield as compared with the case where a solvent is used. In the present invention, although some of the organic bases themselves simultaneously act as a solvent, the term "in the absence of a solvent" described in the present specification means that a solvent, such as water or an organic solvent, which has been used in a general meaning, is not used, separately from the organic base.

The organic base includes, for instance, pyridine, 2,4,6-trimethylpyridine, triethylamine, diisobutylethylamine, N-ethyldiisopropylamine, 4-N,N-dimethylaminopyridine, N-ethylmorpholine, 1,8-diazabicyclo[5,4,0]-7-undecene, 1,4-diazabicyclo[2,2,2]octane, and the like. These organic bases can be used alone or in admixture of two or more kinds. Among these organic bases, N-ethyldiisopropylamine, N-ethylmorpholine, triethylamine and 2,4,6-trimethylpyridine are preferable, and N-ethyldiisopropylamine and triethylamine are more preferable.

The amount of the organic base is preferably at least one mol per one mol of the piperazine derivative represented by the general formula (I) in order to obtain the desired product in a short period of time and at high yield.

It is desired that the amount of the halogenoalkylsulfonamide derivative represented by the general formula (II) is at least one mol, preferably 1 to 1.2 mol, per one mol of the piperazine derivative represented by the general formula (I).

The reaction can be carried out by, for instance, refluxing the piperazine derivative represented by the general formula (I) and the halogenoalkylsulfonamide derivative represented by the general formula (II) in the presence of the organic base.

The atmosphere in the course of reaction is not limited to specified ones, and it may be air or an inert gas atmosphere, for instance, nitrogen gas. The temperature in the reaction system may be usually within the range of room temperature to a boiling point of the organic base used or so. The reaction time differs depending on the reaction conditions, and it is desired that the reaction time is usually 0.5 to 8.0 hours or so, preferably 2 to 6 hours so that the reaction time can be remarkably shortened as compared with the case where the solvent is used as described above.

The conclusion of the reaction can be regarded as a point at which the starting materials disappeared when observed, for instance, by thin layer chromatography.

After the conclusion of the reaction, a crude product can be obtained by, for instance, concentrating the resulting reaction mixture in vacuo, adding water to the concentrate, extracting the mixture with chloroform, washing the chloroform layer with water, drying over anhydrous magnesium sulfate, and thereafter removing the solvent by evaporation in vacuo. The piperazinesulfonamide derivative represented by the general formula (III):

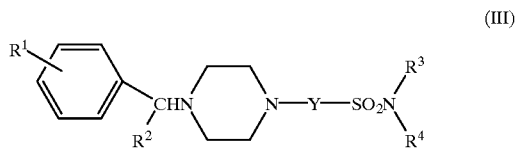

wherein $R^1$, $R^2$, $R^3$, $R^4$ and Y are as defined above, can be obtained by purifying the crude product by means of, for instance, silica gel column chromatography, recrystallization, or the like.

According to the process of the present invention, the piperazinesulfonamide derivative represented by the general formula (III) can be industrially advantageously obtained in a short period of time and at high yield.

Since some of the piperazinesulfonamide derivatives represented by the general formula (III) have one asymmetric carbon atom, its optical isomer exists therein. The present invention encompasses these steric isomers and mixtures thereof.

In addition, the piperazinesulfonamide derivative represented by the general formula (III) can be further formed into a salt by a conventional method. The pharmaceutically acceptable salts include acid addition salts and alkali addition salts. The acid addition salt includes, for instance, inorganic acid salts such as hydrochloric acid salts, hydrobromic acid salts, hydroiodic acid salts, sulfuric acid salts, nitric acid salts and phosphoric acid salts; and organic acid salts such as acetic acid salts, oxalic acid salts, maleic acid salts, fumaric acid salts, lactic acid salts, malic acid salts, citric acid salts, tartaric acid salts, methanesulfonic acid salts, ethanesulfonic acid salts and benzenesulfonic acid salts. The alkali addition salt includes, for instance, salts of alkali metal or alkaline earth metals such as sodium, potassium and calcium, ammonium salts, or salts of organic bases such as methylamine, ethylamine, dimethylamine, triethylamine, ethanolamine and piperidine.

EXAMPLES

Next, the present invention will be described in further detail on the basis of the working examples, without intending to limit the scope of the present invention only to these examples.

Preparation Example 1

Preparation of N-Cyclopropyl-6-chlorohexanesulfonamide

1 M-Aqueous sodium hydroxide (3.0 ml, 3.0 mmol) was added to a liquid mixture of 6-chlorohexanesulfonyl chloride (657 mg, 3.0 mmol) synthesized referring to the literatures of *Bull. Soc. Chim. Belges.*, 74, 21 (1965) and *J. Org. Chem.*, 52, 2162 (1987) and water (9 ml) under ice-cooling. Cyclopropylamine (206 mg, 3.6 mmol) was added dropwise thereto with stirring. Thereafter, the mixture was stirred at the same temperature for 1.5 hours. The mixture was diluted with diethyl ether (30 ml), and an organic layer was collected. The extract was washed with water and brine, and thereafter dried over anhydrous magnesium sulfate.

Subsequently, the solvent was removed by evaporation in vacuo. The crude product was purified by column chromatography on silica gel with chloroform, to give N-cyclopropyl-6-chlorohexanesulfonamide (588 mg) as colorless crystals.

(1) Melting Point: 38°–39° C. (diethyl ether)
(2) IR vmax (KBr) cm$^{-1}$: 3267 (NH), 1317, 1135 (SO$_2$)
(3) Mass Spectroscopy (C$_9$H$_{18}$ClNO$_2$S) EI: m/z 239 [M]$^+$
(4) EI-HRMS (C$_9$H$_{18}$ClNO$_2$S)
  Calculated: 239.0745, Found: 239.0746
(5) $^1$H-NMR (CDCl$_3$) δ: 0.64–0.78 (4H, m, CHCH$_2$x2), 1.43–1.58 (4H, m, ClCH$_2$CH$_2$CH$_2$CH$_2$), 1.72–1.89 (4H, m, ClCH$_2$CH$_2$, SCH$_2$CH$_2$), 2.54–2.61 (1H, m, CH), 3.06–3.11 (2H, m, SCH$_2$), 3.55 (2H, t, J=6.5 Hz, ClCH$_2$), 4.79 (1H, brs, NH)
(6) Elemental Analysis (C$_9$H$_{18}$ClNO$_2$S)
  Calculated: C, 45.08; H, 7.57; N, 5.84
  Found: C, 44.82; H, 7.50; N, 5.88

Preparation Example 2

Preparation of 6-Bromohexanesulfonyl Chloride

Thionyl chloride (10.3 ml, 140.4 mmol) and N,N-dimethylformamide (one drop) were added to sodium 6-bromohexanesulfonate (5.00 g, 18.7 mmol) prepared by a process described in Org. Synth., Coll. Vol. II, 558 or WO95/19345 Pamphlet. The mixture was refluxed for 4 hours. The reaction mixture was concentrated in vacuo. The concentrate was diluted with benzene (50 ml). The resulting solution was washed twice with water (15 ml) and then with brine (10 ml), and thereafter dried over calcium chloride. The solvent was removed by evaporation in vacuo. Crude 6-bromohexanesulfonyl chloride (1.61 g) was obtained as a pale yellow oil.

(1) IR vmax (neat) cm$^1$: 1360, 1160 (SO$_2$)
(2) Mass Spectroscopy (C$_6$H$_{12}$BrClO$_2$S) EI: m/z 263 [M+1]$^+$, CI: m/z 263 [M+1]$^+$
(3) EI-HRMS (C$_6$H$_{12}$BrClO$_2$S+H$^+$)
  Calculated: 262.9508, Found: 262.9509
(4) $^1$H-NMR (CDCl$_3$) δ: 1.56 (4H, m, CH$_2$x2), 1.92 (2H, m, BrCH$_2$CH$_2$), 2.09 (2H, m, SCH$_2$CH$_2$), 3.43 (2H, t, J=6.6 Hz, BrCH$_2$), 3.69 (2H, t, J=7.8 Hz, SCH$_2$)

Preparation Example 3

Preparation of N-Cyclopropyl-6-Bromohexanesulfonamide

6-Bromohexanesulfonyl chloride (1.78 g, 6.78 mmol) obtained in Preparation Example 2 was added dropwise to a solution of diethyl ether (10 ml) and cyclopropylamine (774 mg, 13.56 mmol), with stirring under ice-cooling. Thereafter, the mixture was stirred at the same temperature for 20 minutes. The reaction mixture was washed twice with water (10 ml) and then with brine (10 ml), and thereafter dried over anhydrous magnesium sulfate.

Subsequently, the solvent was removed by evaporation in vacuo. The crude product was purified by column chromatography on silica gel with ethyl acetate-n-hexane (1:4)–(1:3), to give N-cyclopropyl-6-bromohexanesulfonamide (1.52 g) as a colorless waxy product.

(1) IR vmax (neat) cm$^{-1}$: 3250 (NH), 1310, 1140 (SO$_2$)
(2) Mass Spectroscopy (C$_9$H$_{18}$BrNO$_2$S) EI: m/z 283 [M]$^+$
(3) EI-HRMS (C$_9$H$_{18}$BrNO$_2$S)
  Calculated: 283.0240, Found: 283.0246
(4) $^1$H-NMR (CDCl$_3$) δ: 0.65–0.79 (4H, m, CHCH$_2$x2), 1.51 (4H, m, BrCH$_2$CH$_2$CH$_2$CH$_2$), 1.75–1.94 (4H, m, BrCH$_2$CH$_2$, SCH$_2$CH$_2$), 2.56–2.62 (1H, m, CH), 3.07–3.12 (2H, m, SCH$_2$), 3.43 (2H, t, J=6.7 Hz, BrCH$_2$), 4.66 (1H, brs, NH)

Preparation Example 4

Preparation of N-(2-Hydroxyethyl)6-chlorohexanesulfonamide

A diethyl ether solution (15 ml) of 6-chlorohexanesulfonyl chloride (3.29 g, 15 mmol) was added dropwise to a suspension of diethyl ether (15 ml) and ethanolamine (2.02 g, 33 mmol) under ice-cooling. Thereafter, the mixture was stirred at room temperature for 1 hour. Water was added to the reaction mixture. The resulting solution was extracted with ethyl acetate (50 ml). The extract was dried over anhydrous magnesium sulfate. Subsequently, the solvent was removed by evaporation in vacuo. The crude product was purified by column chromatography on silica gel with chloroform-methanol (20:1). A by-product [N,O-bis(6-chlorohexanesulfonyl)ethanolamine] was obtained from a first eluted fraction in the amount of 0.35 g, and N-(2-hydroxyethyl)-6-chlorohexanesulfonamide was obtained from a second eluted fraction as a colorless oil in the amount of 3.05 g.

(1) IR vmax (neat) cm$^{-1}$: 3492 (OH), 3293 (NH), 1318, 1143 (SO$_2$)
(2) Mass Spectroscopy (C$_8$H$_{18}$ClNO$_3$S) EI: m/z 244 [M+1]$^+$, CI: m/z 244 [M+1]$^+$
(3) EI-HRMS (C$_8$H$_{18}$ClNO$_3$S+H$^+$)
  Calculated: 244.0773, Found: 244.0781
(4) $^1$H-NMR (CDCl$_3$) δ: 1.42–1.61 (4H, m, ClCH$_2$CH$_2$CH$_2$CH$_2$), 1.81 (4H, m, ClCH$_2$CH$_2$, SCH$_2$CH$_2$), 2.38 (1H, t, J=5.1 Hz, OH), 3.05–3.10 (2H, m, SCH$_2$), 3.28 (2H, q, J=5.2 Hz, NCH$_2$), 3.55 (2H, t, J=6.5 Hz, ClCH$_2$), 3.78 (2H, q, J=5.1 Hz, OCH$_2$), 4.96 (1H, t, J=5.2 Hz, NH)

Preparation Example 5

Preparation of N-(2-Hydroxyethyl)-5-chloroPentanesulfonamide

The reaction was carried out in the same manner as in Preparation Example 4 except for using 5-chloropentanesulfonyl chloride (3.08 g, 15 mmol) in place of 6-chlorohexanesulfonyl chloride in Preparation Example 4, to give a by-product [N,O-bis(5-chloropetanesulfonyl)ethanolamine] from a first eluted fraction in the amount of 0.55 g and N-(2-hydroxyethyl)-5-chloropentanesulfonamide from a second eluted fraction as a colorless oil in the amount of 2.61 g.

(1) IR vmax (neat) cm$^{-1}$: 3494 (OH), 3295 (NH), 1318, 1144 (SO$_2$)
(2) Mass Spectroscopy (C$_7$H$_{16}$ClNO$_3$S) EI: m/z 230 [M+1]$^+$, CI: m/z 230 [M+1]$^+$
(3) EI-HRMS (C$_7$H$_1$ClNO$_3$S+H*)
  Calculated: 230.0617, Found: 230.0615
(4) $^1$H-NMR (CDCl$_3$) δ: 1.54–1.68 (2H, m, ClCH$_2$CH$_2$CH$_2$), 1.79–1.93 (4H, m, ClCH$_2$CH$_2$, SCH$_2$CH$_2$), 2.36 (1H, brs, OH), 3.09 (2H, t, J=8.0 Hz, SCH$_2$), 3.29 (2H, q, J=4.9 Hz, NCH$_2$), 3.57 (2H, t, J=6.5 Hz, ClCH$_2$), 3.78 (2H, brd, J=4.5 Hz, OCH$_2$), 4.97 (1H, m, NH)

Preparation Example 6

Preparation of N-(2-Hydroxyethyl)-12-bromododecanesulfonamide

Ethanolamine (0.67 g, 11 mmol) was reacted with 12-bromododecanesulfonyl chloride (1.74 g, 5 mmol) in the same manner as in Preparation Example 4, to give N-(2- hydroxyethyl)-12-bromododecanesulfonamide (1.37 g) as colorless crystals.

(1) Melting Point: 62°–63° C.
(2) IR vmax (KBr) cm$^{-1}$: 3537 (OH), 3298 (NH), 1322, 1127 (SO$_2$)
(3) Mass Spectroscopy (C$_{14}$H$_{30}$BrNO$_3$S) EI: m/z 372 [M+1]$^+$, CI: m/z 372 [M+1]$^+$
(4) EI-HRMS (Cl$_4$H$_{30}$BrNO$_3$S+H$^+$)
  Calculated: 372.1207, Found: 372.1200
(5) $^1$H-NMR (CDCl$_3$) δ: 1.26–1.51 (16H, m, BrCH$_2$CH$_2$(CH$_2$)$_8$CH$_2$CH$_2$S), 1.76–1.93 (4H, m, BrCH$_2$CH$_2$, SCH$_2$CH$_2$), 2.05–2.13 (1H, m, OH), 3.0–3.09 (2H, m, SCH$_2$), 3.29 (2H, q, J=4.9 Hz, NCH$_2$), 3.42 (2H, t, J=6.9 Hz, BrCH$_2$), 3.79 (2H, q, J=5.0 Hz, OCH$_2$), 4.71–4.79 (1H, m, NH)

Preparation Example 7

Preparation of N-(3-Hydroxypropyl)-6-chlorohexanesulfonamide

The reaction was carried out in the same manner as in Preparation Example 4 except for using n-propanolamine (2.48 g, 33 mmol) in place of ethanolamine in Preparation Example 4, to give a by-product [N,O-bis(6-chlorohexanesulfonyl)propanolamine] from a first eluted fraction in the amount of 0.85 g, and N-(3-hydroxypropyl)-6-chlorohexanesulfonamide from a second eluted fraction as a colorless waxy product in the amount of 2.86 g.

(1) IR vmax (neat) cm$^-$: 3447 (OH), 3244 (NH), 1330, 1136 (SO$_2$)
(2) Mass Spectroscopy (C$_9$H$_2$OClNO$_3$S) EI: m/z 258 [M+1]$^+$, CI: m/z 258 [M+1]$^+$
(3) EI-HRMS (C$_9$H$_{20}$ClNO$_3$S+H$^+$)
  Calculated: 258.0929, Found: 258.0936
(4) $^1$H-NMR (CDCl$_3$) δ: 1.44–1.56 (4H, m, ClCH$_2$CH$_2$CH$_2$CH$_2$), 1.74–1.89 (6H, m, ClCH$_2$CH$_2$, SCH$_2$CH$_2$, NHCH$_2$CH$_2$), 1.98 (1H, t, J=5.1 Hz, OH), 3.02–3.07 (2H, m, SCH$_2$), 3.30 (2H, q, J=6.2 Hz, NCH$_2$), 3.56 (2H, t, J=6.5 Hz, ClCH$_2$), 3.82 (2H, q, J=5.1 Hz, OCH$_2$), 4.79 (1H, t, J=6.2 Hz, NH)

Preparation Example 8

Preparation of N-(3-Hydroxypropyl)-5-chloropentanesulfonamide

The reaction was carried out in the same manner as in Preparation Example 4 except for using 5-chloropentanesulfonyl chloride (3.08 g, 15 mmol) in place of 6-chlorohexanesulfonyl chloride, and n-propanolamine (2.48 g, 33 mmol) in place of ethanolamine in Preparation Example 4, to give a by-product [N,O-bis(5-chloropetanesulfonyl)propanolamine] from a first eluted fraction in the amount of 0.64 g and N-(3-hydroxypropyl)-5-chloropentanesulfonamide from a second eluted fraction as a colorless waxy product in the amount of 2.76 g.

(1) IR vmax (neat) cm$^{-1}$: 3500–3200 (OH, NH), 1321, 1135 (SO$_2$)
(2) Mass Spectroscopy (C$_8$H$_{18}$ClNO$_3$S) EI: m/z 244[M+1]$^+$, CI: m/z 244 [M+1]$^+$
(3) EI-HRMS (C$_8$H$_{18}$ClNO$_3$S+H$^+$)
  Calculated: 244.0773, Found: 244.0777
(4) $^1$H-NMR (CDCl$_3$) δ: 1.54–1.67 (2H, m, ClCH$_2$CH$_2$CH$_2$), 1.78–1.91 (6H, m, ClCH$_2$CH$_2$, SCH$_2$CH$_2$, NCH$_2$CH$_2$), 2.01 (1H, m, OH), 3.05 (2H, t, J=8.0 Hz, SCH$_2$), 3.30 (2H, q, J=6.2 Hz, NCH$_2$), 3.57 (2H, t, J=6.4 Hz, ClCH$_2$), 3.82 (2H, brd, J=4.9 Hz, OCH$_2$), 4.84 (1H, m, NH)

Preparation Example 9

Preparation of N,N-Dimethyl-6-chlorohexanesulfonamide

6-Chlorohexanesulfonyl chloride (6.57g, 30 mmol) was added dropwise to a solution of diethyl ether (60 ml) and a 12% acetonitrile solution of dimethylamine (24.8 g, 66 mmol) with stirring under ice-cooling. Thereafter, the mixture was stirred at the same temperature for 20 minutes. The reaction mixture was concentrated in vacuo. Thereafter, the concentrate was diluted with diethyl ether (60 ml). The resulting solution was washed twice with water (10 ml) and then with brine (10 ml), and thereafter dried over anhydrous magnesium sulfate. Subsequently, the solvent was removed by evaporation in vacuo. The crude product was purified by column chromatography on silica gel with ethyl acetate-n-hexane (1:4), to give N,N-dimethyl-6-chlorohexanesulfonamide (6.59 g) as a pale yellow oil.

(1) IR vmax (neat) cm$^{-1}$: 1335, 1143 (SO$_2$)
(2) Mass Spectroscopy (CaHl,ClNO$_2$S) EI: m/z 228 [M+1]$^+$, CI: m/z 228 [M+1]$^+$
(3) EI-HRMS (C$_8$H$_{18}$ClNO$_2$S+H$^+$)
  Calculated: 228.0824, Found: 228.0824
(4) $^1$H-NMR (CDCl$_3$) δ: 1.41–1.60 (4H, m, ClCH$_2$CH$_2$CH$_2$CH$_2$), 1.71–1.88 (4H, m, ClCH$_2$CH$_2$, SCH$_2$CH$_2$), 2.87 (6H, s, CH$_3$x2), 2.89–2.94 (2H, m, SCH$_2$), 3.54 (2H, t, J=6.6 Hz, ClCH$_2$)

Preparation Example 10

Ppreparation of N,N-Dimethyl-5-chloropentanesulfonamide

A 50% aqueous solution of dimethylamine (5.95 g, 66 mmol) was added dropwise to a solution of diethyl ether (60 ml) and 5-chloropentanesulfonyl chloride (6.15 g, 30 mmol) with stirring under ice-cooling. Thereafter, the mixture was stirred at the same temperature for 20 minutes. The reaction solution was washed twice with water (10 ml) and then with brine (10 ml), and thereafter dried over anhydrous magnesium sulfate. Subsequently, the solvent was removed by evaporation in vacuo. The crude product was purified by column chromatography on silica gel with ethyl acetate-n-hexane (1:4), to give N,N-dimethyl-5-chloropentanesulfonamide (6.10 g) as a pale yellow oil.

(1) IR vmax (neat) cm$^{-1}$: 1334, 1145 (SO$_2$)
(2) Mass Spectroscopy (C$_7$H$_{16}$ClNO$_2$S) EI: m/z 214 [M+1]$^+$, CI: m/z 214 [M+1]$^+$
(3) EI-HRMS (C$_7$H$_{16}$ClNO$_2$S+H$^+$)
  Calculated: 214.0667, Found: 214.0658
(4) $^1$H-NMR (CDCl$_3$) δ: 1.59–1.67 (2H, m, ClCH$_2$CH$_2$CH$_2$), 1.80–1.93 (4H, m, ClCH$_2$CH$_2$, SCH$_2$CH$_2$), 2.90 (6H, s, CH$_3$x2), 2.91–2.97 (2H, m, SCH$_2$), 3.57 (2H, t, J=6.5 Hz, ClCH$_2$)

Preparation Example 11

Preparation of N,N-Diethyl-6-chlorohexanesulfonamide

6-Chlorohexanesulfonyl chloride (6.57g, 30 mmol) was added dropwise to a solution of diethyl ether (60 ml) and diethylamine (4.83g, 66 mmol) with stirring under ice-cooling. Thereafter, the mixture was stirred at the same temperature for 20 minutes. The reaction mixture was washed twice with water (10 ml) and then with brine (10 ml), and thereafter dried over anhydrous magnesium sulfate. Subsequently, the solvent was removed by evaporation In vacuo. The crude product was purified by column chromatography on silica gel with ethyl acetate-n-hexane (1:4), to give N,N-diethyl-6-chlorohexanesulfonamide (7.12 g) as a pale yellow oil.

(1) IR vmax (neat) cm$^{-1}$: 1329, 1140 ($SO_2$)
(2) Mass Spectroscopy ($ClOH_{22}ClNO_2S$) EI: m/z 255 [M]$^+$
(3) EI-HRMS ($ClOH_{22}ClNO_2s$)
    Calculated: 255.1059, Found: 255.1064
(4) $^1$H-NMR ($CDCl_3$) δ: 1.21 (6H, t, J=7.1 Hz, $CH_3$x2), 1.39–1.55 (4H, m, $ClCH_2CH_2CH_2CH_2$), 1.73–1.87 (4H, m, $ClCH_2CH_2$, $SCH_2CH_2$), 2.89–2.95 (2H, m, $SCH_2$), 3.30 (4H, q, J=7.1 Hz, $CH_3CH_2$x2), 3.54 (2H, t, J=6.5 Hz, $ClCH_2$)

Preparation Example 12

Preparation of N,N-Diethyl-5-chloropentanesulfonamide

The reaction was carried out in the same manner as in Preparation Example 11 except for using 5-chloropentanesulfonyl chloride (6.15g, 30 mmol) in place of 6-chlorohexanesulfonyl chloride in Preparation Example 11, to give N,N-diethyl-5-chloropentanesulfonamide (6.78 g) as a pale yellow oil.

(1) IR vmax (neat) cm$^{-1}$: 1329, 1140 ($SO_2$)
(2) Mass Spectroscopy ($C_9H_{20}ClNO_2S$) EI: m/z 242 [M+1]$^+$, CI: m/z 242 [M+1]$^+$
(3) EI-HRMS ($C_9H_{20}ClNO_2S+H^+$)
    Calculated: 242.0980, Found: 242.0976
(4) $^1$H-NMR ($CDCl_3$) δ: 1.22 (6H, t, J=7.1 Hz, $CH_3$x2), 1.58–1.62 (2H, m, $ClCH_2CH_2CH_2$), 1.80–1.88 (4H, m, $ClCH_2CH_2$, $SCH_2CH_2$), 2.91–2.96 (2H, m, $SCH_2$), 3.31 (4H, q, J=7.1 Hz, $CH_3CH_2$x2), 3.56 (2H, t, J=6.5 Hz, $ClCH_2$)

Preparation Example 13

Preparation of N-n-Butyl-N-methyl-6-chlorohexanesulfonamide

The reaction was carried out in the same manner as in Preparation Example 11 except for using N-methyl-n-butylamine (5.75g, 66 mmol) in place of diethylamine in Preparation Example 11, to give N-n-butyl-N-methyl-6-chlorohexanesulfonamide (7.56 g) as a pale yellow oil.

(1) IR vmax (neat) cm$^{-1}$: 1333, 1142 ($SO_2$)
(2) Mass Spectroscopy ($C_{11}H_{24}ClNO_2S$) EI: m/z 270 [M+1]$^+$, CI: m/z 270 [M+1]$^+$
(3) EI-HRMS ($C_{11}H_{24}ClNO_2S+H^+$)
    Calculated: 270.1293, Found: 270.1281
(4) $^1$H-NMR ($CDCl_3$) δ: 0.96 (3H, t, J=7.3 Hz, $CH_3CH_2$), 1.33–1.41 (2H, m, $CH_3CH_2$), 1.47–1.61 (6H, m, $ClCH_2CH_2CH_2CH_2$, $NCH_2CH_2$), 1.79–1.86 (4H, m, $ClCH_2CH_2$, $SCH_2CH_2$), 2.87 (3H, s, $NCH_3$), 2.90–2.95 (2H, m, $SCH_2$), 3.18 (2H, t, J=7.4 Hz, $NCH_2$), 3.55 (2H, t, J=6.6 Hz, $ClCH_2$)

Preparation Example 14

Preparation of N-n-Butyl-N-methyl-5-chloropentanesulfonamide

The reaction was carried out in the same manner as in Preparation Example 11 except for using N-methyl-n-butylamine (5.75g, 66 mmol) in place of diethylamine, and 5-chloropentanesulfonyl chloride (6.15g, 30 mmol) in place of 6-chlorohexanesulfonyl chloride in Preparation Example 11, to give N-n-butyl-N-methyl-5-chloropentanesulfonamide (7.12 g) as a pale yellow oil.

(1) IR vmax (neat) cm$^-$: 1333, 1143 ($SO_2$)
(2) Mass Spectroscopy ($C_{10}H_{22}ClNO_2S$) EI: m/z 256 [M+1]$^+$, CI: m/z 256 [M+1]$^+$
(3) EI-HRMS ($ClOH_{22}ClNO_2S+H^+$)
    Calculated: 256.1137, Found: 256.1137
(4) $^1$H-NMR ($CDCl_3$) δ: 0.96 (3H, t, J=7.3 Hz, $CH_3CH_2$), 1.33–1.41 (2H, m, $CH_3CH_2$), 1.54–1.63 (4H, m, $ClCH_2CH_2CH_2$, $NCH_2CH_2$), 1.79–1.88 (4H, m, $ClCH_2CH_2$, $SCH_2CH_2$), J=2.87 (3H, s, $NCH_3$), 2.88–2.96 (2H, m, $SCH_2$), 3.18 (2H, t, J=7.4 Hz, $NCH_2$), 3.56 (2H, t, J=6.5 Hz, $ClCH_2$)

Preparation Example 15

Preparation of (3-Chlorophenyl)phenylmethylamine hydrochloride

In accordance with the method described in *Bull. Soc. Chim. France*, 352–359 (1959), 3-chlorobenzophenone (43.33g, 0.2 mol) and ammonium formate (63.06g, 1.0 mol) were refluxed for 3 hours in nitrobenzene (250 ml). After cooling the refluxed mixture to room temperature, the reaction solution was concentrated in vacuo. A 15% HCl-ethanol solution (420 ml) was added to the residue, and the mixture was refluxed for 2 hours. The reaction solution was concentrated in vacuo. Thereafter, diethyl ether was added thereto, and the crude product was collected by filtration. Thereafter, (3-chlorophenyl)phenylmethylamine hydrochloride (21.86 g) was recrystallized from water as colorless needles.

(1) Melting Point: 263°–265° C.
(2) Elemental Analysis (as $C_{13}H_{12}ClN$ HCl)
    Calculated: C, 61.43; H, 5.15; N, 5.51
    Found: C, 61.36; H, 5.03; N, 5.50

Preparation Example 16

Preparation of +(+)-(3-Chlorophenyl)phenylmethylamine (3-Chlorophenyl)phenylmethylamine (9.42g, 43.3 mmol) and (+)-tartaric acid (6.50g, 43.3 mmol) were dissolved in water (40 ml) with heating. Thereafter, the precipitated crude crystals obtained by allowing to cool the reaction solution to room temperature were collected by filtration. The resulting crystals were purified by repeatedly recrystallizing from water, to give (+)-(3-chlorophenyl)phenylmethylamine (+)-tartrate (4.28 g). In order to determine the optical purity of (+)-(3-chlorophenyl)phenylmethylamine (+)-tartrate, HPLC analysis was carried out. Its analytical conditions are as follows.

HPLC Analytical Conditions

Column: ULTRON ES—OVM, 4.6 mm×150 mm (5 μm)
Mobile Phase: acetonitrile:phosphate buffer (pH 7.0)= 12.5:87.5
Flow Rate: 1.0 ml/min.
Detection: at UV 254 nm
Retention Time
[(3-chlorophenyl)phenylmethylamine hydrochloride (racemate)]:

12.1 min. [50%, (−)-form]
13.4 min. [50%, (+)-form]

Subject: 12.2 min. (1.1%), 13.4 min. (98.9%)

From the above results, it was found that the optical purity of the (+)-(3-chlorophenyl)phenylmethylamine (+)-tartrate obtained in Preparation Example 16 was 97.8% ee.

Next, (+)-(3-chlorophenyl)phenylmethylamine (+)tartrate (4.28 g) was suspended in chloroform (40 ml), and 28%-aqueous ammonia was added thereto to neutralize the mixture. Thereafter, the chloroform layer was separated therefrom. The extract was dried over anhydrous magnesium sulfate, and the solvent was removed by evaporation in vacuo, to give (+)-(3-chlorophenyl)phenylmethylamine (2.45 g) as a pale yellow oil.

(1) $[\alpha]_D^{26}$ +19.2° (c=5.0, ethanol)

Preparation Example 17

Preparation of (+) -1-[(3-Chlorophenyl)phenylmethyl]-4-[(4-methylphenyl)sulfonyl]piperazine (+)-(3-Chlorophenyl)phenylmethylamine (2.45 g, 11.27 mmol) and N,N-bis(2-chloroethyl)-4-methylbenzenesulfonamide (3.67g, 12.39 mmol) were refluxed for 4 hours in N-ethyldiisopropylamine (15 ml). The reaction mixture was concentrated in vacuo, and water was added thereto. The mixture was extracted with chloroform. The chloroform layer was washed with water and then dried over anhydrous magnesium sulfate. Thereafter, the crude product obtained by removing the solvent by evaporation in vacuo was purified by column chromatography on silica gel with chloroform, to give (+)-1-[(3-chlorophenyl)phenylmethyl]-4-[(4-methylphenyl)sulfonyl]piperazine (4.82 g) as colorless prisms.

(1) Melting Point: 217°–218° C. (acetone)
(2) Elemental Analysis (as $C_{24}H_{25}ClN_2O_2S$)
   Calculated: C, 65.36; H, 5.72; N, 6.35
   Found: C, 65.34; H, 5.85; N, 6.27
(3) $[\alpha]_D^{27}$+26.40 (c=3.0, chloroform)

Preparation Example 18

Preparation of (+)-1-[(3-Chlorophenyl)phenylmethyl]piperazine (+)-1-[(3-Chlorophenyl)phenylmethyl]-4-[(4-methylphenyl)sulfonyl]piperazine (4.62 g, 10.48 mmol) was stirred in 30% hydrobromic acid-acetic acid solution (20 ml) in the presence of 4-hydroxybenzoic acid (5.06g, 36.66 mmol) at room temperature for two days. 28%-Aqueous ammonia was added to the reaction mixture, and the resulting mixture was extracted with chloroform. The chloroform layer was washed with water and then dried over anhydrous magnesium sulfate. Thereafter, the crude product obtained by removing the solvent by evaporation in vacuo was purified by column chromatography on silica gel with chloroform-methanol (20:1), to give (+)-1-[(3-chlorophenyl)phenylmethyl]piperazine (2.67 g).

(1) Mass Spectroscopy ($C_{17}H_{19}ClN_2$) EI: m/z 286 [M]$^+$
(2) EI-HRMS ($C_{17}H_{19}ClN_2$)
   Calculated: 286.1236, Found: 286.1235
(3) $[\alpha]_D^{27}$+18.3° (c=2.145, methanol)

Next, in order to determine the optical purity of (+)-1-[(3-chlorophenyl)phenylmethyl]piperazine, HPLC analysis was carried out. Its analytical conditions are as follows.

HPLC Analytical Conditions

Column: ULTRON ES—OVM, 4.6 mm×150 mm (5 μm)
Mobile Phase: acetonitrile:acetate buffer (pH 5.1)=1:9
Flow Rate: 1.2 ml/min.
Detection: at UV 254 nm
Retention Time
[1-[(3-chlorophenyl)phenylmethyl]piperazine (racemate)]:
   6.7 min. [50%, (+)-form]
   7.9 min. [50%, (−)-form]
Subject: 5.8 min. (98.7%), 8.0 min. (1.3%)

From the above results, it was found that the optical purity of the (+)-1-[(3-chlorophenyl)phenylmethyl]piperazine obtained in Preparation Example 18 was 97.4% ee.

Preparation Example 19

Preparation of (−)-(3-Chlorophenyl)phenylmethylamine (3-Chlorophenyl)phenylmethylamine (9.25g, 42.5 mmol) and (−)-tartaric acid (7.02 g, 46.7 mmol) were dissolved in water (40 ml) with heating. Thereafter, the precipitated crude crystals obtained by allowing to cool the reaction solution to room temperature were collected by filtration. The resulting crystals were purified by repeatedly recrystallizing from water, to give (−)-(3-chlorophenyl)phenylmethylamine (−)-tartrate (4.58 g).

In order to determine the optical purity of (−)-(3-chlorophenyl)phenylmethylamine (−)-tartrate, HPLC analysis was carried out in accordance with the method in Preparation Example 16. As a result, it was found that the optical purity of the (−)-(3-chlorophenyl)phenylmethylamine (−)-tartrate was 97.6% ee.

Next, (−)-(3-chlorophenyl)phenylmethylamine (−)tartrate (4.50 g) was suspended in chloroform (40 ml). 28%-Aqueous ammonia was added to the reaction mixture to neutralize the mixture. Thereafter, the chloroform layer was separated therefrom, and the extract was dried over anhydrous magnesium sulfate. Thereafter, the solvent was removed by evaporation in vacuo, to give (−)-(3-chlorophanyl)phenylmethylamine (2.63 g) as a pale yellow oil.

(1) $[\alpha]_D^{26}$19.2° (c=5.0, ethanol)

Preparation Example 20

Preparation of (−)-1-[(3-Chlorophenyl)phenylmethyl]-4-[4-methylphenyl)sulfonyl]piperazine (−)-(3-Chlorophenyl)phenylmethylamine (2.63 g, 12.1 mmol) and N,N-bis(2-chloroethyl)-4-methylbenzenesulfonamide (3.94 g, 13.3 mmol) were refluxed for 4 hours in N-ethyldiisopropylamine (15 ml). The reaction mixture was concentrated in vacuo, and water was added thereto. The mixture was extracted with chloroform. The chloroform layer was washed with water and then dried over anhydrous magnesium sulfate. Thereafter, the crude product obtained by removing the solvent by evaporation in vacuo was purified by column chromatography on silica gel with chloroform, to give (−) -1-[(3-chlorophenyl)phenylmethyl]-4-[4-methylphenyl)sulfonyl]piperazine (5.20 g) as colorless prisms.

(1) Melting Point: 215°–217° C. (acetone)
(2) Elemental Analysis (as $C_{24}H_{25}ClN_2O_2S$)
   Calculated: C, 65.36; H, 5.72; N, 6.35
   Found: C, 65.23; H, 5.62; N, 6.34
(3) $[\alpha]_D^{27}$ 25.6° (c=3.0, chloroform)

Preparation Example 21

Preparation of (−)-1-[(3-Chlorophenyl)phenylmethyl]piperazine (−)-1-1(3-Chlorophenyl)phenylmethyl]-4-[(4-methylphenyl)sulfonyl]piperazine (5.00g, 11.3 mmol) was stirred in 30% hydrobromic acid-acetic acid solution (20 ml) in the presence of 4-hydroxybenzoic acid (5.48 g, 39.7 mmol) at room temperature for two days. 28%-Aqueous ammonia was added to the reaction mixture, and the resulting mixture was extracted with chloroform. The chloroform layer was washed with water and then dried over anhydrous magnesium sulfate. Thereafter, the crude product obtained by removing the solvent by evaporation in vacuo was purified by column chromatography on silica gel with chloroform-methanol (20:1), to give (−)-1-[(3-chlorophenyl)phenylmethyl]piperazine (2.60 g).

(1) Mass Spectroscopy ($C_{17}H_{19}ClN_2$) EI: m/z 286 [M]⁺
(2) EI-HRMS ($C_{17}H_{19}ClN_2$)
   Calculated: 286.1236, Found: 286.1239
(3) $[\alpha]_D^{27}$ 18.3° (c=2.145, methanol)

In order to determine the optical purity of the resulting (−)-1-[(3-chlorophenyl)phenylmethyl]piperazine, HPLC analysis was carried out in accordance with the method in Preparation Example 18. As a result, it was found that the optical purity of the (−)-1-[(3-chlorophenyl)phenylmethyl]piperazine was 97.6% ee.

Preparation Example 22

Preparation of N-(4-Hydroxybutyl)-6-chlorohexanesulfonamide

A solution of ethyl acetate (15 ml) and 6-chlorohexanesulfonyl chloride (3.29g, 15 mmol) was added dropwise to a suspension of ethyl acetate (15 ml) of 4-amino-1-butanol (2.94g, 33 mmol) under ice-cooling. Thereafter, the mixture was stirred at room temperature for 1 hour. Water was added to the reaction mixture, and the mixture was extracted with ethyl acetate (50 ml). The extract was dried over anhydrous magnesium sulfate.

Subsequently, the solvent was removed by evaporation in vacuo. The crude product was purified by column chromatography on silica gel with chloroform-methanol (20:1), to give N-(4-hydroxybutyl)-6-chlorohexanesulfonamide (2.4 g) as colorless crystals.

(1) Melting Point: 61°–62° C. (ethyl acetate)
(2) IR vmax (KBr) cm⁻¹: 3412 (OH), 3276 (NH), 1332, 1133 ($SO_2$)
(3) Mass Spectroscopy ($ClOH_{22}ClNO_3S$) EI: m/z 272 [M+1]⁺, CI: m/z 272 [M+1]⁺
(4) EI-HRMS ($C_{10}H_{22}ClNO_3+H^+$)
   Calculated: 272.1086, Found: 272.1086
(5) ¹H-NMR (CDCl₃) δ: 1.42–1.57 (4H, m, ClCH₂CH₂CH₂CH₂), 1.61–1.89 (9H, m, ClCH₂CH₂, SCH₂CH₂, NHCH₂CH₂CH₂, OH), 3.00–3.05 (2H, m, SCH₂), 3.17 (2H, q, J=6.2 Hz, NCH₂x2), 3.55 (2H, t, J=6.5 Hz, ClCH₂), 3.70 (2H, brs, OCH₂), 4.77 (1H, brs, NH)
(6) Elemental Analysis ($C_{10}H_{22}ClNO_3S$)
   Calculated: C, 44.19; H, 8.16; N, 5.15
   Found: C, 44.22; H, 8.12; N, 4.99

Preparation Example 23

Preparation of N-(4-Hydroxybutyl)-5-chloropentanesulfonamide

The reaction was carried out in the same manner as in Preparation Example 22 except for using 5-chloropentanesulfonyl chloride (3.08g, 15 mmol) in place of 6-chlorohexanesulfonyl chloride in Preparation Example 22, to give a desired compound (2.19 g) as colorless crystals.

(1) Melting Point: 740–75° C. (ethyl acetate)
(2) IR vmax (KBr) cm⁻¹: 3400 (OH), 3275 (NH), 1333, 1130 ($SO_2$)
(3) Mass Spectroscopy ($C_9H_{20}ClNO_3S$) EI: m/z 258 [M+1]⁺, CI: m/z 258 [M+1]⁺
(4) EI-HRMS ($C_9H_{20}ClNO_3+H^+$)
   Calculated: 258.0929, Found: 258.0929
(5) ¹H-NMR (CDCl₃) δ: 1.54–1.76 (6H, m, ClCH₂CH₂CH₂, NHCH₂CH₂CH₂), 1.79–1.91 (5H, m, ClCH₂CH₂, SCH₂CH₂, OH), 3.04 (2H, t, J=8.0 Hz, SCH₂), 3.17 (2H, q, J=6.2 Hz, NCH₂), 3.57 (2H, t, J=6.5 Hz, ClCH₂), 3.70 (2H, brs, OCH₂), 4.79 (1H, m, NH)
(6) Elemental Analysis ($C_9H_{20}ClNO_3S$)
   Calculated: C, 41.93; H, 7.82; N, 5.43
   Found: C, 41.89; H, 7.56; N, 5.22

Preparation Example 24

Preparation of N-Cyclopropyl-10-bromodecanesulfonamide

The reaction was carried out in the same manner as in Preparation Example 3 except for using 10-bromodecanesulfonyl chloride (450 mg, 1.41 mmol) in place of 6-bromohexanesulfonyl chloride, and cyclopropylamine (177 mg, 3.10 mmol), to give N-cyclopropyl-10-bromodecanesulfonamide (467 mg) as colorless crystals.

(1) Melting Point: 57°–60° C. (chloroform-n-hexane)
(2) IR vmax (KBr) cm⁻¹ : 3273 (NH), 1317, 1135 ($SO_2$)
(3) Mass Spectroscopy ($C_{13}H_{26}BrNO_2S$) EI: m/z 340 [M+1]⁺, CI: m/z 340 [M+1]⁺
(4) EI-HRMS ($C_{13}H_{26}BrNO_2S+H^+$)
   Calculated: 340.0945, Found: 340.0938
(5) ¹H-NMR (CDCl₃) δ: 0.67–0.79 (4H, m, CHCH₂x2), 1.32–1.48 (12H, m, CH₂x6), 1.79–1.93 (4H, m, BrCH₂CH₂, SCH₂CH₂), 2.56–2.62 (1H, m, CH), 3.06–3.11 (2H, m, SCH₂), 3.42 (2H, t, J=6.8 Hz, BrCH₂), 4.60 (1H, brs, NH)
(6) Elemental Analysis ($C_{13}H_{26}BrNO_2S$)
   Calculated: C, 45.88; H, 7.70; N, 4.12
   Found: C, 46.03; H, 7.59; N, 4.27

Preparation Example 25

Preparation of N-Cyclopropyl-1-bromoundecanesulfonamide

The reaction was carried out in the same manner as in Preparation Example 3 except for using 11-bromoundecanesulfonyl chloride (2.29g, 6.85 mmol) in place of 6-bromohexanesulfonyl chloride, and cyclopropylamine (860 mg, 15.1 mmol), to give N-cyclopropyl-11-bromoundecanesulfonamide (2.33 g) as colorless crystals.

(1) Melting Point: 71°–73° C. (chloroform-n-hexane)
(2) IR vmax (KBr) cm$^{-1}$: 3274 (NH), 1317, 1135 (SO$_2$)
(3) Mass Spectroscopy (C$_{14}$H$_{28}$BrNO$_2$S) EI: m/z 354 [M+1]$^+$, CI: m/z 354 [M+1]$^+$
(4) EI-HRMS (C$_{14}$H$_{28}$BrNO$_2$S+H$^+$)
 Calculated: 354.1101, Found: 354.1092
(5) $^1$H-NMR (CDCl$_3$) δ: 0.65–0.79 (4H, m, CHCH$_2$x2), 1.31–1.48 (14H, m, CH$_2$x7), 1.74–1.92 (4H, m, BrCH$_2$CH$_2$, SCH$_2$CH$_2$), 2.57–2.62 (1H, m, CH), 3.06–3.11 (2H, m, SCH$_2$), 3.42 (2H, t, J=6.8 Hz, BrCH$_2$), 4.61 (1H, brs, NH)

Preparation Example 26

Preparation of N-Cyclopropyl-12-bromododecanesulfonamide

The reaction was carried out in the same manner as in Preparation Example 3 except for using 12-bromododecanesulfonyl chloride (2.92g, 8.4 mmol) in place of 6-bromohexanesulfonyl chloride, and cyclopropylamine (1.08g, 18.5 mmol), to give N-cyclopropyl-12-bromododecanesulfonamide (2.99 g) as colorless crystals.

(1) Melting Point: 71°14 73° C. (n-hexane)
(2) IR vmax (KBr) cm$^{-1}$: 3274 (NH), 1318, 1135 (SO$_2$)
(3) Mass Spectroscopy (Cl$_5$H$_{30}$BrNO$_2$S) EI: m/z 368 [M+1]$^+$, CI: m/z 368 [M+1]$^+$
(4) EI-HRMS (C$_{15}$H$_{30}$BrNO$_2$S+H$^+$)
 Calculated: 368.1257, Found: 368.1261
(5) $^1$H-NMR (CDCl$_3$) δ: 0.66–0.79 (4H, m, CHCH$_2$x2), 1.30–1.50 (16H, m, CH$_2$x8), 1.74–1.92 (4H, m, BrCH$_2$CH$_2$, SCH$_2$CH$_2$), 2.57–2.63 (1H, m, CH), 3.06–3.11 (2H, m, SCH$_2$), 3.43 (2H, t, J=6.8 Hz, BrCH$_2$), 4.58 (1H, brs, NH)
(6) Elemental Analysis (C$_{15}$H$_{30}$BrNO$_2$S)
 Calculated: C, 48.90; H, 8.21; N, 3.80
 Found: C, 49.18; H, 8.36; N, 4.08

Example 1

[Preparation of N-Cyclopropyl-6-[4-[(3-chlorophenyl)phenylmethyl]-1-piperazinyl]hexanesulfonamide]

1-[(3-Chlorophenyl)phenylmethyl]piperazine (543.7 mg, 1.90 mmol) and N-cyclopropyl-6-chlorohexanesulfonamide (500 mg, 2.09 mmol) were refluxed in N-ethyldiisopropylamine (2 ml) for 4 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-cyclopropyl-6-[4-[(3-chlorophenyl)phenylmethyl]-1-piperazinyl]hexanesulfonamide (884.7 mg) as an oil (yield based on 1-[(3-chlorophenyl)phenylmethyl]piperazine: 95.2%).

(1) IR vmax (neat) cm$^{-1}$: 3274 (NH), 1320, 1143 (SO$_2$)
(2) Mass Spectroscopy (C$_{26}$H$_{36}$ClN$_3$O$_2$S) EI: m/z 489 [M]$^+$
(3) EI-HRMS (C$_{26}$H$_{36}$ClN$_3$O$_2$S)
 Calculated: 489.2215, Found: 489.2213
(4) $^1$H-NMR (CDCl$_3$) δ: 0.65–0.78 (4 H, m, CHCH$_2$CH$_2$), 1.30–1.56 (6 H, m, NCH$_2$CH$_2$CH$_2$CH$_2$), 1.76–1.88 (2 H, m, SCH$_2$CH$_2$), 2.35 (2 H, t, J=7.8 Hz, NCH$_2$), 2.38–2.53 (8 H, m, NCH$_2$CH$_2$x2), 2.55–2.62 (1 H, m, CHCH$_2$CH$_2$), 3.05–3.10 (2 H, m, SCH$_2$), 4.22 (1 H, s, CH), 4.60 (1 H, s, NH), 7.13–7.45 (9 H, m, ArH)

Example 2

[Preparation of N-Cyclopropyl-6-[4-[(3-chlorophenyl)phenylmethyl]-1-piperazinyl]hexanesulfonamide]

1-[(3-Chlorophenyl)phenylmethyl]piperazine (458.6 mg, 1.60 mmol) and N-cyclopropyl-6-bromohexanesulfonamide (500 mg, 1.76 mmol) were refluxed in N-ethyldiisopropylamine (2 ml) for 4 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-cyclopropyl-6-[4-[(3-chlorophenyl)phenylmethyl]-1-piperazinyl]hexanesulfonamide (711.3 mg) as an oil (yield based on 1-[(3-chlorophenyl)phenylmethyl]piperazine: 90.8%).

The resulting N-cyclopropyl-6-[4-[(3-chlorophenyl)phenylmethyl]-1-piperazinyl]hexanesulfonamide had physical properties similar to those of N-cyclopropyl-6-[4-[(3-chlorophenyl)phenylmethyl]-1-piperazinyl]hexanesulfonamide obtained in Example 1.

Example 3

[Preparation of N-Cyclopropyl-6-[4-[(3-chlorophenyl)phenylmethyl]-1-piperazinyl]hexanesulfonamide]

1-[(3-Chlorophenyl)phenylmethyl]piperazine (458.6 mg, 1.60 mmol) and N-cyclopropyl-6-bromohexanesulfonamide (500 mg, 1.76 mmol) were refluxed in triethylamine (2 ml) for 4 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel chloroform-methanol (20:1), to give N-cyclopropyl-6-[4-[(3-chlorophenyl)phenylmethyl]-1-piperazinyl]hexanesulfonamide (737.8 mg) as an oil (yield based on 1-[(3-chlorophenyl)phenylmethyl]piperazine: 94.1%).

The resulting N-cyclopropyl-6-[4-[(3-chlorophenyl)phenylmethyl]-1-piperazinyl]hexanesulfonamide had physical properties similar to those of N-cyclopropyl-6-[4-[(3-chlorophenyl)phenylmethyl]-1-piperazinyl]hexanesulfonamide obtained in Example 1.

Example 4

[Preparation of N-Cyclopropyl-6-[4-[(4-chlorophenyl)phenylmethyl]-1-piperazinyl]hexanesulfonamide]

1-[(4-Chlorophenyl)phenylmethyl]piperazine (3.00 g, 10.46 mmol) and N-cyclopropyl-6-chlorohexanesulfonamide (2.76 g, 11.51 mmol) were refluxed in N-ethyldiisopropylamine (8 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-cyclopropyl-6-[4-[(4-chlorophenyl)phenylmethyl]-1-piperazinyl]hexanesulfonamide (4.62 g) as an oil (yield based on 1-[(4-chlorophenyl)phenylmethyl]piperazine: 90.1%).

(1) IR vmax (neat) cm$^{-1}$: 3272 (NH), 1317, 1147 (SO$_2$)
(2) Mass Spectroscopy (C$_{26}$H$_{36}$ClN$_3$O$_2$S) EI: m/z 489 [M]$^+$
(3) EI-HRMS (C$_{26}$H$_{36}$ClN$_3$O$_2$S)
Calculated: 489.2215, Found: 489.2217
(4) $^1$H-NMR (CDCl$_3$) δ: 0.65–0.78 (4 H, m, CHCH$_2$CH$_2$), 1.30–1.57 (6 H, m, NCH$_2$CH$_2$CH$_2$CH$_2$), 1.76–1.87 (2 H, m, SCH$_2$CH$_2$), 2.36 (2 H, t, J=7.9 Hz, NCH$_2$), 2.39–2.53 (8 H, m, NCH$_2$CH$_2$x2), 2.55–2.62 (1 H, m, CHCH$_2$CH$_2$), 3.05–3.10 (2 H, m, SCH$_2$), 4.23 (1 H, s, CH), 4.64 (1 H, s, NH), 7.17–7.40 (9 H, m, ArH)

Example 5

[Preparation of N-Cyclopropyl-6-[4-[bis(4-chlorophenyl)methyl]-1-piperazinyl]hexanesulfonamide]

1-[Bis(4-chlorophenyl)methyl]piperazine (10.00 g, 31.13 mmol) and N-cyclopropyl-6-chlorohexanesulfonamide (8.30 g, 34.63 mmol) were refluxed in N-ethyldiisopropylamine (50 ml) for 7 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-cyclopropyl-6-[4-[bis(4-chlorophenyl)methyl]-1-piperazinyl]hexanesulfonamide (14.70 g) as an oil (yield based on 1-[bis(4-chlorophenyl)methyl]piperazine: 95.3%).

(1) IR vmax (neat) cm$^{-1}$: 3273 (NH), 1317, 1143 (SO$_2$)
(2) Mass Spectroscopy (C$_{26}$H$_{35}$Cl$_2$N$_3$O$_2$S) EI: m/z 523 [M]$^+$
(3) EI-HRMS (C$_{26}$H$_{35}$Cl$_2$N$_3$O$_2$S)
Calculated: 523.1825, Found: 523.1823
(4) $^1$H-NMR (CDCl$_3$) δ: 0.65–0.78 (4 H, m, CHCH$_2$CH$_2$), 1.30–1.56 (6 H, m, NCH$_2$CH$_2$CH$_2$CH$_2$), 1.77–1.87 (2 H, m, SCH$_2$CH$_2$), 2.34 (2 H, t, J=7.8 Hz, NCH$_2$), 2.38–2.52 (8 H, m, NCH$_2$CH$_2$X2), 2.55–2.62 (1 H, m, CHCH$_2$CH$_2$), 3.05–3.10 (2 H, m, SCH$_2$), 4.21 (1 H, s, CH), 4.61 (1 H, s, NH), 7.23–7.35 (8 H, m, ArH)

Example 6

[Preparation of N-Cyclopropyl-6-[4-[bis(3-chlorophenyl)methyl]-1-piperazinyl]hexanesulfonamide]

1-[Bis(3-chlorophenyl)methyl]piperazine (5.00 g, 15.5 mmol) and N-cyclopropyl-6-chlorohexanesulfonamide (4.15 g, 17.30 mmol) were refluxed in N-ethyldiisopropylamine (25 ml) for 7 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-cyclopropyl-6-[4-[bis(3-chlorophenyl)methyl]-1-piperazinyl]hexanesulfonamide (7.73 g) as an oil (yield based on 1-[bis(3-chlorophenyl)methyl]piperazine: 94.7%).

(1) IR vmax (neat) cm$^{-1}$: 3274 (NH), 1317, 1143 (SO$_2$)
(2) Mass Spectroscopy (C$_{26}$H$_{35}$Cl$_2$N$_3$O$_2$S) EI: m/z 523 [M]$^+$
(3) EI-HRMS (C$_{26}$H$_{35}$Cl$_2$N$_3$O$_2$S)
Calculated: 523.1825, Found: 523.1822
(4) $^1$H-NMR (CDCl$_3$) δ: 0.66–0.78 (4 H, m, CHCH$_2$CH$_2$), 1.28–1.55 (6 H, m, NCH$_2$CH$_2$CH$_2$CH$_2$), 1.76–1.87 (2 H, m, SCH$_2$CH$_2$), 2.35 (2 H, t, J=7.8 Hz, NCH$_2$), 2.38–2.51 (8 H, m, NCH$_2$CH$_2$x2), 2.55–2.62 (1 H, m, CHCH$_2$CH$_2$), 3.05–3.10 (2 H, m, SCH$_2$), 4.20 (1 H, s, CH), 4.61 (1 H, s, NH), 7.16–7.41 (8 H, m, ArH)

Example 7

[Preparation of N-Cyclopropyl-6-[4-[bis(4-fluoronhenyl)methyl]-1-piperazinyl]hexanesulfonamide]

1-[Bis(4-fluorophenyl)methyl]piperazine (8.92 g, 30.0 mmol) and N-cyclopropyl-6-chlorohexanesulfonamide (7.91 g, 33.0 mmol) were refluxed in N-ethyldiisopropylamine (20 ml) for 8 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (50:3), to give N-cyclopropyl-6-[4-[bis(4-fluorophenyl)methyl]1-piperazinyl]hexanesulfonamide (13.97 g) as a crystalline substance (yield based on 1-[bis(4-fluorophenyl)methyl]piperazine: 94.7%).

(1) IR vmax (neat) cm$^{-1}$: 3273 (NH), 1318, 1151 (SO$_2$)
(2) Mass Spectroscopy (C$_{26}$H$_{35}$F$_2$N$_3$O$_2$S) EI: m/z 491 [M]$^+$
(3) EI-HRMS (C$_{26}$H$_{35}$F$_2$N$_3$O$_2$S)
Calculated: 491.2416, Found: 491.2418
(4) $^1$H-NMR (CDCl$_3$) δ: 0.66–0.78 (4 H, m, CHCH$_2$CH$_2$), 1.28–1.55 (6 H, m, NCH$_2$CH$_2$CH$_2$CH$_2$), 1.76–1.87 (2 H, m, SCH$_2$CH$_2$), 2.34 (2 H, t, J=7.8 Hz, NCH$_2$), 2.37–2.54 (8 H, m, NCH$_2$CH$_2$x2), 2.54–2.62 (1 H, m, CHCH$_2$CH$_2$), 3.05–3.10 (2 H, m, SCH$_2$), 4.23 (1 H, s, CH), 4.60 (1 H, s, NH), 6.93–7.02 (4 H, m, ArH), 7.32–7.39 (4 H, m, ArH)

Example 8

[Preparation of N-Cyclopropyl-6-[4-[4-chlorophenyl-(2-Pyridyl)methyl[-1-piperazinyl]hexanesulfonamide]

1-[4-Chlorophenyl-(2-pyridyl)methyl]piperazine (7.90 g, 27.5 mmol) and N-cyclopropyl-6-chlorohexanesulfonamide (7.24 g, 30.2 mmol) were refluxed in N-ethyldiisopropylamine (20 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-cyclopropyl-6-[4-[4-chlorophenyl-(2-pyridyl)methyl]-1-piperazinyl]hexanesulfonamide (6.29 g) as an oil (yield based on 1-[4-chlorophenyl-(2-pyridyl)methyl]piperazine: 92.7%).

(1) IR vmax (neat) cm$^{-1}$: 3271 (NH), 1317, 1143 (SO$_2$)

(2) Mass Spectroscopy (C$_{25}$H$_{35}$ClN$_4$O$_2$S) EI: m/z 490 [M]$^+$ (3) EI-HRMS (C$_{25}$H$_{35}$ClN$_4$O$_2$S)
Calculated: 490.2167, Found: 490.2170

(4) $^1$H-NMR (CDCl$_3$) δ: 0.64–0.78 (4 H, m, CHCH$_2$CH$_2$), 1.27–1.55 (6 H, m, NCH$_2$CH$_2$CH$_2$CH$_2$), 1.76–1.87 (2 H, m, SCH$_2$CH$_2$), 2.34 (2 H, t, J=7.8 Hz, NCH$_2$), 2.37–2.53 (8 H, m, NCH$_2$CH$_2$x2), 2.53–2.62 (1 H, m, CHCH$_2$CH$_2$), 3.04–3.10 (2 H, m, SCH$_2$), 4.42 (1 H, s, CH), 4.68 (1 H, s, NH), 7.09–7.66 (7 H, m, ArH), 8.50–8.53 (1 H, m, ArH)

Example 9

[Preparation of N-Cyclopentyl-6-[4-[4-fluorophenyl-(2-pyridyl)methyl]-1-piperazinyl]hexanesulfonamide]

1-[4-Fluorophenyl-(2-pyridyl)methyl]piperazine (2.57 g, 9.5 mmol) and N-cyclopentyl]-6-chlorohexanesulfonamide (2.80 g, 10.5 mmol) were refluxed in N-ethyldiisopropylamine (8 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-cyclopentyl-6-[4-[4-fluorophenyl-(2-pyridyl)methyl]-1-piperazinyl]hexanesulfonamide (4.30 g) as an oil (yield based on 1-[4-fluorophenyl-(2-pyridyl)methyl]piperazine: 90.1%).

(1) IR vmax (neat) cm$^{-1}$: 3278 (NH), 1324, 1143 (SO$_2$)

(2) Mass Spectroscopy (C$_{27}$H$_{39}$FN$_4$O$_2$S) EI: m/z 502 [M]$^+$ (3) EI-HRMS (C$_{27}$H$_{39}$FN$_4$O$_2$S)
Calculated: 502.2775, Found: 502.2774

(4) $^1$H-NMR (CDCl$_3$) δ: 1.23–1.86 (14 H, m, CH(CH$_2$CH$_2$)$_2$, NCH$_2$CH$_2$CH$_2$CH$_2$), 1.95–2.06 (2 H, m, SCH$_2$CH$_2$), 2.34 (2 H, t, J=7.8 Hz, NCH$_2$), 2.37–2.53 (8 H, m, NCH$_2$CH$_2$x2), 2.98–3.03 (2 H, m, SCH$_2$), 3.70–3.82 (1 H, m, CHCH$_2$CH$_2$), 4.12 (1 H, d, J=7.6 Hz, NH), 4.43 (1 H, s, CH), 6.92–7.66 (7 H, m, ArH), 8.50–8.54 (1 H, m, ArH)

Example 10

[Preparation of 6-[4-[(3-Chlorophenyl)phenylmethyl]-1-piperazinyl]hexanesulfonamide]

1-[(3-Chlorophenyl)phenylmethyl]piperazine (500 mg, 1.74 mmol) and 6-chlorohexanesulfonamide (383 mg, 1.92 mmol) synthesized referring to a process described in *J. Org. Chem.* 52, 2162 (1987) were refluxed in N-ethyldiisopropylamine (5 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (100:3), to give 6-[4-[(3-chlorophenyl)phenylmethyl]1-piperazinyl]hexanesulfonamide (749 mg) as a colorless oil (yield based on 1-[(3-chlorophenyl)phenylmethyl]piperazine: 95.4%).

(1) IR vmax (neat) cm$^{-1}$: 3274 (NH), 1324, 1147 (SO$_2$)

(2) Mass Spectroscopy (C$_{23}$H$_{32}$ClN$_3$O$_2$S) EI: m/z 449 [M]$^+$ (3) EI-HRMS (C$_{23}$H$_{32}$ClN$_3$O$_2$S)
Calculated: 449.1902, Found: 449.1897

(4) $^1$H-NMR (CDCl$_3$) δ: 1.30–1.57 (6 H, m, NCH$_2$CH$_2$CH$_2$CH$_2$), 1.82–1.94 (2 H, m, SCH$_2$CH$_2$), 2.35 (2 H, t, J=8.0 Hz, NCH$_2$), 2.39–2.53 (8 H, m, NCH$_2$CH$_2$x2), 3.10–3.14 (2 H, m, SCH$_2$), 4.22 (1 H, s, CH), 4.67 (2 H, brs, NH$_2$), 7.14–7.45 (9 H, m, ArH)

Example 11

[Preparation of N-Cyclopropyl-6-[4-(3-chlorophenyl)phenylmethyl]-1-piperazinyl]hexanesulfonamide fumarate]

N-Cyclopropyl-6-[4-[(3-chlorophenyl)phenylmethyl]-1-piperazinyl]hexanesulfonamide (13.03 g, 26.59 mmol) prepared in the same manner as in Example 1 was dissolved in ethanol (100 ml). Fumaric acid (4.01 g, 34.55 mmol) was added thereto. After dissolving the mixture with heating, the mixture was cooled in an ice bath to allow the mixture to crystallize. The crystals were filtered, washed with a small amount of ethanol, and dried at 80° C. in vacuo, to give N-cyclopropyl-6-[4-[(3-chlorophenyl)phenylmethyl]-1-piperazinyl]hexanesulfonamide fumarate (15.11 g) as colorless prisms (yield based on N-cyclopropyl-6-[4-[(3-chlorophenyl)phenylmethyl]-1-piperazinyl]hexanesulfonamide: 93.7%).

(1) Melting Point: 186°–188° C.

(2) Elemental Analysis (as C$_{26}$H$_{36}$ClN$_3$O$_2$S C$_4$H$_4$O$_4$)
Calculated: C, 59.44; H, 6.65; N, 6.93
Found: C, 59.22; H, 6.51; N, 7.05

Example 12

[Preparation of N-Cyclopropyl-6-[4-[(3-chlorophenyl)phenylmethyl]-1-piperazinyl]hexanesulfonamide dimaleate]

N-Cyclopropyl-6-[4-[(3-chlorophenyl)phenylmethyl]-1-piperazinyl]hexanesulfonamide (253 mg, 0.52 mmol) prepared in the same manner as in Example 1 was dissolved in methanol (15 ml). Maleic acid (138 mg, 1.19 mmol) was added thereto. After dissolving the mixture with heating, the solvent was removed by evaporation in vacuo. Acetone-diethyl ether was added to the residue, and the precipitated crystals were collected by filtration. The crystals were recrystallized from ethyl acetate, to give N-cyclopropyl-6-[4-[(3-chlorophenyl)phenylmethyl]-1-piperazinyl]hexanesulfonamide dimaleate (189 mg) as colorless prisms (yield based on N-cyclopropyl-6-[4-[(3-chlorophenyl)phenylmethyl]-1-piperazinyl)hexanesulfonamide: 50.3%).

(1) Melting Point: 106°–108° C.

(2) Elemental Analysis (as C$_{26}$H$_{36}$ClN$_3$O$_2$S 2C$_4$H$_4$O$_4$)
Calculated: C, 56.54; H, 6.14; N, 5.82
Found: C, 56.56; H, 6.07; N, 5.80

Example 13

[Preparation of N-Cyclopropyl-6-[4-[(3-chlorophenyl)phenylmethyl]-1-piperazinyl]hexanesulfonamide oxalate]

N-Cyclopropyl-6-[4-[(3-chlorophenyl)phenylmethyl]-1-piperazinyl]hexanesulfonamide (1.00 g, 2.04 mmol) prepared in the same manner as in Example 1 was dissolved in methanol (50 ml). Oxalic acid dehydrate (0.32 g, 2.55 mmol) was added thereto. After dissolving the mixture with heating, the solvent was removed by evaporation in vacuo. Acetone was added to the residue, and the precipitated crystals were collected by filtration. The crystals were recrystallized from acetone, to give N-cyclopropyl-6-[4-[(3-chlorophenyl)phenylmethyl]-1-piperazinyl]hexanesulfonamide oxalate (0.85 g) as colorless crystals (yield based on N-cyclopropyl-6-[4-[(3-chlorophenyl)phenylmethyl]-1-piperazinyl]hexanesulfonamide: 71.8%).

(1) Melting Point: 160°–162° C.
(2) Elemental Analysis (as $C_{26}H_{36}ClN_3O_2S \cdot C_2H_2O_4$)
Calculated: C, 57.97; H, 6.60; N, 7.24
Found: C, 58.21; H, 6.76; N, 7.12

Example 14

[Preparation of N-Cyclopropyl-6-[4-(3-chlorophenyl)phenylmethyl]-1-piperazinyl]hexanesulfonamide hydrochloride]

N-Cyclopropyl-6-[4-[(3-chlorophenyl)phenylmethyl]-1-piperazinyl]hexanesulfonamide (1.00 g, 2.04 mmol) prepared in the same manner as in Example 1 was dissolved in methanol (10 ml). 2 M hydrochloric acid (factor =1.004) (1.00 ml) was added thereto, and the solvent was then removed by evaporation in vacuo. Acetone was added to the residue, and the precipitated crystals were collected by filtration. The crystals were recrystallized from ethanol-acetone, to give N-cyclopropyl-6-[4-[(3-chlorophenyl)phenylmethyl]-1-piperazinyl]hexanesulfonamide hydrochloride (0.80 g) as colorless prisms (yield based on N-cyclopropyl-6-[4-[(3-chlorophenyl)phenylmethyl]-1-piperazinyl]hexanesulfonamide: 74.8%).

(1) Melting Point: 146°–150° C.
(2) Elemental Analysis (as $C_{26}H_{36}ClN_3O_2S \cdot HCl$)
Calculated: C, 59.30; H, 7.08; N, 7.98
Found: C, 59.15; H, 7.04; N, 7.87

Example 15

[Preparation of N-Cyclopropyl-6-[-4-[(3-chlorophenyl)phenylmethyl]-1-piperazinyl]hexanesulfonamide dihydrochloride]

N-Cyclopropyl-6-[4-[(3-chlorophenyl)phenylmethyl]-1-piperazinyl]hexanesulfonamide (1.00 g, 2.04 mmol) prepared in the same manner as in Example 1 was dissolved in methanol (10 ml). A 15% HCl-methanol solution was added thereto to make the solution acidic, and the solvent was then removed by evaporation in vacuo. Acetone was added to the residue, and the precipitated crystals were collected by filtration. The crystals were recrystallized from ethanol, to give N-cyclopropyl-6-[-4-[(3-chlorophenyl)phenylmethyl]-1-piperazinyl]hexanesulfonamide dihydrochloride (0.87 g) as colorless prisms (yield based on N-cyclopropyl-6-[-4-[(3-chlorophenyl)phenylmethyl]-1-piperazinyl]hexanesulfonamide: 75.7%).

(1) Melting Point: 160°–167° C.
(2) Elemental Analysis (as $C_{26}H_{36}ClN_3O_2S \cdot 2HCl$)
Calculated: C, 55.46; H, 6.80; N, 7.46
Found: C, 55.40; H, 6.94; N, 7.31

Example 16

[Preparation of N-Cyclopropyl-6-[-4-[(3-chlorophenyl)phenylmethyl]-1-piperazinyl]hexanesulfonamide dihydrobromide]

N-Cyclopropyl-6-[4-[(3-chlorophenyl)phenylmethyl]-1-piperazinyl]hexanesulfonamide (0.50 g, 1.02 mmol) prepared in the same manner as in Example 1 was dissolved in methanol (20 ml). A 47% hydrobromic acid solution (0.47 g, 2.75 mmol) was added thereto, and the solvent was then removed by evaporation in vacuo. Acetone was added to the residue, and the precipitated crystals were collected by filtration. The crystals were recrystallized from ethanol-acetone, to give N-cyclopropyl-6-[4-[(3-chlorophenyl)phenylmethyl]-1-piperazinyl]hexanesulfonamide dihydrobromide (0.46 g) as crystalline substances (yield based on N-cyclopropyl-6-[4-[(3-chlorophenyl)phenylmethyl]-1-piperazinyl]hexanesulfonamide: 69.2%).

(1) Melting Point: 202°–206° C.
(2) Elemental Analysis (as $C_{26}H_{36}ClN_3O_2S \cdot 2HBr$)
Calculated: C, 47.90; H, 5.57; N, 6.45
Found: C, 47.86; H, 5.78; N, 6.44

Example 17

[Preparation of N-Cyclopropyl-6-[4-[(4-chlorophenyl)phenylmethyl]-1-piperazinyl]hexanesulfonamide hydrochloride]

N-Cyclopropyl-6-[4-[(4-chlorophenyl)phenylmethyl]-1-piperazinyl]hexanesulfonamide (0.90 g, 1.84 mmol) prepared in the same manner as in Example 4 was dissolved in methanol (10 ml). 2 M hydrochloric acid (factor =1.004) (0.92 ml) was added thereto, and the solvent was then removed by evaporation in vacuo. Acetone was added to the residue, and the precipitated crystals were collected by filtration. The crystals were recrystallized from ethanol, to give N-cyclopropyl-6-[4-[(4-chlorophenyl)phenylmethyl]-1-piperazinyl]hexanesulfonamide hydrochloride (0.72 g) as colorless prisms (yield based on N-cyclopropyl-6-[4-[(4-chlorophenyl)phenylmethyl]-1-piperazinyl]hexanesulfonamide: 74.5%).

(1) Melting Point: 179°–181° C.
(2) Elemental Analysis (as $C_{26}H_{36}ClN_3O_2S \cdot HCl$)
Calculated: C, 59.30; H, 7.08; N, 7.98
Found: C, 59.04; H, 7.29; N, 8.00

Example 18

[Preparation of N-Cyclopropyl-6-[4-[(4-chlorophenyl)phenylmethyl]-1-piperazinyl]hexanesulfonamide dihydrochloride]

N-Cyclopropyl-6-[4-[(4-chlorophenyl)phenylmethyl]-1-piperazinyl]hexanesulfonamide (6.20 g, 12.65 mmol) prepared in the same manner as in Example 4 was dissolved in methanol (20 ml). 2 M Hydrochloric acid (factor 1.004) (15.00 ml) was added thereto, and the solvent was then removed by evaporation in vacuo. Acetone was added to the residue, and the precipitated crystals were collected by filtration. The crystals were recrystallized from acetone, to give N-cyclopropyl-6-[4-[(4-chlorophenyl)phenylmethyl]-1-piperazinyl]hexanesulfonamide dihydrochloride (5.60 g) as colorless prisms (yield based on N-cyclopropyl-6-[4-[(4-chlorophenyl)phenylmethyl]-1-piperazinyl]hexanesulfonamide: 78.6%).

(1) Melting Point: 140°–144° C.
(2) Elemental Analysis (as $C_{26}H_{36}ClN_3O_2S \cdot 2HCl$)
Calculated: C, 55.46; H, 6.80; N, 7.46
Found: C, 55.16; H, 6.99; N, 7.49

Example 19

[Preparation of N-(2-Hydroxyethyl)-6-[4-[(4-chlorophenyl)phenylmethyl]-1-piperazinyl]hexanesulfonamide]

1-[(4-Chlorophenyl)phenylmethyl]piperazine (573.6 mg, 2.00 mmol) and N-(2-hydroxyethyl)-6- chlorohexanesulfonamide (487.5 mg, 2.00 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(2-hydroxyethyl)-6-[4-[(4-chlorophenyl)phenylmethyl]-1-piperazinyl]hexanesulfonamide (904.4 mg) as a pale yellow oil (yield: 91.5%).

(1) IR vmax (neat) cm$^{-}$: 3509 (OH), 3286 (NH), 1320, 1143 (SO$_2$)

(2) Mass Spectroscopy (C$_{25}$H$_{36}$ClN$_3$O$_3$S) EI: m/z 493 [M]$^+$ (3) EI-HRMS (C$_{25}$H$_{36}$ClN$_3$O$_3$S)
Calculated: 493.2164, Found: 493.2172

(4) $^1$H-NMR (CDCl$_3$) δ: 1.28–1.58 (6 H, m, NCH$_2$CH$_2$CH$_2$), 1.74–1.90 (2 H, m, SCH$_2$CH$_2$), 2.07 (1 H, brs, OH), 2.34 (2 H, t, J=7.9 Hz, NCH$_2$), 2.38–2.52 (8 H, m, NCH$_2$CH$_2$x2), 3.02–3.08 (2 H, m, SCH$_2$), 3.27 (2 H, brs, NCH$_2$CH$_2$OH), 3.75 (2 H, t, J=5.2 Hz, NCH$_2$CH$_2$OH), 4.22 (1 H, s, CH), 4.79 (1 H, brs, NH), 7.15–7.44 (9 H, m, ArH)

Example 20

[Preparation of N-(2-Hydroxyethyl)-6-[4-[(4-chlorophenyl phenylmethyl]-1-piperazinyl] hexanesulfonamide dihydrochloride]

N-(2-Hydroxyethyl)-6-[4-[(4-chlorophenyl) phenylmethyl]-1-piperazinyl]hexanesulfonamide (7.75 g, 15.69 mmol) prepared in the same manner as in Example 19 was dissolved in ethanol. A 15% HCl-methanol solution was added thereto to make it acidic, and the solvent was removed by evaporation in vacuo. Diethyl ether was added to the residue, and the precipitated crystals were collected by filtration. The crystals were recrystallized from ethanol, to give N-(2-hydroxyethyl)-6-[4-[(4-chlorophenyl) phenylmethyl]-1-piperazinyl]hexanesulfonamide dihydrochloride (8.10 g) as colorless prisms (yield: 91.1%).

(1) Melting Point: 136°–142° C.

(2) Elemental Analysis (as C$_{25}$H$_{36}$ClN$_3$O$_3$S 2HCl)
Calculated: C, 52.95; H, 6.76; N, 7.41
Found: C, 52.86; H, 6.82; N, 7.53

Example 21

[Preparation of N-(2-Hydroxyethyl)-5-[4-[(4-chlorophenyl)phenylmethyl]-1-piperazinyl] pentanesulfonamide]

1-[(4-Chlorophenyl)phenylmethyl]piperazine (573.6 mg, 2.00 mmol) and N-(2-hydroxyethyl)-5-chloropentanesulfonamide (459.5 mg, 2.00 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(2-hydroxyethyl)-5-[4-[(4-chlorophenyl)phenylmethyl]-1-piperazinyl]pentanesulfonamide (877.0 mg) as a pale yellow oil (yield: 91.4%).

(1) IR vmax (neat) cm$^{-1}$: 3509 (OH), 3282 (NH), 1318, 1143 (SO$_2$)

(2) Mass Spectroscopy (C$_{24}$H$_{34}$ClN$_3$O$_3$S) EI: m/z 479 [M]$^+$ (3) EI-HRMS (C$_{24}$H$_{34}$ClN$_3$O$_3$S)
Calculated: 479.2008, Found: 479.2005

(4) $^1$H-NMR (CDCl$_3$) δ: 1.40–1.59 (4 H, m, NCH$_2$CH$_2$CH$_2$), 1.76–1.91 (2 H, m, SCH$_2$CH$_2$), 1.97 (1 H, brs, OH), 2.36 (2 H, t, J=7.5 Hz, NCH$_2$), 2.39–2.54 (8 H, m, NCH$_2$CH$_2$x2), 3.04–3.09 (2 H, m, SCH$_2$), 3.27 (2 H, brs, NCH$_2$CH$_2$OH), 3.75 (2 H, t, J=5.2 Hz, NCH$_2$CH$_2$OH), 4.23 (1 H, s, CH), 4.81 (1 H, brs, NH), 7.18–7.39 (9 H, m, ArH)

Example 22

[Preparation of N-(2-Hydroxyethyl)-12-[4-[(4-chlorophenyl)phenylmethyl]-1-piperazinyl] dodecanesulfonamide]

1-[(4-Chlorophenyl)phenylmethyl]piperazine (610.0 mg, 2.12 mmol) and N-(2-hydroxyethyl)-12-bromododecanesulfonamide (871.0 mg, 2.34 mmol) obtained in Preparation Example 6 were refluxed in N-ethyldiisopropylamine (2 ml) for 4 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(2-hydroxyethyl)-12-[4-[(4-chlorophenyl)phenylmethyl]-1-piperazinyl]dodecanesulfonamide (1125.0 mg) as a pale brown oil (yield based on 1-[(4-chlorophenyl)phenylmethyl] piperazine: 91.7%).

(1) IR vmax (neat) cm$^{-1}$: 3509 (OH), 3286 (NH), 1321, 1144 (SO$_2$)

(2) Mass Spectroscopy (C$_{31}$H$_{48}$ClN$_3$O$_3$S) EI: m/z 577 [M]$^+$ (3) EI-HRMS (C$_{31}$H$_{48}$ClN$_3$O$_3$S)
Calculated: 577.3102, Found: 577.3112

(4) $^1$H-NMR (CDCl$_3$) δ: 1.22–1.54 (18 H, m, NCH$_2$(CH$_2$)$_9$CH$_2$CH$_2$S), 1.77–1.89 (3 H, m, SCH$_2$CH$_2$OH), 2.35 (2 H, t, J=8.0 Hz, NCH$_2$), 2.38–2.54 (8 H, m, NCH$_2$CH$_2$x2), 3.03–3.09 (2 H, m, SCH$_2$), 3.24–3.33 (2 H, brs, NCH$_2$CH$_2$OH), 3.78 (2 H, t, J=5.2 Hz, NCH$_2$CH$_2$OH), 4.23 (1 H, s, CH), 4.65 (1 H, brs, NH), 7.17–7.40 (9 H, m, ArH)

Example 23

[Preparation of N-(3-Hydroxypropyl)-6-[4-[(4-chlorophenyl)phenylmethyl]-1-piperazinyl] hexanesulfonamide]

1-[(4-Chlorophenyl)phenylmethyl]piperazine (505.9 mg, 1.76 mmol) and N-(3-hydroxypropyl)-6-chlorohexanesulfonamide (500.0 mg, 1.94 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(3- hydroxypropyl)-6-[4-[(4-chlorophenyl)phenylmethyl]-1-piperazinyl]hexanesulfonamide (819.3 mg) as a pale yellow oil (yield based on 1-[(4-chlorophenyl)phenylmethyl]piperazine: 91.4%).

(1) IR vahax (neat) cm$^{-1}$: 3509 (OH), 3286 (NH), 1320, 1143 (SO$_2$)

(2) Mass Spectroscopy (C$_{26}$H$_{38}$ClN$_3$O$_3$S) EI: d/z 507 [M]$^+$ (3) EI-HRMS (C$_{26}$H$_{38}$ClN$_3$O$_3$S)
Calculated: 507.2320, Found: 507.2313

(4) $^1$H-NMR (CDCl$_3$) δ: 1.27–1.58 (6 H, m, NCH$_2$CH$_2$CH$_2$CH$_2$), 1.74–1.88 (4 H, mn, SCH$_2$CH$_2$, NCH$_2$CH$_2$CH$_2$OH), 2.19 (1 H, brs, OH), 2.34 (2 H, t, J=7.9 Hz, NCH$_2$), 2.38–2.53 (8 H, m, NCH$_2$CH$_2$x2), 2.99–3.05 (2 H, SCH$_2$), 3.25–3.31 (2 H, m, NCH$_2$CH$_2$CH$_2$OH), 3.79 (2 H, t, J=5.6 Hz, NCH$_2$CH$_2$CH$_2$H), 4.22 (1 H, s, CH), 4.76–4.84 (1 H, m, NH), 7.20–7.39 (9 H, m, ArH)

Example 24

[preparation of N-(3-Hydroxypropyl)-5-[4-[(4-chlorophenyl)phenylmethyl]-1-piperazinyl]pentanesulfonamide]

1-[(4-Chlorophenyl)phenylmethyl]piperazine (573.6 mg, 2.00 mmol) and N-(3-hydroxypropyl)-5-chloropentanesulfonamide (487.5 mg, 2.00 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(3-hydroxypropyl)-5-[4-[(4-chlorophenyl)phenylmethyl]-1-piperazinyl]pentanesulfonamide (940.0 mg) as a pale yellow oil (yield: 95.1%).

(1) IR vmax (neat) cm$^{-1}$: 3509 (OH), 3281 (NH), 1318, 1143 (SO$_2$)

(2) Mass Spectroscopy (C$_{25}$H$_{36}$ClN$_3$O$_3$S) EI: m/z 493 [M]$^+$ (3) EI-HRMS (C$_{25}$H$_{36}$ClN$_3$O$_3$S)
Calculated: 493.2163, Found: 493.2161

(4) $^1$H-NMR (CDCl$_3$) δ: 1.39–1.60 (4 H, m, NCH$_2$CH$_2$CH$_2$), 1.72–1.90 (4 H, m, SCH$_2$CH$_2$, NCH$_2$CH$_2$CH$_2$OH), 2.05 (1 H, brs, OH), 2.37 (2 H, t, J=7.4 Hz, NCH$_2$), 2.40–2.55 (8 H, m, NCH$_2$CH$_2$x2), 3.01–3.06 (2 H, m, SCH$_2$), 3.22–3.33 (2 H, m, NCH$_2$CH$_2$CH$_2$OH), 3.78 (2 H, t, J=5.7 Hz, NCH$_2$CH$_2$CH$_2$OH), 4.23 (1 H, s, CH), 4.84–4.94 (1 H, in, NH), 7.17–7.42 (9 H, m, ArH)

Example 25

[Preparation of N-(4-Hydroxybutyl)-6-[4-[(4-chlorophenyl)phenylmethyl]-1-piperazinyl]hexanesulfonamide]

1-[(4-Chlorophenyl)phenylmethyl]piperazine (479.8 mg, 1.67 mmol) and N-(4-hydroxybutyl)-6-chlorohexanesulfonamide (500.0 mg, 1.84 mmol) prepared in Preparation Example 22 were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(4-hydroxybutyl)-6-[4-[(4-chlorophenyl)phenylmethyl]-1-piperazinyl]hexanesulfonamide (828.6 mg) as a pale yellow oil (yield based on 1-[(4-chlorophenyl)phenylmethyl]piperazine: 94.9%).

(1) IR vmax (neat) cm$^{-1}$: 3509 (OH), 3286 (NH), 1321, 1143 (SO$_2$)

(2) Mass Spectroscopy (C$_{27}$H$_{40}$ClN$_3$O$_3$S) EI: m/z 521 [M]$^+$ (3) EI-HRMS (C$_{27}$H$_{40}$ClN$_3$O$_3$S)
Calculated: 521.2477, Found: 521.2483

(4) $^1$H-NMR (CDCl$_3$) δ: 1.28–1.56 (6 H, m, NCH$_2$CH$_2$CH$_2$CH$_2$), 1.59–1.72 (4 H, m, NCH$_2$CH$_2$CH$_2$CH$_2$OH), 1.74–1.87 (2 H, m, SCH$_2$CH$_2$), 2.01 (1 H, brs, OH), 2.34 (2 H, t, J=7.9 Hz, NCH$_2$), 2.38–2.53 (8 H, m, NCH$_2$CH$_2$x2), 2.98–3.03 (2 H, m, SCH$_2$), 3.12–3.21 (2 H, m, NCH$_2$CH$_2$CH$_2$CH$_2$OH), 3.68 (2 H, t, J=5.7 Hz, NCH$_2$CH$_2$CH$_2$CH$_2$OH), 4.23 (1 H, s, CH), 4.65–4.76 (1 H, m, NH), 7.18–7.39 (9 H, m, ArH)

Example 26

[Preparation of N-(4-Hydroxybutyl)-5-[4-[(4-chlorophenyl)phenylmethyl]-piperazinyl]pentanesulfonamide]

1-[(4-Chlorophenyl)phenylmethyl]piperazine (573.6 mg, 2.00 mmol) and N-(4-hydroxybutyl)-5-chloropentanesulfonamide (515.6 mg, 2.00 mmol) prepared in Preparation Example 23 were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(4-hydroxybutyl)-5-[4-[(4-chlorophenyl)phenylmethyl]-1-piperazinyl]pentanesulfonamide (947.0 mg) as a pale yellow oil (yield: 93.2%).

(1) IR vmax (neat) cm$^{-1}$: 3509 (OH), 3282 (NH), 1318, 1143 (SO$_2$)

(2) Mass Spectroscopy (C$_{26}$H$_{38}$ClN$_3$O$_3$S) EI: m/z 507 [M]$^+$ (3) EI-HRMS (C$_{26}$H$_{38}$ClN$_3$O$_3$S)
Calculated: 507.2320, Found: 507.2317

(4) $^1$H-NMR (CDCl$_3$) δ: 1.37–1.58 (4 H, m, NCH$_2$CH$_2$CH$_2$), 1.58–1.75 (4 H, m, NCH$_2$CH$_2$CH$_2$CH$_2$OH), 1.75–1.99 (3 H, m, SCH$_2$CH$_2$, OH), 2.36 (2 H, t, J=7.6 Hz, NCH$_2$), 2.37–2.54 (8 H, m, NCH$_2$CH$_2$x2), 2.98–3.04 (2 H, m, SCH$_2$), 3.10–3.25 (2 H, m, NCH$_2$CH$_2$CH$_2$CH$_2$OH), 3.69 (2 H, t, J=5.7 Hz, NCH$_2$CH$_2$CH$_2$CH$_2$OH), 4.23 (1 H, s, CH), 4.68–4.80 (1 H, m, NH), 7.17–7.42 (9 H, m, ArH)

Example 27

[Preparation of N-(2-Hydroxyethyl)-6-[4-[bis(4-fluorophenyl)methyl]-1-piperazinyl]hexanesulfonamide]

1-[Bis(4-fluorophenyl)methyl]piperazine (576.7 mg, 2.00 mmol) and N-(2-hydroxyethyl)-6-chlorohexanesulfonamide (487.5 mg, 2.00 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(2-hydroxyethyl)-6-[4-[bis(4-fluorophenyl)methyl]-1-piperazinyl]hexanesulfonamide (915.2 mg) as a pale yellow oil (92.3%).

(1) IR vmax (neat) cm$^{-1}$: 3502 (OH), 3287 (NH), 1320, 1143 (SO$_2$)

(2) Mass Spectroscopy (C$_{25}$H$_{35}$F$_2$N$_3$O$_3$S) EI: m/z 495 [M]$^+$ (3) EI-HRMS (C$_{25}$H$_{35}$F$_2$N$_3$O$_3$S)
Calculated: 495.2365, Found: 495.2362

(4) $^1$H-NMR (CDCl$_3$) δ: 1.28–1.57 (6 H, m, NCH$_2$CH$_2$CH$_2$CH$_2$), 1.77–1.90 (2 H, m, SCH$_2$CH$_2$), 2.07 (1 H, brs, OH), 2.34 (2 H, t, J=7.9 Hz, NCH$_2$), 2.37–2.53 (8 H, m, NCH$_2$CH$_2$x2), 3.02–3.08 (2 H, m, SCH$_2$), 3.27 (2 H, brs, NCH$_2$CH$_2$OH), 3.75 (2 H, t, J=5.2 Hz, NCH$_2$CH$_2$OH), 4.23 (1 H, s, CH), 4.78 (1 H, brs, NH), 6.95–7.02 (4 H, m, ArH), 7.32–7.37 (4 H, m, ArH)

Example 28

[Preparation of N-(2-Hydroxvethyl)-5-[4-[bis(4-fluorophenyl)methyl]-1-piperazinyl] pentanesulfonamide]

1-[Bis(4-fluorophenyl)methyl]piperazine (576.7 mg, 2.00 mmol) and N-(2-hydroxyethyl)-5-chloropentanesulfonamide (459.5 mg, 2.00 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(2-hydroxyethyl)-5-[4-[bis(4-fluorophenyl)methyl]-1-piperaziny]pentanesulfonamide (905.6 mg) as a pale yellow oil (94.0%).

(1) IR vmax (neat) cm$^{-1}$: 3509 (OH), 3286 (NH), 1321, 1144 (SO$_2$) (2) Mass Spectroscopy (C$_{24}$H$_{33}$F$_2$N$_3$O$_3$S) EI: m/z 481 [M]$^{+}$(3) EI-HRMS (C$_{24}$H$_{33}$F$_2$N$_2$O$_3$S)
Calculated: 481.2209, Found: 481.2212

(4) $^1$H-NMR (CDCl$_3$) δ: 1.40–1.57 (4 H, m, NCH$_2$CH$_2$CH$_2$), 1.79–1.91 (2 H, m, SCH$_2$CH$_2$), 2.10–2.30 (1 H, br, OH), 2.36 (2 H, t, J=7.5 Hz, NCH$_2$), 2.40–2.53 (8 H, in, NCH$_2$CH$_2$x2), 3.04–3.09 (2 H, in, SCH$_2$), 3.27 (2 H, brs, NCH$_2$CH$_2$OH), 3.75 (2 H, t, J=5.2 Hz, NCH$_2$CH$_2$OH), 4.23 (1 H, s, CH), 4.84 (1 H, brs, NH), 6.95–7.02 (4 H, m, ArH), 7.33–7.38 (4 H, in, ArH)

Example 29

[Preparation of N-(3-Hydroxypropyl)-6-[4-[bis(4-fluorophenyl)methyl]-1-piperazinyl] hexanesulfonamide]

1-[Bis(4-fluorophenyl)methyl]piperazine (576.7 mg, 2.00 mmol) and N-(3-hydroxypropyl)-6-chlorohexanesulfonamide (515.6 mg, 2.00 mmol) were refluxed in N-ethyldiisopropylamine (2 ml) for 6 hours. The reaction mixture was concentrated in vacuc, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(3-hydroxypropyl)-6-[4-[bis(4-fluorophenyl)methyl]-1-piperazinyl]hexanesulfonamide (976.6 mg) as a pale yellow oil (95.8%).

(1) IR vmax (neat) cm$^{-1}$: 3502 (OH), 3286 (NH), 1320, 1144 (SO$_2$)

(2) Mass Spectroscopy (C$_{26}$H$_{37}$F$_2$N$_3$O$_3$S) EI: m/z 509 [M]$^+$ (3) EI-HRMS (C$_{26}$H$_{37}$F$_2$N$_3$O$_3$S)
Calculated: 509.2522, Found: 509.2522

(4) $^1$H-NMR (CDCl$_3$) δ: 1.28–1.58 (6 H, m, NCH$_2$CH$_2$CH$_2$CH$_2$), 1.75–1.88 (4 H, m, SCH$_2$CH$_2$, NCH$_2$CH$_2$CH$_2$OH), 2.00–2.30 (1 H, br, OH), 2.34 (2 H, t, J=7.9 Hz, NCH$_2$), 2.37–2.52 (8 H, m, NCH$_2$CH$_2$x2), 2.99–3.05 (2 H, m, SCH$_2$), 3.25–3.31 (2 H, m, NCH$_2$CH$_2$OH), 3.79 (2 H, t, J=5.7 Hz, NCH$_2$CH$_2$OH), 4.23 (1 H, s, CH), 4.73–4.82 (1 H, m, NH), 6.95–7.02 (4 H, m, ArH), 7.33–7.38 (4 H, m, ArH)

Example 30

[Preparation of N-(3-Hydroxypropyl)-5-[4-[bis(4-fluorophenyl)methyl]-1-piperazinyl] pentanesulfonamide]-1-[Bis(4-fluorophenyl)methyl] piperazine (576.7 mg, 2.00 mmol) and N-(3-hydroxypropyl)-5-chloropentanesulfonamide (487.5 mg, 2.00 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(3-hydroxypropyl)-5-[4-[bis(4-fluorophenyl)methyl]-1-piperazinyl]pentanesulfonamide (913.0 mg) as a pale yellow oil (92.1%).

(1) IR vmax (neat) cm$^{-1}$: 3502 (OH), 3287 (NH), 1318, 1144 (SO$_2$)

(2) Mass Spectroscopy (C$_{25}$H$_{35}$F$_2$N$_3$O$_3$S) EI: m/z 495 [M]$^+$ (3) EI-HRMS (C$_{25}$H$_{35}$F$_2$N$_3$O$_3$S)
Calculated: 495.2365, Found: 495.2364

(4) $^1$H-NMR (CDCl$_3$) δ: 1.41–1.58 (4 H, m, NCH$_2$CH$_2$CH$_2$), 1.75–1.89 (4 H, m, SCH$_2$CH$_2$, NCH$_2$CH$_2$CH$_2$OH), 2.36 (2 H, t, J=7.3 Hz, NCH$_2$), 2.38–2.53 (8 H, m, NCH$_2$CH$_2$x2), 3.01–3.05 (2 H, m, SCH$_2$), 3.25–3.31 (2 H, m, NCH$_2$CH$_2$CH$_2$OH), 3.79 (2 H, t, J=5.6 Hz, NCH$_2$CH$_2$CH$_2$OH), 4.23 (1 H, s, CH), 4.81–4.89 (1 H, m, NH), 6.95–7.02 (4 H, m, ArH), 7.33–7.38 (4 H, m, ArH)

Example 31

[Preparation of N-(4-Hydroxybutyl)-6-[4-[bis(4-fluorophenyl)methyl]-1-piperazinyl] hexanesulfonamide]

1-[Bis(4-fluorophenyl)methyl]piperazine (576.7 mg, 2.00 mmol) and N-(4-hydroxybutyl)-6-chlorohexanesulfonamide (543.6 mg, 2.00 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(4-hydroxybutyl)-6-[4-[bis(4-fluorophenyl)methyl]-1-piperazinyl]hexanesulfonamide (1001.2 mg) as a pale yellow oil (95.6%).

(1) IR vmax (neat) cm$^{-1}$: 3502 (OH), 3286 (NH), 1321, 1144 (SO$_2$)
(2) Mass Spectroscopy (C$_{27}$H$_{39}$F$_2$N$_3$O$_3$S) EI: m/z 523 [M]$^+$
(3) EI-HRMS (C$_{27}$H$_{39}$F$_2$N$_3$O$_3$S)
Calculated: 523.2678, Found: 523.2679
(4) $^1$H-NMR (CDCl$_3$) δ: 1.28–1.57 (6 H, m, NCH$_2$CH$_2$CH$_2$CH$_2$), 1.60–1.75 (4 H, m, NCH$_2$CH$_2$CH$_2$CH$_2$OH), 1.75–1.87 (2 H, m, SCH$_2$CH$_2$), 2.07 (1 H, br, OH), 2.33 (2 H, t, J=7.9 Hz, NCH$_2$), 2.37–2.53 (8 H, m, NCH$_2$CH$_2$x2), 2.98–3.03 (2 H, m, SCH$_2$), 3.12–3.21 (2 H, m, NCH$_2$CH$_2$CH$_2$CH$_2$OH), 3.68 (2 H, t, J=5.7 Hz, NCH$_2$CH$_2$CH$_2$CH$_2$OH), 4.23 (1 H, s, CH), 4.68–4.76 (1 H, m, NH), 6.95–7.02 (4 H, m, ArH), 7.32–7.38 (4 H, m, ArH)

Example 32

[Preparation of N-(4-Hydroxybutyl)-5-[4-[bis(4-fluorophenyl)methyl]-1-piperazinyl] pentanesulfonamide]

1-[Bis(4-fluorophenyl)methyl]piperazine (576.7 mg, 2.00 mmol) and N-(4-hydroxybutyl)-5-chloropentanesulfonamide (515.6 mg, 2.00 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(4-hydroxybutyl)-5-[4-[bis(4-fluorophenyl)methyl]-1-piperazinyl]pentanesulfonamide (934.3 mg) as a pale yellow oil (91.7%).

(1) IR vmax (neat) cm$^{-1}$: 3502 (OH), 3286 (NH), 1320, 1144 (SO$_2$)
(2) Mass Spectroscopy (C$_{26}$H$_{37}$F$_2$N$_3$O$_3$S) EI: m/z 509 [M]$^+$
(3) EI-HRMS (C$_{26}$H$_{37}$F$_2$N$_3$O$_3$S)
Calculated: 509.2522, Found: 509.2520
(4) $^1$H-NMR (CDCl$_3$) δ: 1.40–1.57 (4 H, m, NCH$_2$CH$_2$CH$_2$), 1.60–1.75 (4 H, m, NCH$_2$CH$_2$CH$_2$CH$_2$OH), 1.77–1.89 (2 H, m, SCH$_2$CH$_2$), 1.92 (1 H, brs, OH), 2.35 (2 H, t, J=7.6 Hz, NCH$_2$), 2.37–2.52 (8 H, m, NCH$_2$CH$_2$x2), 2.99–3.04 (2 H, m, SCH$_2$), 3.13–3.21 (2 H, m, NCH$_2$CH$_2$CH$_2$CH$_2$OH), 3.69 (2 H, t, J=5.8 Hz, NCH$_2$CH$_2$CH$_2$CH$_2$OH), 4.23 (1 H, s, CH), 4.68–4.77 (1 H, m, NH), 6.95–7.02 (4 H, m, ArH), 7.32–7.38 (4 H, m, ArH)

Example 33

[Preparation of N-(2-Hydroxyethyl)-6-[4-[bis(4-chlorophenyl)methyl]-1-Piperazinyl] hexanesulfonamide]

1-[Bis(4-chlorophenyl)methyl]piperazine (642.5 mg, 2.00 mmol) and N-(2-hydroxyethyl)-6-chlorohexanesulfonamide (487.5 mg, 2.00 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(2-hydroxyethyl)-6-[4-[bis(4-chlorophenyl)methyl]-1-piperazinyl]hexanesulfonamide (975.0 mg) as a pale brown oil (92.2%).

(1) IR vmax (neat) cm$^{-1}$: 3509 (OH), 3282 (NH), 1321, 1143 (SO$_2$)
(2) Mass Spectroscopy (C$_{25}$H$_{35}$Cl$_2$N$_3$O$_3$S) EI: m/z 527 [M]$^+$
(3) EI-HRMS (C$_{25}$H$_{35}$Cl$_2$N$_3$O$_3$S)
Calculated: 527.1774, Found: 527.1771
(4) $^1$H-NMR (CDCl$_3$) δ: 1.27–1.56 (6 H, m, NCH$_2$CH$_2$CH$_2$CH$_2$), 1.65–2.00 (3 H, mn, SCH$_2$CH$_2$, OH), 2.34 (2 H, t, J=7.9 Hz, NCH$_2$), 2.37–2.55 (8 H, m, NCH$_2$CH$_2$x2), 3.03–3.08 (2 H, m, SCH$_2$), 3.22–3.33 (2 H, m, NCH$_2$CH$_2$OH), 3.76 (2 H, t, J=5.2 Hz, NCH$_2$CH$_2$OH), 4.21 (1 H, s, CH), 4.74 (1 H, brs, NH), 7.22–7.38 (8 H, m, ArH)

Example 34

[Ppreparation of N-(2-Hydroxyethyl)-5-[4-[bis(4-chlorophenyl)methyl]-1-piperazinyl] pentanesulfonamide]

1-[Bis(4-chlorophenyl)methyl]piperazine (642.5 mg, 2.00 mmol) and N-(2-hydroxyethyl)-5-chloropentanesulfonamide (459.5 mg, 2.00 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give N-(2-hydroxyethyl)-5-[4-[bis(4-chlorophenyl)methyl]-1-piperazinyl]pentanesulfonamide (1003.0 mg) as a pale brown oil (97.5%).

(1) IR vmax (neat) cm$^{-1}$: 3509 (OH), 3282 (NH), 1320, 1144 (SO$_2$)
(2) Mass Spectroscopy (C$_{24}$H$_{33}$Cl$_2$N$_3$O$_3$S) EI: m/z 513 [M]$^+$
(3) EI-HRMS (C$_{24}$H$_{33}$Cl$_2$N$_3$O$_3$S)
Calculated: 513.1618, Found: 513.1604
(4) $^1$H-NMR (CDCl$_3$) δ: 1.39–1.58 (4 H, m, NCH$_2$CH$_2$CH$_2$), 1.64–2.30 (3 H, m, SCH$_2$CH$_2$, OH), 2.34 (2 H, t, J=7.5 Hz, NCH$_2$), 2.38–2.53 (8 H, m, NCH$_2$CH$_2$x2), 3.04–3.09 (2 H, m, SCH$_2$), 3.23–3.32 (2 H, m, NCH$_2$CH$_2$OH), 3.76 (2 H, t, J=5.2 Hz, NCH$_2$CH$_2$OH), 4.21 (1 H, s, CH), 4.79 (1 H, brs, NH), 7.25–7.34 (8 H, m, ArH)

Example 35

[Preparation of N-Cyclopropyl-10-[4-[(4-chlorophenyl)phenylmethyl]-1-piperazinyl] decanesulfonamide]

1-[(4-Chlorophenyl)phenylmethyl]piperazine (525.0 mg, 1.83 mmol) and N-cyclopropyl-10- bromodecanesulfonamide (685.0 mg, 2.01 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform, to give N-cyclopropyl-10-[4-[(4-chlorophenyl)phenylmethyl]-1-piperazinyl] decanesulfonamide (964.0 mg) as a pale brown oil (yield based on 1-[(4-chlorophenyl)phenylmethyl]piperazine: 96.5%).

(1) IR vmax (neat) cm$^{-1}$: 3275 (NH), 1318, 1146 (SO$_2$)
(2) Mass Spectroscopy (C$_{30}$H$_{44}$ClN$_3$O$_2$S) EI: m/z 545 [M]$^+$
(3) EI-HRMS (C$_{30}$H$_{44}$ClN$_3$O$_2$S)
Calculated: 545.2840, Found: 545.2837
(4) $^1$H-NMR (CDCl$_3$) δ: 0.67–0.83 (4 H, m, CHCH$_2$CH$_2$), 1.23–1.57 (14 H, m, NCH$_2$(CH$_2$)$_7$CH$_2$CH$_2$S), 1.72–1.91 (2 H, m, SCH$_2$CH$_2$), 2.34 (2 H, t, J=8.2 Hz, NCH$_2$), 2.39–2.55 (8 H, m, NCH$_2$CH$_2$x2), 2.56–2.63 (1 H, m, CHCH$_2$CH$_2$), 3.05–3.10 (2 H, m, SCH$_2$), 4.22 (1 H, s, CH), 4.65 (1 H, brs, NH), 7.17–7.48 (9 H, m, ArH)

Example 36

[Preparation of N-Cyclopropyl-11-[4-[(4-chlorophenyl)phenylmethyl]-1-piperazinyl] undecanesulfonamide]

1-[(4-Chlorophenyl)phenylmethyl]piperazine (642.7 mg, 2.24 mmol) and N-cyclopropyl-11-bromoundecanesulfonamide (873.0 mg, 2.46 mmol) were refluxed in N-ethyldiisopropylamine (2 ml) for 4 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform, to give N-cyclopropyl-11-[4-[(4-chlorophenyl)phenylmethyl]-1-piperazinyl] undecanesulfonamide (1210.0 mg) as a pale yellow oil (yield based on 1-[(4-chlorophenyl)phenylmethyl] piperazine: 96.4%).

(1) IR vmax (neat) cm$^{-1}$: 3274 (NH), 1318, 1147 (SO$_2$)
(2) Mass Spectroscopy (C$_{31}$H$_{46}$ClN$_3$O$_2$S) EI: m/z 559 [M]$^+$
(3) EI-HRMS (C$_{31}$H$_{46}$ClN$_3$O$_2$S)
Calculated: 559.2997, Found: 559.2990
(4) $^1$H-NMR (CDCl$_3$) δ: 0.68–0.77 (4 H, m, CHCH$_2$CH$_2$), 1.23–1.53 (16 H, m, NCH$_2$(CH$_2$)$_8$CH$_2$CH$_2$S), 1.76–1.87 (2 H, m, SCH$_2$CH$_2$), 2.33 (2 H, t, J=7.9 Hz, NCH$_2$), 2.37–2.53 (8 H, m, NCH$_2$CH$_2$x2), 2.55–2.63 (1 H, m, CHCH$_2$CH$_2$), 3.05–3.11 (2 H, m, SCH$_2$), 4.22 (1 H, s, CH), 4.60 (1 H, brs, NH), 7.16–7.41 (9 H, m, ArH)

Example 37

[Preparation of N-Cyclopropyl-12-[4-[(4-chlorophenyl)phenylmethyl]-1-piperazinyl] dodecanesulfonamide]

1-[(4-Chlorophenyl)phenylmethyl]piperazine (629.0 mg, 2.20 mmol) and N-cyclopropyl-12- bromododecanesulfonamide (891.0 mg, 2.42 mmol) were refluxed in N-ethyldiisopropylamine (2 ml) for 4 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform, to give N-cyclopropyl-12-[4-[(4-chlorophenyl)phenylmethyl]-1-piperazinyl] dodecanesulfonamide (1243.0 mg) as a pale brown oil (yield based on 1-[(4-chlorophenyl)phenylmethyl]piperazine: 98.4%).

(1) IR vmax (neat) cm$^{-1}$: 3274 (NH), 1318, 1146 (SO$_2$)
(2) Mass Spectroscopy (C$_{32}$H$_{48}$ClN$_3$O$_2$S) EI: m/z 573 [M]$^+$
(3) EI-HRMS (C$_{32}$H$_{48}$ClN$_3$O$_2$S)
Calculated: 573.3153, Found: 573.3152
(4) $^1$H-NMR (CDCl$_3$) δ: 0.67–0.78 (4 H, m, CHCH$_2$CH$_2$), 1.22–1.53 (18 H, m, NCH$_2$(CH$_2$)$_9$CH$_2$CH$_2$S), 1.76–1.87 (2 H, m, SCH$_2$CH$_2$), 2.33 (2 H, t, J=8.0 Hz, NCH$_2$), 2.37–2.54 (8 H, m, NCH$_2$CH$_2$x2), 2.54–2.63 (1 H, m, CHCH$_2$CH$_2$), 3.05–3.11 (2 H, m, SCH$_2$), 4.22 (1 H, s, CH), 4.63 (1 H, brs, NH), 7.16–7.40 (9 H, m, ArH)

Example 38

[Preparation of N,N-Dimethyl-6-[4-[(4-chlorophenyl)phenylmethyl]-1-piperazinyl] hexanesulfonamide]

1-[(4-Chlorophenyl)phenylmethyl]piperazine (573.6 mg, 2.00 mmol) and N,N-dimethyl-6-chlorohexanesulfonamide (455.5 mg, 2.00 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (50:1), to give N,N-dimethyl-6-[4-[(4-chlorophenyl)phenylmethyl]1-piperazinyl] hexanesulfonamide (880.0 mg) as a pale brown oil (yield: 92.1%).

(1) IR vmax (neat) cm$^{-1}$: 1329, 1139 (SO$_2$)
(2) Mass Spectroscopy (C$_{25}$H$_{36}$ClN$_3$O$_2$S) EI: m/z 477 [M]$^+$
(3) EI-HRMS (C$_{25}$H$_{36}$ClN$_3$O$_2$s)
Calculated: 477.2215, Found: 477.2219
(4) $^1$H-NMR (CDCl$_3$) δ: 1.27–1.55 (6 H, m, NCH$_2$CH$_2$CH$_2$CH$_2$), 1.76–1.88 (2 H, m, SCH$_2$CH$_2$), 2.34 (2 H, t, J=7.9 Hz, NCH$_2$), 2.38–2.54 (8 H, m, NCH$_2$CH$_2$x2), 2.88 (6 H, s, CH$_3$x2), 2.88–2.94 (2 H, m, SCH$_2$), 4.22 (1 H, s, CH), 7.16–7.40 (9 H, m, ArH)

Example 39

[Preparation of N,N-Dimethyl-5-[4-[(4-chlorophenyl)phenylmethyl]-1-piperazinyl] pentanesulfonamide]

1-[(4-Chlorophenyl)phenylmethyl]piperazine (573.6 mg, 2.00 mmol) and N,N-dimethyl-5-chloropentanesulfonamide (470.2 mg, 2.20 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (50:1), to give N,N-dimethyl-5-[4-[(4-chlorophenyl)phenylmethyl]-1-piperazinyl] pentanesulfonamide (857.7 mg) as a yellow oil (yield based on 1-[(4-chlorophenyl)phenylmethyl]piperazine: 92.4%).

(1) IR vmax (neat) cm$^{-1}$: 1336, 1148 ($SO_2$)

(2) Mass Spectroscopy ($C_{24}H_{34}ClN_3O_2S$) EI: m/z 463 [M]$^+$ (3) EI-HRMS ($C_{24}H_{34}ClN_3O_2S$)
Calculated: 463.2059, Found: 463.2067

(4) $^1$H-NMR (CDCl$_3$) δ: 1.40–1.58 (4 H, m, NCH$_2$CH$_2$CH$_2$), 1.77–1.90 (2 H, m, SCH$_2$CH$_2$), 2.35 (2 H, t, J=7.7 Hz, NCH$_2$), 2.38–2.53 (8 H, m, NCH$_2$CH$_2$x2), 2.88 (6 H, s, CH$_3$x2), 2.89–2.94 (2 H, m, SCH$_2$), 4.22 (1 H, s, CH), 7.20–7.40 (9 H, m, ArH)

Example 40

[Preparation of N,N-Diethyl-6-[4-[(4-chlorophenyl) phenylmethyl]-1-piperazinyl]hexanesulfonamide]

1-[(4-Chlorophenyl)phenylmethyl]piperazine (573.6 mg, 2.00 mmol) and N,N-diethyl-6-chlorohexanesulfonamide (511.6 mg, 2.00 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (50:1), to give N,N-diethyl-6-[4-[(4-chlorophenyl)phenylmethyl]1-piperazinyl]hexanesulfonamide (951.0 mg) as a pale brown oil (yield: 94.0%).

(1) IR vmax (neat) cm$^{-1}$: 1336, 1147 ($SO_2$)

(2) Mass Spectroscopy ($C_{27}H_{40}ClN_3O_2S$) EI: m/z 505 [M]$^+$ (3) EI-HRMS ($C_{27}H_{40}ClN_3O_2S$)
Calculated: 505.2527, Found: 505.2517

(4) $^1$H-NMR (CDCl$_3$) δ: 1.21 (6 H, t, J=7.1 Hz, CH$_2$CH$_3$x2), 1.27–1.54 (6 H, m, NCH$_2$CH$_2$CH$_2$CH$_2$), 1.73–1.86 (2 H, m, SCH$_2$CH$_2$), 2.34 (2 H, t, J=7.8 Hz, NCH$_2$), 2.37–2.52 (8 H, m, NCH$_2$CH$_2$x2), 2.88–2.94 (2 H, m, SCH$_2$), 3.30 (4 H, q, J=7.1 Hz, CH$_2$CH$_3$x2), 4.22 (1 H, s, CH), 7.16–7.40 (9 H, m, ArH)

Example 41

[Preparation of N,N-Diethyl-5-[4-[(4-chlorophenyl) phenylmethyl]-1-piperazinyl]pentanesulfonamide]

1-[(4-Chlorophenyl)phenylmethyl]piperazine (573.6 mg, 2.00 mmol) and N,N-diethyl-5-chloropentanesulfonamide (531.9 mg, 2.20 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (50:1), to give N,N-diethyl-5-[4-[(4-chlorophenyl)phenylmethyl]-1-piperazinyl] pentanesulfonamide (905.2 mg) as a yellow oil (yield based on 1-[(4-chlorophenyl)phenylmethyl]piperazine: 92.0%).

(1) IR vmax (neat) cm$^{-1}$: 1329, 1140 ($SO_2$)

(2) Mass Spectroscopy ($C_{26}H_{38}ClN_3O_2S$) EI: m/z 491 [M]$^+$ (3) EI-HRMS ($C_{26}H_{38}ClN_3O_2S$)
Calculated: 491.2371, Found: 491.2364

(4) $^1$H-NMR (CDCl$_3$) δ: 1.21 (6 H, t, J=7.1 Hz, CH$_2$CH$_3$x2), 1.38–1.57 (4 H, m, NCH$_2$CH$_2$CH$_2$), 1.76–1.88 (2 H, m, SCH$_2$CH$_2$), 2.35 (2 H, t, J=7.7 Hz, NCH$_2$), 2.37–2.52 (8 H, m, NCH$_2$CH$_2$x2), 2.89–2.94 (2 H, m, SCH$_2$), 3.29 (4 H, q, J=7.1 Hz, CH$_2$CH$_3$x2), 4.22 (1 H, S, CH), 7.17–7.40 (9 H, m, ArH)

Example 42

[Preparation of N-n-Butyl-N-methyl-6-[4-[(4-chlorophenyl)phenylmethyl]-1-piperazinyl] hexanesulfonamide]

1-[(4-Chlorophenyl)phenylmethyl]piperazine (573.6 mg, 2.00 mmol) and N-n-butyl-N-methyl-6-chlorohexanesulfonamide (539.7 mg, 2.00 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (50:1), to give N-n-butyl-N-methyl-6-[4-[(4-chlorophenyl)phenylmethyl]-1-piperazinyl]hexanesulfonamide (951.0 mg) as a pale brown oil (yield: 91.4%).

(1) IR vmax (neat) cm$^{-1}$: 1334, 1143 ($SO_2$)

(2) Mass Spectroscopy ($C_{28}H_{42}ClN_3O_2S$) EI: m/z 519 [M]$^+$ (3) EI-HRMS ($C_{28}H_{42}ClN_3O_2S$)
Calculated: 519.2684, Found: 519.2682

(4) $^1$H-NMR (CDCl$_3$) δ: 0.96 (3 H, t, J=7.3 Hz, CH$_2$CH$_3$), 1.27–1.63 (10 H, m, NCH$_2$(CH$_2$)$_3$CH$_2$CH$_2$S, NCH$_2$(CH$_2$)$_2$CH$_3$), 1.74–1.86 (2 H, m, SCH$_2$CH$_2$), 2.34 (2 H, t, J=7.9 Hz, NCH$_2$), 2.37–2.52 (8 H, m, NCH$_2$CH$_2$x2), 2.86 (3 H, s, NCH$_3$), 2.88–2.94 (2 H, m, SCH$_2$), 3.16 (2 H, t, J=7.4 Hz, NCH$_2$(CH$_2$)$_2$CH$_3$), 4.22 (1 H, s, CH), 7.17–7.40 (9 H, m, ArH)

Example 43

[Preparation of N-n-Butyl-N-methyl-5-[4-[(4-chlorophenyl)phenylmethyl]-1-piperazinyl] pentanesulfonamide]

1-[(4-Chlorophenyl)phenylmethyl-3-piperazine (624.0 mg, 2.17 mmol) and N-n-butyl-N-methyl-5-chloropentanesulfonamide (612.0 mg, 2.39 mmol) were refluxed in N-ethyldiisopropylamine (2 ml) for 6 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform, to give N-n-butyl-N-methyl-5-[4-[(4-chlorophenyl)phenylmethyl]-1-piperazinyl]

pentanesulfonamide (1029.0 mg) as a yellow oil (yield based on 1-[(4-chlorophenyl)phenylmethyl]piperazine: 93.6%).

(1) IR vmax (neat) cm$^{-1}$: 1333, 1144 (SO$_2$)
(2) Mass Spectroscopy (C$_{27}$H$_{40}$ClN$_3$O$_2$S) EI: m/z 505 [M]$^+$
(3) EI-HRMS (C$_{27}$H$_{40}$ClN$_3$O$_2$S)
Calculated: 505.2527, Found: 505.2522
(4) $^1$H-NMR (CDCl$_3$) δ: 0.96 (3 H, t, J=7.3 Hz, CH$_2$CH$_3$), 1.30–1.64 (8 H, m, NCH$_2$(CH$_2$)$_2$CH$_2$CH$_2$S, NCH$_2$ (CH$_2$)$_2$CH$_3$), 1.77–1.88 (2 H, m, SCH$_2$CH$_2$), 2.35 (2 H, t, J=7.7 Hz, NCH$_2$), 2.38–2.53 (8 H, m, NCH$_2$CH$_2$x2), 2.86 (3 H, s, NCH$_3$), 2.88–2.94 (2 H, m, SCH$_2$), 3.16 (2 H, t, J=7.4 Hz, NCH$_2$(CH$_2$)$_2$CH$_3$), 4.22 (1 H, s, CH), 7.17–7.40 (9 H, m, ArH)

Example 44

[Preparation of (+)-N-Cyclopropyl-6-[4-[(3-chlorophenyl)phenylmethyl]-1-piperazinyl] hexanesulfonamide]

(+)-1-[(3-Chlorophenyl)phenylmethyl]piperazine (2.27 g, 7.90 mmol) prepared in the same manner as in Preparation Example 18 and N-cyclopropyl-6-chlorohexanesulfonamide (2.08 g, 8.69 mmol) were refluxed in N-ethyldiisopropylamine (10 ml) for 4 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1)], to give (+)-N-cyclopropyl-6-[4-[(3-chlorophenyl)phenylmethyl]-1-piperazinyl]hexanesulfonamide (3.35 g) as a pale yellow oil (yield based on (+)-1-[(3-chlorophenyl)phenylmethyl] piperazine: 86.4%).

(1) Mass Spectroscopy (C$_{26}$H$_{36}$ClN$_3$O$_2$S) EI: m/z 489 [M]$^+$
(2) EI-HRMS (C$_{26}$H$_{36}$ClN$_3$O$_2$S)
Calculated: 489.2214, Found: 489.2208
(3) [α]$_D^{26}$+11.1° (c =4.50, methanol)

In order to determine the optical purity of the resulting (+)-N-cyclopropyl-6-[4-[(3-chlorophenyl)phenylmethyl]-1-piperazinyl]hexanesulfonamide, HPLC analysis was carried out. Its analytical conditions are as follows.

[HPLC Analytical Conditions]
Column: ULTRON ES-OVM, 4.6 mm×150 mm (5 μm)
Mobile Phase: ethanol:phosphate buffer (pH 6.0) =3:7
Flow Rate: 0.9 ml/min.
Detection: at UV 254 nm
Retention Time [N-cyclopropyl-6-[4-[(3-chlorophenyl) phenylmethyl]-1-piperazinyl]hexanesulfonamide (racemate)]:
9.2 min. [50%, (+)-form]
13.1 min. [50%, (−)-form]
Subject: 9.5 min. (98.8%), 14.1 min. (1.2%)

From the above results, it was found that the optical purity of the (+)-N-cyclopropyl-6-[4-[(3-chlorophenyl) phenylmethyl]-1-piperazinyl]hexanesulfonamide obtained in Example 44 was 97.6% ee.

Example 45

[Preparation of (+)-N-Cyclopropyl-6-[4-[(3-chlorophenyl)phenylmethyl]-1-piperazinyl] hexanesulfonamide dihydrochloride]

(+)-N-Cyclopropyl-6-[4-[(3-chlorophenyl) phenylmethyl]-1-piperazinyl]hexanesulfonamide (3.26 g, 6.65 mmol) prepared in the same manner as in Example 15 was formed into a hydrochloride salt in a 15% HCl-methanol solution. The resulting hydrochloride salt was recrystallized from ethanol, to give (+)-N-cyclopropyl-6-[4-[(3-chlorophenyl)phenylmethyl]-1-piperazinyl] hexanesulfonamide dihydrochloride (3.10 g) as colorless prisms (yield: 82.8%).

(1) Melting Point: 162°–164° C.
(2) Elemental Analysis (as C$_{26}$H$_{36}$ClN$_3$O$_2$S 2HCl)
Calculated: C, 55.46; H, 6.80; N, 7.46
Found: C, 55.42; H, 6.52; N, 7.44
(3) [α]$_D^{26}$+5.1° (c =1.0, methanol)

Example 46

[Preparation of (−)-N-Cyclopropyl-6-[4-[(3-chlorophenyl)phenylmethyl]-1-piperazinyl] hexanesulfonamide]

(−)-1-[(3-Chlorophenyl)phenylmethyl]piperazine (2.60 g, 9.06 mmol) prepared in the same manner as in Preparation Example 21 and N-cyclopropyl-6-chlorohexanesulfonamide (2.40 g, 10.00 mmol) were refluxed in N-ethyldiisopropylamine (13 ml) for 4 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give (−)-N-cyclopropyl-6-[4-[(3-chlorophenyl)phenylmethyl]-1-piperazinyl]hexanesulfonamide (3.78 g) as a pale yellow oil (yield based on (−)-1-[(3-chlorophenyl)phenylmethyl] piperazine: 86.0%).

(1) Mass Spectroscopy (C$_{26}$H$_{36}$ClN$_3$O$_2$S) EI: m/z 489 [M]$^+$
(2) EI-HRMS (C$_{26}$H$_{36}$ClN$_3$O$_2$S)
Calculated: 489.2214, Found: 489.2215
(3) [α]$_D^{26}$−10.6° (c =5.60, methanol)

In order to determine the optical purity of the resulting (−)-N-cyclopropyl-6-[4-[(3-chlorophenyl)phenylmethyl]-1-piperazinyl]hexanesulfonamide, HPLC analysis was carried out in accordance with the process in Example 44. As a result, it was found that the optical purity of the (−)-N-cyclopropyl-6-[4-[(3-chlorophenyl)phenylmethyl]-1-piperazinyl]hexanesulfonamide was 97.6% ee.

Example 47

[Preparation of (−)-N-Cyclopropyl-6-[4-[(3-chlorophenyl)phenylmethyl]-1-piperazinyl] hexanesulfonamide dihydrochloride]

(−)-N-Cyclopropyl-6-[4-[(3-chlorophenyl) phenylmethyl]-1-piperazinyl]hexanesulfonamide (3.69 g, 7.53 mmol) prepared in the same manner as in Example 15 was formed into a hydrochloride salt in a 15% HCl-methanol solution. The resulting hydrochloride salt was recrystallized from ethanol, to give (−)-N-cyclopropyl-6-[4-[(3-chlorophenyl)phenylmethyl]-1-piperazinyl] hexanesulfonamide dihydrochloride (3.26 g) as colorless prisms (yield: 76.9%).

(1) Melting Point: 162°–165° C.
(2) Elemental Analysis (as $C_{26}H_{36}ClN_3O_2S2HCl$)
Calculated: C, 55.46; H, 6.80; N, 7.46
Found: C, 55.25; H, 6.65; N, 7.45
(3) $[\alpha]_D^{26}$ –5.1° (c =1.0, methanol)

Example 48

[Preparation of (+)-N-Cyclopropyl-6-[4-[(4-chlorophenyl)phenylmethyl]-1-piperazinyl]hexanesulfonamide]

(+)-1-[(4-Chlorophenyl)phenylmethyl]piperazine (1.35 g, 4.71 mmol) [optical purity 99.0%, $[\alpha]_D^{27}$+14.9° (c =1.00, methanol)] obtained in accordance with the process described in *J. Chem. Soc.*, 1958–1960 (1939) or Japanese Patent Laid-Open No. 2816/1995 and N-cyclopropyl-6-chlorohexanesulfonamide (1.24 g, 5.18 mmol) were refluxed in N-ethyldiisopropylamine (10 ml) for 4 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give (+)-N-cyclopropyl-6-[4-[(4-chlorophenyl)phenylmethyl]-1-piperazinyl]hexanesulfonamide (2.10 g) as a pale yellow oil (yield based on (+)-1-[(4-chlorophenyl)phenylmethyl]piperazine: 91.3%).

(1) Mass Spectroscopy ($C_{26}H_{36}ClN_3O_2S$) EI: m/z 489 [M]+
(2) EI-HRMS ($C_{26}H_{36}ClN_3O_2S$)
Calculated: 489.2214, Found: 489.2216
(3) $[\alpha]_D^{27}$+5.3° (c =5.40, methanol) In order to determine the optical purity of the resulting (+)-N-cyclopropyl-6-[4-[(4-chlorophenyl)phenylmethyl]-1-piperazinyl]hexanesulfonamide, HPLC analysis was carried out. Its analytical conditions are as follows.

[HPLC Analytical Conditions]
Column: ULTRON ES-OVM, 4.6 mm×150 mm (5 μm)
Mobile Phase: acetonitrile:acetate buffer (pH 5.1)=13:87
Flow Rate: 1.5 ml/min.
Detection: at UV 254 nm
Retention Time [N-cyclopropyl-6-[4-[(4-chlorophenyl)phenylmethyl]-1-piperazinyl]hexanesulfonamide (racemate)]:
9.4 min. [50%, (+)-form]
15.7 min. [50%, (−)-form]
Subject: 9.5 min. (99.5%), 15.7 min. (0.5%)

From the above results, it was found that the optical purity of the (+)-N-cyclopropyl-6-[4-[(4-chlorophenyl)phenylmethyl]-1-piperazinyl]hexanesulfonamide obtained in Example 48 was 99.0% ee.

Example 49

[Preparation of (−)-N-Cyclopropyl-6-[4-[(4-chlorophenyl)phenylmethyl]-1-piperazinyl]hexanesulfonamide]

(−)-1-[(4-Chlorophenyl)phenylmethyl]piperazine (1.20 g, 4.18 mmol) [optical purity 98.4%, $[\alpha]_D^{27}$–14.2° (c =1.153, methanol)] obtained in accordance with the process described in *J. Chem. Soc.*, 1958–1960 (1939) or Japanese Patent Laid-Open No. 2816/1995 and N-cyclopropyl-6-chlorohexanesulfonamide (1.10 g, 4.59 mmol) were refluxed in N-ethyldiisopropylamine (10 ml) for 4 hours. The reaction mixture was concentrated in vacuo, and water was added thereto. The mixture was extracted with chloroform. The chloroform layer was washed with water, and dried over anhydrous magnesium sulfate. Subsequently, the solvent was removed by evaporation in vacuo. The resulting crude product was purified by column chromatography on silica gel with chloroform-methanol (20:1), to give (−)-N-cyclopropyl-6-[4-[(4-chlorophenyl)phenylmethyl]-1-piperazinyl]hexanesulfonamide (1.64 g) as a pale yellow oil (yield based on (−)-1-[(4-chlorophenyl)phenylmethyl]piperazine: 80.0%).

(1) Mass Spectroscopy ($C_{26}H_{36}ClN_3O_2S$) EI: m/z 489 [M]+
(2) EI-HRMS ($C_{26}H_{36}ClN_3O_2S$)
Calculated: 489.2214, Found: 489.2216
(3) $[\alpha]_D^{27}$–5.1° (c =4.50, methanol)

In order to determine the optical purity of the resulting (−)-N-cyclopropyl-6-[4-[(4-chlorophenyl)phenylmethyl]-1-piperazinyl]hexanesulfonamide, HPLC analysis was carried out in accordance with the process in Example 48. As a result, it was found that the optical purity of the (−)-N-cyclopropyl-6-[4-[(4-chlorophenyl)phenylmethyl]-1-piperazinyl]hexanesulfonamide was 98.2% ee.

Comparative Example 1

[Preparation of N-Cyclopropyl-6-[4-[(3-chlorophenyl)phenylmethyl]-1-piperazinyl]hexanesulfonamide]

1-[(3-Chlorophenyl)phenylmethyl]piperazine (543.7 mg, 1.90 mmol) and N-cyclopropyl-6-chlorohexanesulfonamide (500 mg, 2.09 mmol) were refluxed in toluene (15 ml) for 4 hours in the presence of triethylamine (211 mg, 2.09 mmol). The reaction mixture was washed with water, and the organic layer was dried over anhydrous magnesium sulfate. Subsequently, the solvent was removed by evaporation in vacuo. The resulting crude product was purified by column chromatography on silica gel with chloroform-methanol (20:1), to give N-cyclopropyl-6-[4-[(3-chlorophenyl)phenylmethyl]-1-piperazinyl]hexanesulfonamide (84.1 mg) as an oil (yield based on 1-[(3-chlorophenyl)phenylmethyl]piperazine: 9.0%).

The resulting N-cyclopropyl-6-[4-[(3-chlorophenyl)phenylmethyl]-1-piperazinyl]hexanesulfonamide had physical properties similar to those of N-cyclopropyl-6-[4-[(3-chlorophenyl)phenylmethyl]-1-piperazinyl]hexanesulfonamide obtained in Example 1.

Comparative Example 2

[Preparation of N-Cyclopropyl-6-[4-[(3-chlorophenyl)phenylmethyl]-1-piperazinyl]hexanesulfonamide]

1-[(3-Chlorophenyl)phenylmethyl]piperazine (543.7 mg, 1.90 mmol) and N-cyclopropyl-6-chlorohexanesulfonamide (500 mg, 2.09 mmol) were refluxed in toluene (15 ml) in the presence of triethylamine (211 mg, 2.09 mmol) for 48 hours. The reaction mixture was washed with water, and the organic layer was dried over anhydrous magnesium sulfate. Subsequently, the solvent was removed by evaporation in vacuo. The resulting crude product was purified by column chromatography on silica gel with chloroform-methanol (20:1), to give N-cyclopropyl-6-[4-[(3-chlorophenyl)phenylmethyl]-1-piperazinyl]hexanesulfonamide (482.7 mg) as an oil (yield based on 1-[(3-chlorophenyl)phenylmethyl]piperazine: 52.0%).

The resulting N-cyclopropyl-6-[4-[(3-chlorophenyl)phenylmethyl]-1-piperazinyl]hexanesulfonamide had physical properties similar to those of N-cyclopropyl-6-[4-[(3-chlorophenyl)phenylmethyl]-1-piperazinyl]hexanesulfonamide obtained in Example 1.

Comparative Example 3

[Preparation of N-Cyclopropyl-6-[4-[(3-chlorophenyl)phenylmethyl]-1-piperazinyl]hexanesulfonamide]

1-[(3-Chlorophenyl)phenylmethyl]piperazine (435.2 mg, 1.52 mmol) and N-cyclopropyl-6-bromohexanesulfonamide (474.5 mg, 1.67 mmol) were refluxed in toluene (15 ml) in the presence of triethylamine (169 mg, 1.67 mmol) for 42 hours. The reaction mixture was washed with water, and the organic layer was dried over anhydrous magnesium sulfate. Subsequently, the solvent was removed by evaporation in vacuo. The resulting crude product was purified by column chromatography on silica gel with chloroform-methanol (20:1), to give N-cyclopropyl-6-[4-[(3-chlorophenyl)phenylmethyl]-1-piperazinyl]hexanesulfonamide (499.0 mg) as an oil (yield based on 1-[(3-chlorophenyl)phenylmethyl]piperazine: 67.1%).

The resulting N-cyclopropyl-6-[4-[(3-chlorophenyl)phenylmethyl]-1-piperazinyl]hexanesulfonamide had physical properties similar to those of N-cyclopropyl-6-[4-[(3-chlorophenyl)phenylmethyl]-1-piperazinyl]hexanesulfonamide obtained in Example 1.

It is clear from the above results that the piperizinesulfonamide derivatives and salts thereof can be industrially advantageously prepared in a short period of time and at high yield according to the processes of Examples.

EQUIVALENTS

Those skilled in the art will recognize, or be able to ascertain using simple routine experimentation, many equivalents to the specific embodiments of the invention described in the present specification. Such equivalents are intended to be encompassed in the scope of the present invention as described in the following claims.

What is claimed is:

1. A process for preparing a piperazinesulfonamide compound represented by the formula (III):

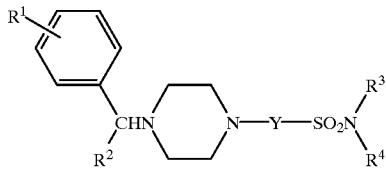

(III)

wherein $R^1$ is hydrogen atom, a straight or branched chain alkyl group having 1 to 6 carbon atoms, an alkoxy group having 1 to 4 carbon atoms, a halogen atom, hydroxyl group, trifluoromethyl group, nitro group or amino group; $R^2$ is a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group, amino group, 2-pyridyl group, 3-pyridyl group and 4-pyridyl group; each of $R^3$ and $R^4$ is independently hydrogen atom, a straight or branched chain allyl group having 1 to 6 carbon atoms, a hydroxyalkyl group having 1 to 4 carbon atoms, a cycloalkyl group having 3 to 8 carbon atoms, or a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group; and Y is an alkylene group having 1 to 12 carbon atoms, comprising:
reacting a piperazine compound represented by the formula (I):

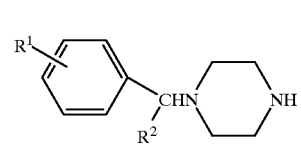

(I)

wherein $R^1$ and $R^2$ are as defined above, with a halogenoalkylsulfonamide compound represented by the formula (II):

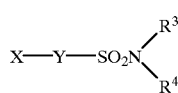

(II)

wherein $R^3$, $R^4$ and Y are as defined above; and X is chlorine atom, bromine atom or iodine atom, in the presence of an organic base selected from the group consisting of N-ethyldiiso-propylamine, N-ethylmorpholine, triethylamine and 2,4,6-trimethylpyridine, and in the absence of a solvent.

2. The process as claimed in claim 1, wherein the piperazinesulfonamide compound represented by the formula (III) having optical activity is prepared by using piperazine compound represented by the formula (I) having optical activity.

3. The process as claimed in claim 1, wherein $R^1$ is hydrogen atom, a straight or branched chain alkyl group having 1 to 4 carbon atoms, an alkoxy group having 1 to 4 carbon atoms, a halogen atom, hydroxyl group, trifluoromethyl group, nitro group or amino group.

4. The process as claimed in claim 1, wherein $R^1$ is hydrogen atom or a halogen atom.

5. The process as claimed in claim 1, wherein $R^1$ is a halogen atom at meta-position or para-position.

6. The process as claimed in claim 1, wherein $R^2$ is a phenyl group which may have as substituents one or two halogen atoms on its phenyl ring, 2-pyridyl group or 4-pyridyl group.

7. The process as claimed in claim 1, wherein $R^2$ is a phenyl group which may have as a substituent one halogen atom on its phenyl ring, 2-pyridyl group or 4-pyridyl group.

8. The process as claimed in claim 1, wherein $R^2$ is unsubstituted phenyl group.

9. The process as claimed in claim 1, wherein each of $R^3$ and $R^4$ is independently hydrogen atom, a straight or branched chain alkyl group having 1 to 6 carbon atoms, a hydroxyalkyl group having 1 to 4 carbon atoms or a cycloalkyl group having 3 to 8 carbon atoms.

10. The process as claimed in claim 1, wherein each of $R^3$ and $R^4$ is independently hydrogen atom, a straight or branched chain alkyl group having 1 to 6 carbon atoms, a hydroxyalkyl group having 1 to 4 carbon atoms or a cycloalkyl group having 3 to 6 carbon atoms.

11. The process as claimed in claim 1, wherein each of $R^3$ and $R^4$ is independently a straight or branched chain alkyl group having 1 to 6 carbon atoms.

12. The process as claimed in claim 1, wherein $R^4$ is hydrogen atom.

13. The process as claimed in claim 1, wherein $R^3$ is a hydroxyalkyl group having 1 to 4 carbon atoms, and $R^4$ is hydrogen atom.

14. The process as claimed in claim 1, wherein $R^3$ is a cycloalkyl group having 3 to 6 carbon atoms, and $R^4$ is hydrogen atom.

15. The process as claimed in claim 1, wherein the organic base is N-ethyldiisopropylamine or triethylamine.

16. A process for preparing a pharmaceutically acceptable salt of a piperazinesulfonamide compound represented by the formula (III):

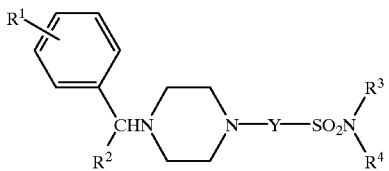

wherein $R^1$ is hydrogen atom, a straight or branched chain alkyl group having 1 to 6 carbon atoms, an alkoxy group having 1 to 4 carbon atoms, a halogen atom, hydroxyl group, trifluoromethyl group, nitro group or amino group; $R^2$ is a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group amino group, 2-pyridyl group, 3-pyridyl group and 4-pyridyl group; each of $R^3$ and $R^4$ is independently hydrogen atom, a straight or branched chain alkyl group having 1 to 6 carbon atoms, a hydroxyalkyl group having 1 to 4 carbon atoms, a cycloalkyl group having 3 to 8 carbon atoms, or a phenyl group which may have as substituents on its phenyl ring 1 to 3 groups selected from the group consisting of an alkyl group having 1 to 4 carbon atoms, an alkoxy group having 1 to 4 carbon atoms, a halogen atom, hydroxyl group, trifluoromethyl group, nitro group and amino group; and Y is an alkylene group having 1 to 12 carbon atoms, comprising the step of preparing the piperazinesulfonamide compound represented by the formula (III) by the process according to claim 1.

17. The process as claimed in claim 16, wherein the pharmaceutically acceptable salt of the piperazine compound represented by the formula (III) having optical activity is prepared by using a piperazine compound represented by the formula (I) having optical activity.

\* \* \* \* \*

UNITED STATES PATENT AND TRADEMARK OFFICE
CERTIFICATE OF CORRECTION

PATENT NO.    : 6,172,228 B1
DATED         : January 9, 2001
INVENTOR(S)   : Kenichi Kashima et al.

It is certified that error appears in the above-identified patent and that said Letters Patent is hereby corrected as shown below:

Column 2,
Line 7, change "4" to -- 4 --.

Column 4,
Line 62, delete "Be".

Column 6,
Lines 16 and 47, delete "1".

Column 7,
Line 37, change "R" to -- $R^3$ --.

Column 8,
Line 67, change "N-(2-hydroxyethyl)11brmoundecanesulfonamide"
to -- N-(2-hydroxyethyl)-11-bromoundecanesulfonamide --.

Column 9,
Line 5, change "N,N-(4-hydroxybutyl)-6-chlorohexanesulfonamide" to
-- N-(4-hydroxybutyl)-6-chlorohexanesulfonamide --.

Column 10,
Line 26 (formula (IV)), change "$So_2$" to -- $SO_2$ --.

Column 17,
Lines 60 and 61, change "Cg" to -- $C_9$ --.

Column 18,
Line 2, change "N-(2-Hydroxvethyl)6-" to -- N-(2-Hydroxyethyl)6- --.
Line 37, change "chloroPentanesulfonamide" to -- chloropentanesulfonamide --.

Column 19,
Line 14, change "3.0" to -- 3.04 --.
Line 32, change "($C_9H_20CINO_3S$)" to -- ($C_9H_{20}CINO_3S$) --.
Line 38, change "$CICH_2CH_2$, $SCH_2CH_2$," to -- $CICH_2C\underline{H}_2$, $SCH_2C\underline{H}_2$, --.

Column 20,
Line 25, change "CaHI" to -- $C_8H_{18}$ --.
Line 30, change "$SCH_2CH_2$," to -- $SCH_2C\underline{H}_2$, --.

UNITED STATES PATENT AND TRADEMARK OFFICE
CERTIFICATE OF CORRECTION

PATENT NO.     : 6,172,228 B1
DATED          : January 9, 2001
INVENTOR(S)    : Kenichi Kashima et al.

It is certified that error appears in the above-identified patent and that said Letters Patent is hereby corrected as shown below:

Column 21,
Line 11, change "C10" to -- $C_{10}$ --.
Line 13, change "C10" to -- $C_{10}$ -- and change "O₂s" to -- $O_2S$ --.

Column 22,
Line 6, change "cm⁻" to -- $cm^{-1}$ --.
Line 9, change "C10" to -- $C_{10}$ --.
Line 41, change "Preparation of +(+)-(3-Chlorophenyl)" to -- Preparation of (+)-(3-Chlorophenyl) --.

Column 25,
Line 5, change "25.6º" to -- -25.6º --.
Line 28, change "18.3º" to -- -18.3º --.
Line 59, change "C10" to -- $C_{10}$ --.

Column 26,
Line 60, change "Preparation of N-Cyclopropyl-1-" to -- Preparation of N-Cyclopropyl-11- --.

Column 27,
Line 26, change "C15" to -- $C_{15}$ --.
Last line, change "CHCH₂CH₂" to -- CHC$\underline{H}$C$\underline{H}_2$ -- and change "NHCH₂CH₂CH₂CH₂" to -- NHCH₂C$\underline{H}_2$C$\underline{H}_2$C$\underline{H}_2$ --.

Column 28,
Line 1, change "SCHCH₂" to -- SCH₂C$\underline{H}_2$ --.
Line 3, change "CHCH₂CH₂)" to -- C$\underline{H}$CH₂CH₂) --.

Column 29,
Line 18, change "CHCH₂CH₂" to -- CHC$\underline{H}_2$CH₂ -- and change "NHCH₂CH₂CH₂CH₂" to -- NHCH₂C$\underline{H}_2$C$\underline{H}_2$C$\underline{H}_2$ --
Line 19, change "SCHCH₂" to -- SCH₂C$\underline{H}_2$ --.
Line 21, change "CHCH₂CH₂)" to -- C$\underline{H}$CH₂CH₂) --.
Line 52, change "CHCH₂CH₂" to -- CHC$\underline{H}_2$CH₂ -- and change "NHCH₂CH₂CH₂CH₂" to -- NHCH₂C$\underline{H}_2$C$\underline{H}_2$C$\underline{H}_2$ --.
Line 53, change "SCHCH₂" to -- SCH₂C$\underline{H}_2$ --
Line 55, change "CHCH₂CH₂)" to -- C$\underline{H}$CH₂CH₂) --

UNITED STATES PATENT AND TRADEMARK OFFICE
CERTIFICATE OF CORRECTION

PATENT NO.    : 6,172,228 B1
DATED         : January 9, 2001
INVENTOR(S)   : Kenichi Kashima et al.

It is certified that error appears in the above-identified patent and that said Letters Patent is hereby corrected as shown below:

Column 30,
Line 18, change "CHCH$_2$CH$_2$" to -- CHC<u>H</u>$_2$C<u>H</u>$_2$ --; and change "NHCH$_2$CH$_2$CH$_2$CH$_2$" to -- NHCH$_2$C<u>H</u>$_2$C<u>H</u>$_2$C<u>H</u>$_2$ --.
Line 19, change "SCH$_2$CH$_2$)" to -- SCH$_2$C<u>H</u>$_2$) --.
Line 21, change "CHCH$_2$CH$_2$)" to -- C<u>H</u>CH$_2$CH$_2$) --.
Line 52, change "CH$_2$" to --C<u>H</u>$_2$ -- in each instance.
Line 53, change "SCH$_2$CH$_2$)" to -- SCH$_2$C<u>H</u>$_2$) --.
Line 55, change "CHCH$_2$CH$_2$)" to -- C<u>H</u>CH$_2$CH$_2$) --.

Column 31,
Line 19, change "CHCH$_2$CH$_2$" to -- CHC<u>H</u>$_2$C<u>H</u>$_2$ -- and change "NHCH$_2$CH$_2$CH$_2$CH$_2$" to -- NHCH$_2$C<u>H</u>$_2$C<u>H</u>$_2$C<u>H</u>$_2$ --.
Line 20, change "SCH$_2$CH$_2$)" to -- SCH$_2$CH$_2$) --.
Line 22, change "CHCH$_2$CH$_2$)" to -- C<u>H</u>CH$_2$CH$_2$) --.
Line 32, change "N-cyclopentyl]-6-" to -- N-cyclopentyl-6- --.
Line 52, change "CHCH$_2$CH$_2$" to -- CHC<u>H</u>$_2$C<u>H</u>$_2$ --; and change "NHCH$_2$CH$_2$CH$_2$CH$_2$" to -- NHCH$_2$C<u>H</u>$_2$C<u>H</u>$_2$C<u>H</u>2 --.
Line 53, change "SCH$_2$CH$_2$)" to -- SCH$_2$C<u>H</u>$_2$ ) --.
Line 55, change "CHCH$_2$CH$_2$)" to -- C<u>H</u>CH$_2$CH$_2$) --.

Column 32,
Line 8, change "chlorophenyl)phenylmethyl]1-piperazinyl]" to -- chlorophenyl)phenylmethyl]-1-piperazinyl] --.
Line 16, change "CH$_2$CH$_2$CH$_2$)" to -- C<u>H</u>$_2$C<u>H</u>$_2$C<u>H</u>$_2$) --.
Line 16, change "SCH$_2$CH$_2$)" to -- SCH$_2$C<u>H</u>$_2$) --.
Line 53, change "phenylmethyl]-1-piperazinyl)hexanesulfonamide:" to -- phenylmethyl]-1-piperazinyl]hexanesulfonamide: --.

Column 35,
Line 13, change "cm-:" to -- cm$^{-1}$: --.
Line 21, change "NHCH$_2$CH$_2$CH$_2$CH$_2$" to -- NHCH$_2$C<u>H</u>$_2$C<u>H</u>$_2$C<u>H</u>$_2$ --.
Line 24, change "NCH$_2$CH$_2$OH" to -- NC<u>H</u>$_2$CH$_2$OH --.
Line 25, change "NCH$_2$CH$_2$OH" to -- NCH$_2$C<u>H</u>$_2$OH --.
Line 30, change "chlorophenyl phenylmethyl]-1-piperazinyl" to -- chlorophenyl)phenylmethyl]-1-piperazinyl --.

UNITED STATES PATENT AND TRADEMARK OFFICE
CERTIFICATE OF CORRECTION

PATENT NO. : 6,172,228 B1
DATED : January 9, 2001
INVENTOR(S) : Kenichi Kashima et al.

It is certified that error appears in the above-identified patent and that said Letters Patent is hereby corrected as shown below:

Column 36,
Line 8, change "NCH$_2$CH$_2$CH$_2$" to -- NCH$_2$C$\underline{H}_2$C$\underline{H}_2$ --.
Line 8, change "SCH$_2$CH$_2$)" to -- SCH$_2$C$\underline{H}_2$) --.
Line 11, change "NCH$_2$CH$_2$OH" to -- NC$\underline{H}_2$CH$_2$OH --.
Line 12, change "NCH$_2$CH$_2$OH" to -- NCH$_2$C$\underline{H}_2$OH --.
Lines 44-45, change "NCH$_2$(CH$_2$)$_9$CH$_2$CH$_2$S" to -- NCH$_2$(C$\underline{H}_2$)$_9$CH$_2$CH$_2$S --.
Line 45, change "SCH$_2$CH$_2$OH)" to -- SCH$_2$C$\underline{H}_2$ --.
Line 48, change "NCH$_2$CH$_2$OH)" to -- NC$\underline{H}_2$CH$_2$OH) --.
Line 49, change "NCH$_2$CH$_2$OH)" to -- NCH$_2$C$\underline{H}_2$OH) --.

Column 37,
Line 13, change "NCH$_2$CH$_2$CH$_2$CH$_2$" to -- NCH$_2$C$\underline{H}_2$C$\underline{H}_2$C$\underline{H}_2$ --
Line 13, change "SCH$_2$CH$_2$" to -- SCH$_2$C$\underline{H}_2$ --.
Line 14, change "NCH$_2$CH$_2$CH$_2$OH)" to -- NCH$_2$C$\underline{H}_2$CH$_2$OH) -- .
Line 17, change "NCH$_2$CH$_2$CH$_2$OH)" to -- NC$\underline{H}_2$CH$_2$CH$_2$OH) -- .
Line 18, change "NCH$_2$CH$_2$CH$_2$H)" to -- NCH$_2$CH$_2$C$\underline{H}_2$OH) -- .
Line 48, change "NCH$_2$CH$_2$CH$_2$)" to -- NCH$_2$C$\underline{H}_2$C$\underline{H}_2$) -- .
Line 48, change "SCH$_2$CH$_2$" to -- SCH$_2$C$\underline{H}_2$ --.
Line 49, change "NCH$_2$CH$_2$CH$_2$OH)" to -- NCH$_2$C$\underline{H}_2$CH$_2$OH) -- .
Line 52, change "NCH$_2$CH$_2$CH$_2$OH)" to -- NC$\underline{H}_2$CH$_2$CH$_2$OH) -- .
Line 53, change "NCH$_2$CH$_2$CH$_2$OH)" to -- NCH$_2$CH$_2$C$\underline{H}_2$OH) -- .

Column 38,
Line 17, change "NCH$_2$CH$_2$CH$_2$CH$_2$)" to -- NCH$_2$C$\underline{H}_2$C$\underline{H}_2$C$\underline{H}_2$) -- .
Line 18, change "NCH$_2$CH$_2$CH$_2$CH$_2$OH)" to -- NCH$_2$C$\underline{H}_2$C$\underline{H}_2$CH$_2$OH) -- .
Line 19, change "SCH$_2$CH$_2$" to -- SCH$_2$C$\underline{H}_2$ --.
Line 22, change "NCH$_2$CH$_2$CH$_2$CH$_2$OH)" to -- NC$\underline{H}_2$CH$_2$CH$_2$CH$_2$OH) -- .
Line 23, change "NCH$_2$CH$_2$CH$_2$CH$_2$OH)" to -- NCH$_2$CH$_2$CH$_2$C$\underline{H}_2$OH) -- .
Line 53, change "NCH$_2$CH$_2$CH$_2$)" to -- NCH$_2$C$\underline{H}_2$C$\underline{H}_2$) -- .
Line 54, change "NCH$_2$CH$_2$CH$_2$CH$_2$OH)" to -- NCH$_2$C$\underline{H}_2$C$\underline{H}_2$CH$_2$OH) -- .
Line 55, change "SCH$_2$CH$_2$" to -- SCH$_2$C$\underline{H}_2$ --.
Line 57, change "NCH$_2$CH$_2$CH$_2$CH$_2$OH)" to -- NC$\underline{H}_2$CH$_2$CH$_2$CH$_2$OH) -- .
Line 58, change "NCH$_2$CH$_2$CH$_2$CH$_2$OH)" to -- NCH$_2$CH$_2$CH$_2$C$\underline{H}_2$OH) -- .

UNITED STATES PATENT AND TRADEMARK OFFICE
CERTIFICATE OF CORRECTION

PATENT NO.    : 6,172,228 B1
DATED         : January 9, 2001
INVENTOR(S)   : Kenichi Kashima et al.

It is certified that error appears in the above-identified patent and that said Letters Patent is hereby corrected as shown below:

Column 39,
Line 21, change "NCH$_2$CH$_2$CH$_2$CH$_2$)" to -- NCH$_2$C$\underline{H}_2$C$\underline{H}_2$CH$_2$) --.
Line 21, change "SCH$_2$CH$_2$" to -- SCH$_2$C$\underline{H}_2$ --.
Line 24, change "NCH$_2$CH$_2$OH)" to -- NC$\underline{H}_2$CH$_2$OH) --.
Line 25, change "NCH$_2$CH$_2$OH)" to -- NCH$_2$C$\underline{H}_2$OH) -- .
Line 50, change " '3) " to -- (3) --; and change "N$_2$" to -- N$_3$ --.
Line 53, change "NCH$_2$CH$_2$CH$_2$)" to -- NCH$_2$C$\underline{H}_2$C$\underline{H}_2$) -- .
Line 53, change "SCH$_2$CH$_2$" to -- SCH$_2$C$\underline{H}_2$ --.
Line 56, change "NCH$_2$CH$_2$OH)" to -- NC$\underline{H}_2$CH$_2$OH) --.
Line 57, change "NCH$_2$CH$_2$OH)" to -- NCH$_2$C$\underline{H}_2$OH) --.

Column 40,
Line 19, change "NCH$_2$CH$_2$CH$_2$CH$_2$)" to -- NCH$_2$C$\underline{H}_2$C$\underline{H}_2$CH$_2$) --.
Line 19, change "SCH$_2$CH$_2$" to -- SCH$_2$C$\underline{H}_2$ --.
Line 20, change "NCH$_2$CH$_2$CH$_2$OH)" to -- NCH$_2$C$\underline{H}_2$CH$_2$OH) --.
Line 23, change "NCH$_2$CH$_2$CH$_2$OH)" to -- NC$\underline{H}_2$CH$_2$CH$_2$OH) --.
Line 24, change "NCH$_2$CH$_2$CH$_2$OH)" to -- NCH$_2$CH$_2$C$\underline{H}_2$OH) --.
Line 31, change "pentanesulfonamide]-1-[Bis(4-fluorophenyl)methyl]" to
-- pentanesulfonamide] 1-[Bis(4-fluorophenyl)methyl] --.
Line 54, change "NCH$_2$CH$_2$CH$_2$)" to -- NCH$_2$C$\underline{H}_2$C$\underline{H}_2$) --.
Line 54, change "SCH$_2$CH$_2$" to -- SCH$_2$C$\underline{H}_2$ --.
Line 55, change "NCH$_2$CH$_2$CH$_2$OH)" to -- NCH$_2$C$\underline{H}_2$CH$_2$OH) --.
Line 57, change "NCH$_2$CH$_2$CH$_2$OH)" to -- NC$\underline{H}_2$CH$_2$CH$_2$OH) --.
Line 58, change "NCH$_2$CH$_2$CH$_2$OH)" to -- NCH$_2$CH$_2$C$\underline{H}_2$OH) --.

Column 41,
Line 18, change "NCH$_2$CH$_2$CH$_2$CH$_2$)" to -- NCH$_2$C$\underline{H}_2$C$\underline{H}_2$CH$_2$) --.
Line 19, change "NCH$_2$CH$_2$CH$_2$CH$_2$OH)" to -- NCH$_2$C$\underline{H}_2$C$\underline{H}_2$CH$_2$OH) --.
Line 20, change "SCH$_2$CH$_2$)" to -- SCH$_2$C$\underline{H}_2$) --.
Line 23, change "NCH$_2$CH$_2$CH$_2$CH$_2$OH)" to -- NC$\underline{H}_2$CH$_2$CH$_2$CH$_2$OH)
Line 24, change "NCH$_2$CH$_2$CH$_2$CH$_2$OH)" to -- NCH$_2$CH$_2$CH$_2$C$\underline{H}_2$OH)
Line 52, change "NCH$_2$CH$_2$CH$_2$)" to -- NCH$_2$C$\underline{H}_2$C$\underline{H}_2$) -- .
Line 53, change "NCH$_2$CH$_2$CH$_2$CH$_2$OH)" to -- NCH$_2$C$\underline{H}_2$C$\underline{H}_2$CH$_2$OH) --
Line 54, change "SCH$_2$CH$_2$)" to -- SCH$_2$C$\underline{H}_2$) --.
Line 57, change "NCH$_2$CH$_2$CH$_2$CH$_2$OH)" to -- NC$\underline{H}_2$CH$_2$CH$_2$CH$_2$OH) --
Line 58, change "NCH$_2$CH$_2$CH$_2$CH$_2$OH)" to -- NCH$_2$CH$_2$CH$_2$C$\underline{H}_2$OH) --

UNITED STATES PATENT AND TRADEMARK OFFICE
CERTIFICATE OF CORRECTION

PATENT NO.     : 6,172,228 B1                                              Page 6 of 7
DATED          : January 9, 2001
INVENTOR(S)    : Kenichi Kashima et al.

It is certified that error appears in the above-identified patent and that said Letters Patent is hereby corrected as shown below:

Column 42,
Line 21, change "NCH$_2$CH$_2$CH$_2$CH$_2$)" to -- NCH$_2$C$\underline{H}_2$C$\underline{H}_2$C$\underline{H}_2$) --.
Line 21, change "SCH$_2$CH$_2$)" to -- SCH$_2$C$\underline{H}_2$) --.
Line 24, change "NCH$_2$CH$_2$OH)" to -- NC$\underline{H}_2$CH$_2$OH) --.
Line 25, change "NCH$_2$CH$_2$OH)" to -- NCH$_2$C$\underline{H}_2$OH) --.
Line 54, change "NCH$_2$CH$_2$)" to -- NCH$_2$C$\underline{H}_2$C$\underline{H}_2$) --.
Line 54, change "SCH$_2$CH$_2$)" to -- SCH$_2$C$\underline{H}_2$) --.
Line 57, change "NCH$_2$CH$_2$OH)" to -- NC$\underline{H}_2$CH$_2$OH) --.
Line 58, change "NCH$_2$CH$_2$OH)" to -- NCH$_2$C$\underline{H}_2$OH) --.

Column 43,
Line 20, change "CHCH$_2$CH$_2$)" -- CHC$\underline{H}_2$CH$_2$) -- .
Line 20, change "NCH$_2$ (CH$_2$)" to -- NCH$_2$ (C$\underline{H}_2$) --.
Line 21, change "SCH$_2$CH$_2$)" to -- SCH$_2$C$\underline{H}_2$) --.
Line 23, change "CHCH$_2$CH$_2$)" to -- C$\underline{H}$CH$_2$CH$_2$) -- .
Line 54, change "CHCH$_2$CH$_2$)" to -- CHC$\underline{H}_2$C$\underline{H}_2$) --.
Line 54, change "NCH$_2$ (CH$_2$)" to -- NCH$_2$ (C$\underline{H}_2$) --.
Line 55, change "SCH$_2$CH$_2$)" to -- SCH$_2$C$\underline{H}_2$) --.
Line 57, change "CHCH$_2$CH$_2$)" to -- C$\underline{H}$CH$_2$CH$_2$) --.

Column 44,
Line 20, change "CHCH$_2$CH$_2$)" to -- CHC$\underline{H}_2$C$\underline{H}_2$) --.
Line 20, change "NHCH$_2$ (CH$_2$)$_9$" to -- NCH$_2$(C$\underline{H}_2$)$_9$ --.
Line 21, change "SCH$_2$CH$_2$)" to -- SCH$_2$C$\underline{H}_2$) --.
Line 23, change "CHCH$_2$CH$_2$)" to -- C$\underline{H}$CH$_2$CH$_2$) -- .
Line 51, change "O$_2$s)" to -- O$_2$S) -- .
Line 54, change "NCH$_2$CH$_2$CH$_2$CH$_2$)" to -- NCH$_2$C$\underline{H}_2$C$\underline{H}_2$C$\underline{H}_2$) --.
Line 54, change "SCH$_2$CH$_2$)" to -- SCH$_2$C$\underline{H}_2$) --.

Column 45,
Line 17, change "NCH$_2$CH$_2$CH$_2$)" to -- NCH$_2$C$\underline{H}_2$C$\underline{H}_2$) -- .
Line 17, change "SCH$_2$CH$_2$)" to -- SCH$_2$C$\underline{H}_2$) --.
Line 48, change "CH$_2$CH$_3$x2)" to -- CH$_2$C$\underline{H}_3$x2) --.
Line 48, change "NCH$_2$CH$_2$CH$_2$CH$_2$)" to -- NCH$_2$C$\underline{H}_2$C$\underline{H}_2$C$\underline{H}_2$) --.
Line 49, change "SCH$_2$CH$_2$)" to -- SCH$_2$C$\underline{H}_2$) --.
Line 51, change "CH$_2$CH$_3$x2)" to -- C$\underline{H}_2$CH$_3$x2) --.

UNITED STATES PATENT AND TRADEMARK OFFICE
CERTIFICATE OF CORRECTION

PATENT NO.    : 6,172,228 B1
DATED         : January 9, 2001
INVENTOR(S)   : Kenichi Kashima et al.

It is certified that error appears in the above-identified patent and that said Letters Patent is hereby corrected as shown below:

Column 46,
Line 11, change "$CH_2CH_3x2)$" to -- $CH_2C\underline{H}_3x2)$ --.
Line 11, change "$NCH_2CH_2CH_2)$" to -- $NCH_2C\underline{H}_2CH_2)$ --.
Line 12, change "$SCH_2CH_2)$" to -- $SCH_2C\underline{H}_2)$ --.
Line 14, change "$CH_2CH_3x2)$" to -- $C\underline{H}_2CH_3x2)$ --.
Line 43, change "$CH_2CH_3)$" to -- $CH_2C\underline{H}_3)$ --.
Line 44, change "$NCH_2\,(CH_2)$" to -- $NCH_2\,(C\underline{H}_2)$ --.
Line 45, change "$(CH_2)\,_2CH_3)$" to -- $(C\underline{H}_2)\,_2CH_3)$ --.
Line 45, change "$SCH_2CH_2)$" to -- $SCH_2C\underline{H}_2)$ --.
Line 48, change "$NCH_2\,(CH_2)$" to -- $NC\underline{H}_2\,(CH_2)$ --.

Column 47,
Line 9, change "$CH_2CH_3)$" to -- $CH_2C\underline{H}_3)$ --.
Line 10, change "$NCH_2\,(CH_2)$" to -- $NCH_2\,(C\underline{H}_2)$ --.
Line 11, change "$(CH_2)\,_2CH_3)$" to -- $(C\underline{H}_2)\,_2CH_3)$ --.
Line 11, change "$SCH_2CH_2)$" to -- $SCH_2C\underline{H}_2)$ --.
Line 14, change "$NCH_2\,(CH_2)$" to -- $NC\underline{H}_2\,(CH_2)$ --.

Column 54,
Lines 25-26, change "piperazine compound" to -- piperazinesulfonamide compound --.

Signed and Sealed this

Twenty-third Day of March, 2004

JON W. DUDAS
*Acting Director of the United States Patent and Trademark Office*